US007608683B2

(12) United States Patent
Albani et al.

(10) Patent No.: US 7,608,683 B2
(45) Date of Patent: *Oct. 27, 2009

(54) STRESS PROTEINS AND PEPTIDES AND METHODS OF USE THEREOF

(75) Inventors: Salvatore Albani, Encinitas, CA (US); Berent J. Prakken, Utrechi (NL)

(73) Assignee: The Regents of the University of California, Oakland, CA (US)

( * ) Notice: Subject to any disclaimer, the term of this patent is extended or adjusted under 35 U.S.C. 154(b) by 8 days.

This patent is subject to a terminal disclaimer.

(21) Appl. No.: 11/080,458

(22) Filed: Mar. 14, 2005

(65) Prior Publication Data

US 2006/0039918 A1 Feb. 23, 2006

Related U.S. Application Data

(63) Continuation-in-part of application No. 10/490,949, filed as application No. PCT/US02/30578 on Sep. 25, 2002, and a continuation-in-part of application No. 09/828,574, filed on Apr. 6, 2001, now Pat. No. 6,989,146.

(60) Provisional application No. 60/325,499, filed on Sep. 25, 2001, provisional application No. 60/339,284, filed on Dec. 11, 2001, provisional application No. 60/224,104, filed on Aug. 9, 2000.

(51) Int. Cl.
*C07K 1/00* (2006.01)
*C07K 14/00* (2006.01)
*A61K 39/38* (2006.01)

(52) U.S. Cl. ............ 530/300; 530/350; 424/185.1
(58) Field of Classification Search .......... 530/300
See application file for complete search history.

(56) References Cited

U.S. PATENT DOCUMENTS

| | | | |
|---|---|---|---|
| 4,654,419 A | 3/1987 | Vaughan et al. | 530/326 |
| 4,683,295 A | 7/1987 | Carson | 424/131.1 |
| 4,732,757 A | 3/1988 | Stolle et al. | 424/157.1 |
| 5,116,725 A | 5/1992 | Vaughan et al. | 435/5 |
| 5,310,732 A | 5/1994 | Carson et al. | 514/46 |
| 5,541,164 A | 7/1996 | Carson et al. | 514/46 |
| 5,728,385 A | 3/1998 | Classen | 424/201.1 |
| 5,773,570 A | 6/1998 | Carson et al. | 424/201.1 |
| 5,891,435 A | 4/1999 | Muir et al. | 424/185.1 |
| 5,922,567 A | 7/1999 | Au-Young et al. | 182/165 |
| 5,928,644 A * | 7/1999 | Russell-Jones et al. | 424/190.1 |
| 5,993,803 A | 11/1999 | Cohen et al. | 424/93.71 |
| 6,007,821 A | 12/1999 | Srivastava et al. | 424/193.1 |
| 6,037,135 A | 3/2000 | Kubo et al. | 435/7.24 |
| 6,455,503 B1 * | 9/2002 | Srivastava | 514/21 |
| 6,610,836 B1 * | 8/2003 | Breton et al. | 536/23.1 |
| 6,989,146 B2 * | 1/2006 | Albani et al. | 424/185.1 |
| 2002/0146759 A1 | 10/2002 | Albani et al. | |
| 2006/0093574 A1 * | 5/2006 | Albani et al. | 424/85.1 |

FOREIGN PATENT DOCUMENTS

| | | |
|---|---|---|
| WO | WO 90/14835 | 12/1990 |
| WO | WO 95/25744 | 9/1995 |
| WO | WO 95/31984 | 11/1995 |
| WO | WO 96/10039 | 4/1996 |
| WO | WO 97/11966 | 4/1997 |
| WO | WO 97/34002 | 9/1997 |
| WO | WO 99/61916 | 12/1999 |
| WO | WO 01/16174 A3 | 3/2001 |
| WO | WO 03/026579 * | 4/2003 |

OTHER PUBLICATIONS

Guichard et al (PNAS USA, vol. 91, Oct. 1994, pp. 9765-9769).*
Albani, S., et al., "A Multistep Molecular Mimicry Hypothesis for the Pathogenesis of Rheumatoid Arthritis," *Immunology Today*, vol. 17, No. 10, pp. 466-470, Oct. 1996.
Albani, et al., "Genetic and Environmental Factors in the Immune Pathogenesis of Rheumatoid Arthritis," *Rheumatic Disease Clinics of North America*, 18/4:729-740, 1992.
Albani et al, "HLA Binding Studies Support a Role for the QKRAA Susceptibility Sequence to Rheumatoid Arthritis (RA) in Positive Selection and Activation of Pathogenic T Lymphocytes," *Arthritis and Rheumatism*, 38/9 Suppl., p. S181, Abstract#173, 1995.
Albani, S., et al., "Immune Responses to the *Escherichia coli* dnaJ Heat Shock Protein in Juvenile Rheumatoid Arthritis and their Correlation with Disease Activity," *The Journal of Pediatrics*, vol. 124, No. 4, pp. 561-565, Apr. 1994.
Albani, S., et al., "Molecular Basis for the Association Between HLA DR4 and Rheumatoid Arthritis. From the Shared Epitope Hypothesis to a Peptidic Model of Rheumatoid Arthritis," *Clin. Biochem.* vol. 25, pp. 209-212, 1992.
Albani, S., et al., "Positive Selection in Autoimmunity: Abnormal Immune Responses to a Bacterial dnaJ Antigen Determinant in Patients with Early Rheumatoid Arthritis," *Nature Medicine*, vol. 1, No. 5, pp. 448-452, 1995.
Albani, S., et al., "The Susceptibility Sequence to Rheumatoid Arthritis is a Cross-Reactive B Cell Epitope Shared by the *Escherichia coli* Heat Shock Protein dnaJ and the Histocompatibility Leukocyte Antigen DRB10401 Molecule," *J. Clin. Invest.*, vol. 89, pp. 327-331, 1992.
Anderton, S.M., et al. "Activation of T Cells Recognizing Self 60-kD Heat Shock Protein Can Protect Against Experimental Arthritis,"*J. Exp. Med.*, vol. 181, pp. 943-952, Mar. 1995.

(Continued)

*Primary Examiner*—Mark Navarro
(74) *Attorney, Agent, or Firm*—DLA Piper LLP (US)

(57) ABSTRACT

Provided are HLA pan DR-binding peptides and methods of using such peptides to modulate, block, or inhibit immune responses to effect treatment of immune-mediated diseases and conditions, such as inflammatory and autoimmune diseases, cancer, and microbial infections. These peptides and methods are also useful diagnostically to screen peptide or peptide analogs that can inhibit the pathogenic immune response or up-regulate an immune response against aberrant or invading cells, to monitor efficacy for therapeutic treatments, and to identify other agents that may be effective to inhibit or otherwise modulate an immune response such as by altering T cell functional phenotype, and even more particularly by modulating the regulatory phenotype of regulatory T cells and/or inducing emergence of T cells with a different functional phenotype.

10 Claims, 30 Drawing Sheets

OTHER PUBLICATIONS

Anderton et al, "Differential Mycobacterial 65-kDa Heat Shock Protein T Cell Epitope Recognition after Adjuvant Arthritis-Inducing or Protective Immunization Protocols[1]," *J. Immunology* 152:3656-64, 1994.

Asseldonk, M., et al., "Cloning, Nucleotide Sequence, and Regulatory Analysis of the *Lactococcus lactis dnaJ* Gene,", *Journal of Bacteriology*, 175(6), pp. 1637-1644, Mar. 1993.

Auger, I., et al., "HLA-DR4 and HLA-DR10 Motifs that Carry Susceptibility to Rheumatoid Arthritis Bind 70-kD Heat Shock Proteins," *Nature Medicine*, vol. 2, No. 3, pp. 306-310, Mar. 1996.

Bardwell, J.C.A., et al., "The Nucleotide Sequence of the *Escherichia coli* K12 dnaJ+ Gene," *The Journal of Biological Chemistry*, vol. 261, No. 4, pp. 1782-1785, Feb. 5, 1986.

Bonnin, D., et al., "MHC-Derived Peptides Drive Positive T Cell Selection in the Thymus: from a Physiological System to an HLA DRB1 0401 Transgenic Mouse Model for Rheumatoid Arthritis?", *Arthritis and Rheumatism*, vol. 39, No. 9 Suppl., p. S160, Oct. 1996.

Brackertz et al, "OM-8980 in Rheumatoid Arthritis: A 6-Month Double Blind Placebo Controlled Multicenter Study," *Journal of Rheumatology*, vol. 16, pp. 19-23, 1989.

DeGraeff-Meeder, E.R., et al., "Recognition of Human 60kD Heat Shock Protein by Mononuclear Cells from Patients with Juvenile Chronic Arthritis," *The Lancet*, vol. 337, pp. 1368-1372, Jun. 8, 1991.

Fairchild, P., et al., "Peptide-MHC Interaction in Autoimmunity," *Current Opinion in Immunology*, vol. 4, pp. 748-753, 1992.

Geluk et al., "Identification of HLA Class II-restricted Determinants of Mycobacterium Tuberculosis-derived Proteins by Using HLA-Transgenic, Class II-deficient Mice," *Proceedings of the National Academy of Science*, vol. 95, pp. 10797-10802, 1998.

La Cava, A., et al., "The QKRAA Disease Susceptibility Sequence for Rheumatoid Arthritis (RA) is a B Cell Epitope Shared by the Epstein-Barr Virus (EBV) Protein gp110 and the *E. coli* Heat Shock Protein dnaJ Possible Implications for Disease Pathogenesis," *Arthritis & Rheum.* 36(9) Suppl. pp. S127 Abstract 1993.

Life, P.F., et al., "Synovial Fluid Antigen-Presenting Cells Unmask Peripheral Blood T Cell Responses to Bacterial Antigens in Inflammatory Arthritis," *Clin. Exp. Immunol.* vol. 79, pp. 189-194, 1990.

Marsh, S.G.E., et al, "HLA Class II Nucleotide Sequences, 1991," *Tissue Antigens*, vol. 37, pp. 181-189, 1991.

Meeker, et al. "Analysis of Human Antibodies Epitopes on the 65-Kilodalton Protein of *Mycobacterium lepare* by Using Synthetic Peptides", *Infection and Immunity, American Society for Microbiology, Washington, D.C, US*, vol. 57, No. 12, 3689-3694, Dec. 1989.

Nepom, G., "Prediction of Susceptibility to Rheumatoid Arthritis by Human Leukocyte Antigen Genotying" *Rheumatic Disease Clinics of North America*, vol. 18, No. 4, pp. 785-792, Nov. 1992.

Ohki, M., et al., "Nucleotide Sequence of the *Escherichia coli* dnaJ Gene and Purification of the Gene Product", The Journal of Biological Chemistry, vol. 261, No. 4, pp. 1778-1781, 1986.

Plotkin, S.A., et al., "New Technologies for Making Vaccines," *Vaccines*, pp. 568-575, 1988.

Prakken et al. "Epitope: Mapping of Hsp60 T Cell Responses in Children with Pauci Articular Juvenile Rheumatoid Arthritis by Prediction of PAN-HLA DR. Binding Sites", *Arthritis and Rheumatism, Lippincott, Philadelphia, US*, vol. 42, No. 9 Supplement, S229, Sep. 1999.

Prakken, et al., "Peptide-induced nasal tolerances for a mycobacterial heat shock protein 60 T cell epitope in rats suppresses both adjuvant arthritis and nonmicrobially induced experimental arthritis", *Proceedings of the National Academy of Sciences, USA*, vol. 94, 3284-3289, Apr. 1997.

Prakken et al., "Identification of Pan-DR Binding T Cell Epitopes of Human and Mycobacterial hsp60 in Patients with Juvenile Idiopathic Arthritis", *Conference of Immunologist*, p. 1, Jan. 2001.

Silver, P.A., et al. "Eukaryotic DnaJ Homologs and the Specificity of Hsp70 Activity," *Cell*, vol. 74, pp. 5-6, Jul. 16, 1993.

Stastney, P., et al., "Immunogenetics of Rheumatoid Arthritis and Juvenile Arthritis", *Recenti Progressi in Medicina*, vol. 82, No. 7-8, pp. 409-416, 1991.

Van Den Broek, M.F., et al., "Protection Against Streptococcal Cell Wall-Induced Arthritis by Pretreatment with the 65-kD Mycobacterial Heat Shock Protein," *J. Exp. Med.*, vol. 170, pp. 449-466, Aug. 1989.

van Eden, W., et al., "Cloning of the Mycobacterial Epitope Recognized by T Lymphocytes in Adjuvant Arthritis," *Nature*, vol. 331, pp. 171-173, Jan. 14, 1988.

Weyand, C., et al., "The Influence of HLA-DRB1 Genes on Disease Severity in Rheumatoid Arthritis," *Annals of Internal Medicine*, vol. 117, No. 10, pp. 801-806, Nov. 15, 1992.

Zuber et al., "Cloning, Sequencing and Expression of the *dnaJ* gene of *Coxiella burnetii*," *Gene*, vol. 152 pp. 99-102, 1995.

\* cited by examiner

FIGURE 1

| | | | | | |
|---|---|---|---|---|---|
| MAAKD | VKFGN | DARVK | MLRGV | NVLAD | AVKVT |
| LGPKG | RNVVL | DKSFG | APTIT | KDGVS | VAREI |
| ELEDK | FENMG | AQMVK | EVASK | ANDAA | GDGTT |
| TATVL | AQAII | TEGLK | AVAAG | MNPMD | LKRGI |
| DKAVT | AAVEE | LKALS | VPCSD | SKAIA | QVGTI |
| SANSD | ETVGK | LIAEA | MDKVG | KEGVI | TVEDG |
| TGLQD | ELDVV | EGMQF | DRGYL | SPYFI | NKPET |
| GAVEL | ESPFI | LLADK | KISNI | REMLP | VLEAV |
| AKAGK | PLLII | AEDVE | GEALA | TLVVN | TMRGI |
| VKVAA | VKAPG | FGDRR | KAMLQ | DIATL | TGGTV |
| ISEEI | GMELE | KATLE | DLGQA | KRVVI | NKDTT |
| TIIDG | VGEEA | AIQGR | VAQIR | QQIEE | ATSDY |
| DREKL | QERVA | KLAGG | VAVIK | VGAAT | EVEMK |
| EKKAR | VEDAL | HATRA | AVEEG | VVAGG | GVALI |
| RVASK | LADLR | GQNED | QNVGI | KVALR | AMEAP |
| LRQIV | LNCGE | EPSVV | ANTVK | GGDGN | YGYNA |
| ATEEY | GNMID | MGILD | PTKVT | RSALQ | YAASV |
| AGLMI | TTECM | VTDLP | KNDAA | DLGAA | GGMGG |
| MGGMG | GMM | | | | |

FIGURE 2

| | | | | | |
|---|---|---|---|---|---|
| MLRLP | TVFRQ | MRPVS | RVLAP | HLTRA | YAKDV |
| KFGAD | ARALM | LQGVD | LLADA | VAVTM | GPKGR |
| TVIIE | QGWGS | PKVTK | DGVTV | AKSID | LKDKY |
| KNIGA | KLVQD | VANNT | NEEAG | DGTTT | ATVLA |
| RSIAK | EGFEK | ISKGA | NPVEI | RRGVM | LAVDA |
| VIAEL | KKQSK | PVTTP | EEIAQ | VATIS | ANGDK |
| EIGNI | ISDAM | KKVGR | KGVIT | VKDGK | TLNDE |
| LEIIE | GMKFD | RGYIS | PYFIN | TSKGQ | KCEFQ |
| DAYVL | LSEKK | ISSIQ | SIVPA | LEIAN | AHRKP |
| LVIIA | EDVDG | EALST | LVLNR | LKVGL | QVVAV |
| KAPGF | GDNRK | NQLKD | MAIAT | GGAVF | GEEGL |
| TLNLE | DVQPH | DLGKV | GEVIV | TKDDA | MLLKG |
| KGDKA | QIEKR | IQEII | EQLDV | TTSEY | EKEKL |
| NERLA | KLSDG | VAVLK | VGGTS | DVEVN | EKKDR |
| VTDAL | NATRA | AVEEG | IVLGG | GCALL | RCIPA |
| LDSLT | PANED | QKIGI | EIIKR | TLKIP | AMTIA |
| KNAGV | EGSLIV | EKIMQ | SSSEV | GYDAM | AGDFV |
| NMVEK | GIIDP | TKVV | TALLD | AAGVA | SLLTT |
| AEVVV | TEIPK | EEKDP | GMGAM | GGMGG | GMGGG |
| MF | | | | | |

FIGURE 3

| | | | | | |
|---|---|---|---|---|---|
| MAKQD | YYEIL | GVSKT | AEERE | IRKAY | KRLAM |
| KYHPD | RNQGD | KEAEA | KFKEI | KEAYE | VLTDS |
| QKRAA | YDQYG | HAAFE | QGGMG | GGGFG | GGADF |
| SDIFG | DVFGD | IFGGG | RGRQR | AARGA | DLRYN |
| MELTLE | EAVRG | VTKEI | RIPTL | EECDV | CHGSG |
| AKPGT | QPQTC | PTCHG | SGQVQ | MRQGF | FAVQQ |
| TCPHC | QGRGT | LIKDP | CNKCH | GHGRV | ERSKT |
| LSVKI | PAGVD | TGDRI | RLAGE | GEAGE | HGAPA |
| GDLYV | QVQVK | QHPIF | EREGN | NLYCE | VPINF |
| AMAAL | GGEIE | VPTLD | GRVKL | KVPGE | TQTGK |
| LFRMR | GKGVK | SVRGG | AQGDL | LCRVV | VETPV |
| GLNER | QKQLL | QELQE | SFGGP | TGEHN | SPRS |
| KSFFD | GVKKF | FDDLT | R | | |

FIGURE 4

| | | | | | |
|---|---|---|---|---|---|
| MAKTI | AYDEE | ARRGL | ERGLN | ALADA | VKVTL |
| GPKGR | NVVLE | KKWGA | PTITN | DGVSI | AKEIE |
| LEDPY | EKIGA | ELVKE | VAKKT | DDVAG | DGTTT |
| ATVLA | QALVR | EGLRN | VAAGA | NPLGL | KRGIE |
| KAVEK | VTETL | LKGAK | EVETK | EQIAA | TAAIS |
| AGDQS | IGDLI | AEAMD | KVGNE | GVITV | EESNT |
| FGLQL | ELTEG | MRFDK | GYISG | YFVTD | PEQEA |
| VLEDP | YILLV | SSKVS | TVKDL | LPLLE | KVIGA |
| GKPLL | IIAED | VEGEA | LSTLV | VNKIR | GTFKS |
| VAVKA | PGFGD | RRKAM | LQDMA | ILTGG | QVISE |
| EVGLT | LENAD | LSLLG | KARKV | VVTKD | ETTIV |
| EGAGD | TDAIA | GRVAQ | IRQEI | ENSDS | DYDRE |
| KLQER | AKLAG | GVAVI | KAGAA | TEVEL | KERKH |
| RIEDA | VRNAK | AAVEE | GIVAG | GGVTL | LQAAP |
| TLDEL | KLEGD | EATGA | NIVKV | ALEAP | LKQIA |
| FNSGL | EPGVV | AEKVR | NLPAG | HGLNA | QTGVY |
| EDLLA | AGVAD | PVKVT | RSALQ | NAASI | AGLFL |
| TTEAV | VADKP | EKEKA | SVPGG | GDMGG | MDF |

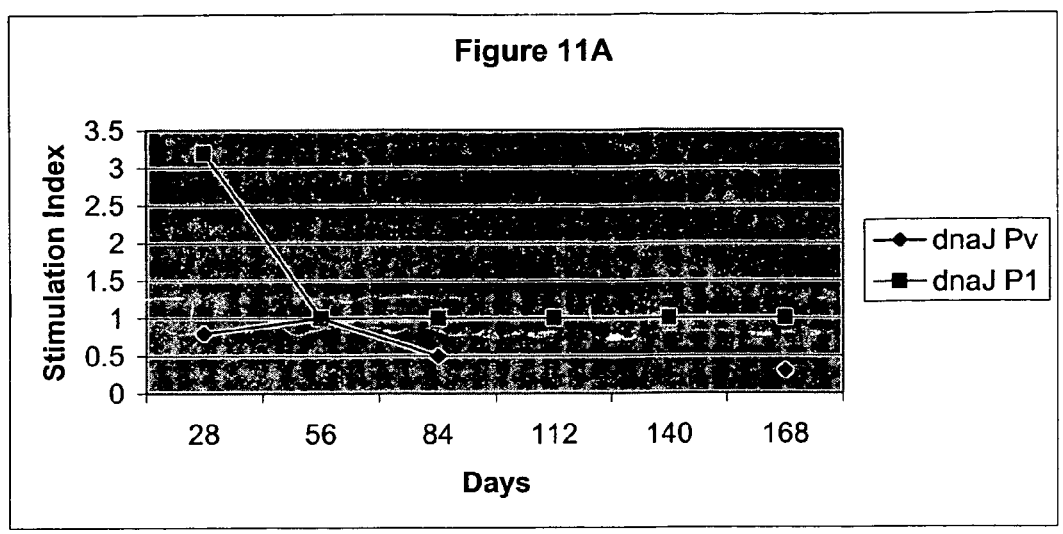
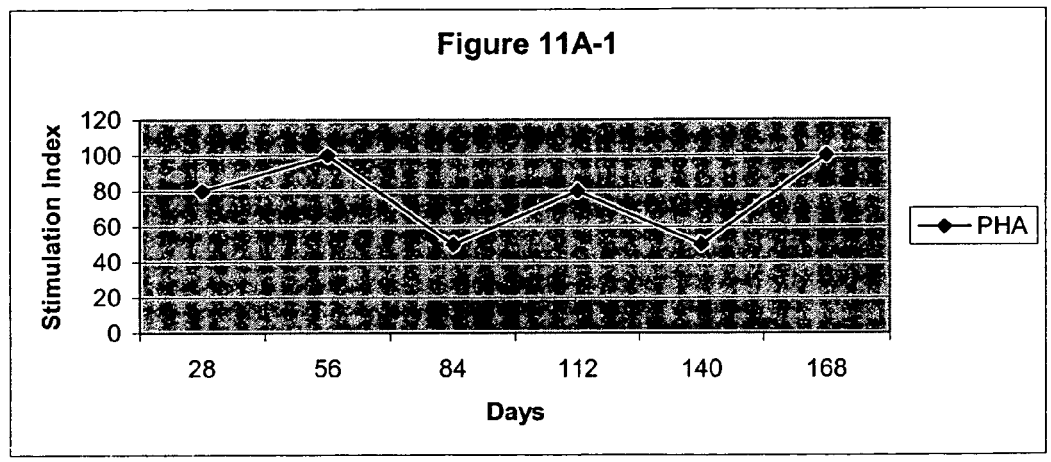

Tender Joint Score

Swollen Joint Score

Figure 19A
Figure 19B
Figure 19C
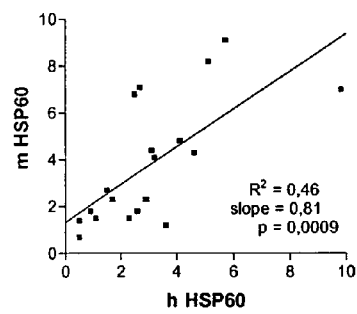
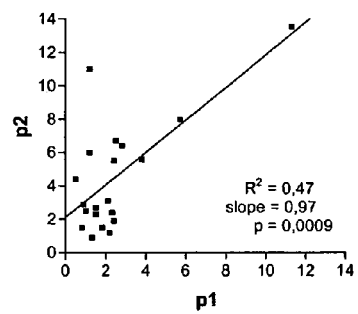
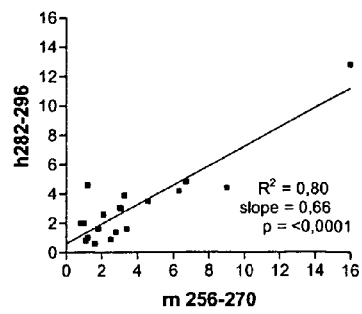

FIGURE 20 A and B
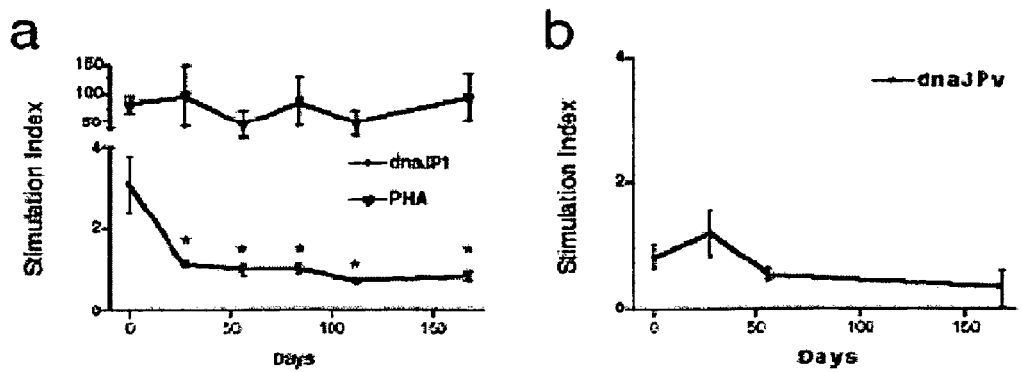
FIGURE 20 C and D
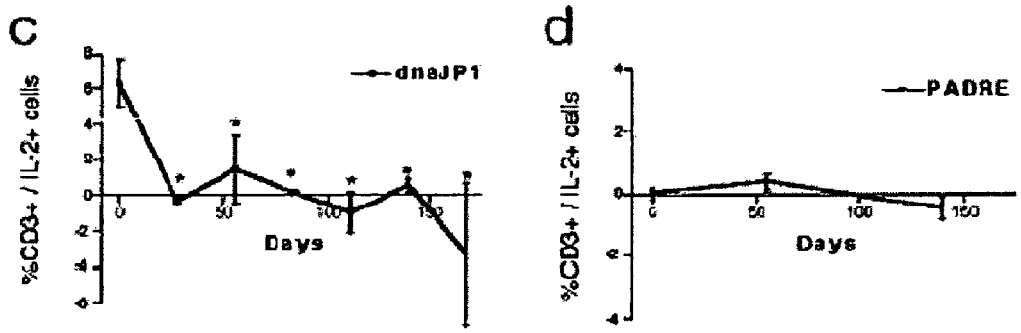
FIGURE 20 E and F
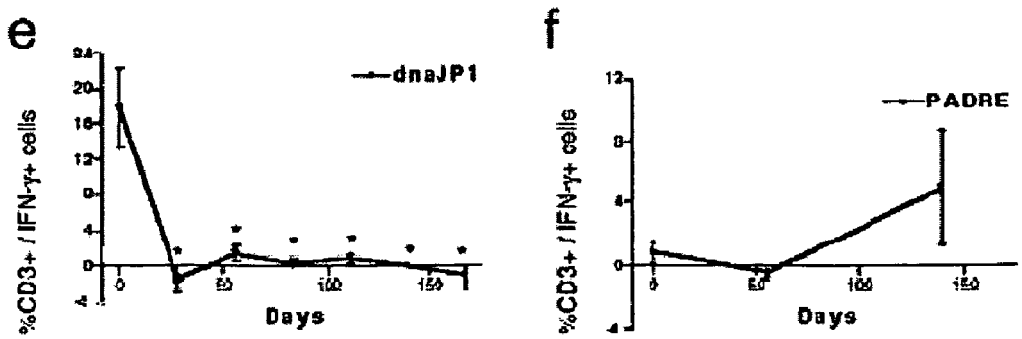

FIGURE 20 G and H
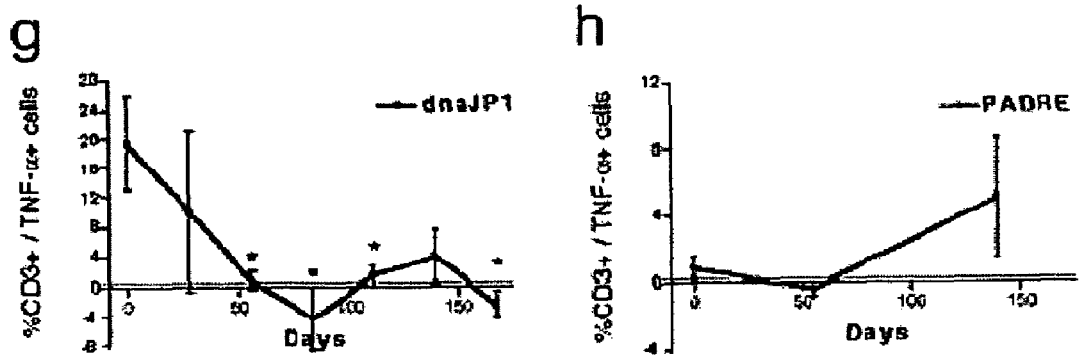
FIGURE 20 I and J
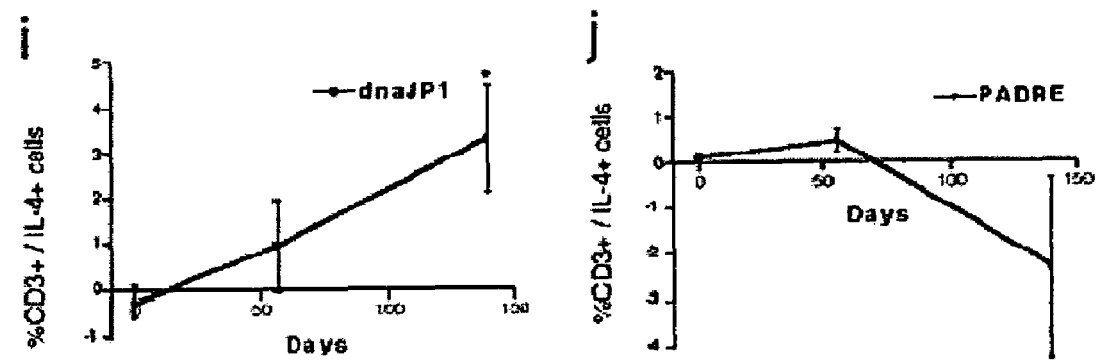
FIGURE 20 K and L
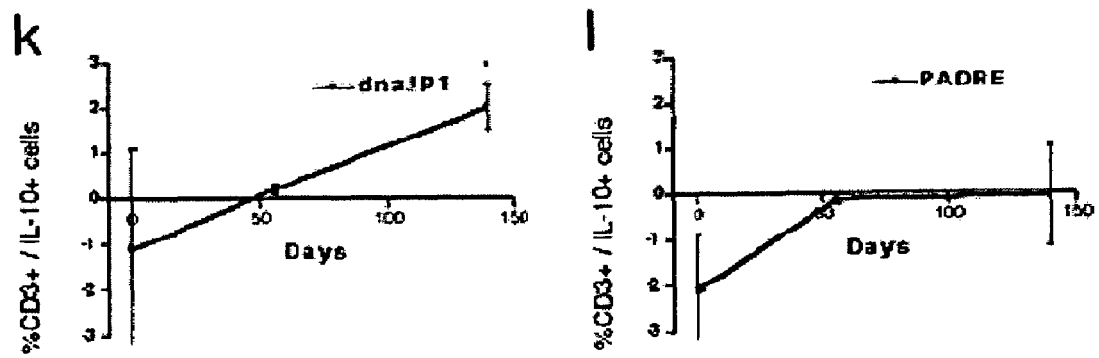

SEQUENCE LISTING

<160> NUMBER OF SEQ ID NOS: 47

<210> SEQ ID NO 1
<211> LENGTH: 15
<212> TYPE: PRT
<213> ORGANISM: Mycobacterium

<400> SEQUENCE: 1

Gly Glu Ala Leu Ser Thr Leu Val Val Asn Lys Ile Arg Gly Thr
1               5                   10                  15

```
<210> SEQ ID NO 2
<211> LENGTH: 15
<212> TYPE: PRT
<213> ORGANISM: Mycobacterium

<400> SEQUENCE: 2

Gly Glu Ala Leu Ser Thr Leu Val Val Asn Lys Ile Arg Gly Thr
1               5                   10                  15

<210> SEQ ID NO 3
<211> LENGTH: 15
<212> TYPE: PRT
<213> ORGANISM: Homo sapiens

<400> SEQUENCE: 3

Gly Glu Ala Leu Ser Thr Leu Val Leu Asn Arg Leu Lys Val Gly
1               5                   10                  15

<210> SEQ ID NO 4
<211> LENGTH: 15
<212> TYPE: PRT
<213> ORGANISM: Mycobacterium

<400> SEQUENCE: 4

Pro Tyr Ile Leu Leu Val Ser Ser Lys Val Ser Thr Val Lys Asp
1               5                   10                  15

<210> SEQ ID NO 5
<211> LENGTH: 15
<212> TYPE: PRT
<213> ORGANISM: Homo sapiens

<400> SEQUENCE: 5

Ala Tyr Val Leu Leu Ser Glu Lys Lys Ile Ser Ser Ile Gln Ser
1               5                   10                  15

<210> SEQ ID NO 6
<211> LENGTH: 15
<212> TYPE: PRT
<213> ORGANISM: Mycobacterium

<400> SEQUENCE: 6

Glu Ala Val Leu Glu Asp Pro Tyr Ile Leu Leu Val Ser Ser Lys
1               5                   10                  15

<210> SEQ ID NO 7
<211> LENGTH: 15
<212> TYPE: PRT
<213> ORGANISM: Homo sapiens

<400> SEQUENCE: 7

Lys Cys Glu Phe Gln Asp Ala Tyr Val Leu Leu Ser Glu Lys Lys
1               5                   10                  15

<210> SEQ ID NO 8
<211> LENGTH: 15
<212> TYPE: PRT
<213> ORGANISM: Mycobacterium

<400> SEQUENCE: 8

Ile Ala Gly Leu Phe Leu Thr Thr Glu Ala Val Val Ala Asp Lys
1               5                   10                  15
```

```
<210> SEQ ID NO 9
<211> LENGTH: 15
<212> TYPE: PRT
<213> ORGANISM: Homo sapiens

<400> SEQUENCE: 9

Val Ala Ser Leu Leu Thr Thr Ala Glu Val Val Thr Glu Ile
1               5                   10                  15

<210> SEQ ID NO 10
<211> LENGTH: 15
<212> TYPE: PRT
<213> ORGANISM: Artificial sequence
<220> FEATURE:
<223> OTHER INFORMATION: Synthetic construct

<400> SEQUENCE: 10

Gln Lys Arg Ala Ala Tyr Asp Gln Tyr Gly His Ala Ala Phe Glu
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: Synthetic construct

<400> SEQUENCE: 11

Asp Glu Arg Ala Ala Tyr Asp Gln Tyr Gly His Ala Ala Phe Glu
1               5                   10                  15

<210> SEQ ID NO 12
<211> LENGTH: 11
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any naturally occurring amino acid

<400> SEQUENCE: 12

Lys Xaa Val Ala Ala Trp Thr Leu Lys Ala Ala
1               5                   10

<210> SEQ ID NO 13
<211> LENGTH: 572
<212> TYPE: PRT
<213> ORGANISM: Homo sapiens hsp60

<400> SEQUENCE: 13

Met Leu Arg Leu Pro Thr Val Phe Arg Gln Met Arg Pro Val Ser Arg
1               5                   10                  15

Val Leu Ala Pro His Leu Thr Arg Ala Tyr Ala Lys Asp Val Lys Phe
                20                  25                  30

Gly Ala Asp Ala Arg Ala Leu Met Leu Gln Gly Val Asp Leu Leu Ala
            35                  40                  45

Asp Ala Val Ala Val Thr Met Gly Pro Lys Gly Arg Thr Val Ile Ile
        50                  55                  60

Glu Gln Gly Trp Gly Ser Pro Lys Val Thr Lys Asp Gly Val Thr Val
65                  70                  75                  80

Ala Lys Ser Ile Asp Leu Lys Asp Lys Tyr Lys Asn Ile Gly Ala Lys
                85                  90                  95
```

-continued

```
Leu Val Gln Asp Val Ala Asn Thr Asn Glu Glu Ala Gly Asp Gly
                100                 105                 110

Thr Thr Thr Ala Thr Val Leu Ala Arg Ser Ile Ala Lys Glu Gly Phe
            115                 120                 125

Glu Lys Ile Ser Lys Gly Ala Asn Pro Val Glu Ile Arg Arg Gly Val
        130                 135                 140

Met Leu Ala Val Asp Ala Val Ile Ala Glu Leu Lys Lys Gln Ser Lys
145                 150                 155                 160

Pro Val Thr Thr Pro Glu Ile Ala Gln Val Ala Thr Ile Ser Ala
                165                 170                 175

Asn Gly Asp Lys Glu Ile Gly Asn Ile Ile Ser Asp Ala Met Lys Lys
            180                 185                 190

Val Gly Arg Lys Gly Val Ile Thr Val Lys Asp Gly Lys Thr Leu Asn
        195                 200                 205

Asp Glu Leu Glu Ile Ile Glu Gly Met Lys Phe Asp Arg Gly Tyr Ile
    210                 215                 220

Ser Pro Tyr Phe Ile Asn Thr Ser Lys Gly Gln Lys Cys Glu Phe Gln
225                 230                 235                 240

Asp Ala Tyr Val Leu Leu Ser Glu Lys Lys Ile Ser Ser Ile Gln Ser
                245                 250                 255

Ile Val Pro Ala Leu Glu Ile Ala Asn Ala His Arg Lys Pro Leu Val
            260                 265                 270

Ile Ile Ala Glu Asp Val Asp Gly Glu Ala Leu Ser Thr Leu Val Leu
        275                 280                 285

Asn Arg Leu Lys Val Gly Leu Gln Val Val Ala Val Lys Ala Pro Gly
    290                 295                 300

Phe Gly Asp Asn Arg Lys Asn Gln Leu Lys Asp Met Ala Ile Ala Thr
305                 310                 315                 320

Gly Gly Ala Val Phe Gly Glu Glu Gly Leu Thr Leu Asn Leu Glu Asp
                325                 330                 335

Val Gln Pro His Asp Leu Gly Lys Val Gly Glu Val Ile Val Thr Lys
            340                 345                 350

Asp Asp Ala Met Leu Leu Lys Gly Lys Gly Asp Lys Ala Gln Ile Glu
        355                 360                 365

Lys Arg Ile Gln Glu Ile Ile Glu Gln Leu Asp Val Thr Thr Ser Glu
    370                 375                 380

Tyr Glu Lys Glu Lys Leu Asn Glu Arg Leu Ala Lys Leu Ser Asp Gly
385                 390                 395                 400

Val Ala Val Leu Lys Val Gly Gly Thr Ser Asp Val Glu Val Asn Glu
                405                 410                 415

Lys Lys Asp Arg Val Thr Asp Ala Leu Asn Ala Thr Arg Ala Ala Val
            420                 425                 430

Glu Glu Gly Ile Val Leu Gly Gly Cys Ala Leu Leu Arg Cys Ile
        435                 440                 445

Pro Ala Leu Asp Ser Leu Thr Pro Ala Asn Glu Asp Gln Lys Ile Gly
    450                 455                 460

Ile Glu Ile Ile Lys Arg Thr Leu Lys Ile Pro Ala Met Thr Ile Ala
465                 470                 475                 480

Lys Asn Ala Gly Val Glu Gly Ser Leu Ile Val Glu Lys Ile Met Gln
                485                 490                 495

Ser Ser Ser Glu Val Gly Tyr Asp Ala Met Ala Gly Asp Phe Val Asn
            500                 505                 510

Met Val Glu Lys Gly Ile Ile Asp Pro Thr Lys Val Val Thr Ala Leu
```

```
                515                 520                 525
Leu Asp Ala Ala Gly Val Ala Ser Leu Leu Thr Thr Ala Glu Val Val
        530                 535                 540

Val Thr Glu Ile Pro Lys Glu Glu Lys Asp Pro Gly Met Gly Ala Met
545                 550                 555                 560

Gly Gly Met Gly Gly Gly Met Gly Gly Gly Met Phe
                565                 570
```

<210> SEQ ID NO 14
<211> LENGTH: 9
<212> TYPE: PRT
<213> ORGANISM: Mycobacterium

<400> SEQUENCE: 14

```
Leu Ser Thr Leu Val Val Asn Lys Ile
1               5
```

<210> SEQ ID NO 15
<211> LENGTH: 9
<212> TYPE: PRT
<213> ORGANISM: Homo sapiens

<400> SEQUENCE: 15

```
Leu Ser Thr Leu Val Leu Asn Arg Leu
1               5
```

<210> SEQ ID NO 16
<211> LENGTH: 9
<212> TYPE: PRT
<213> ORGANISM: Mycobacterium

<400> SEQUENCE: 16

```
Leu Val Ser Ser Lys Val Ser Thr Val
1               5
```

<210> SEQ ID NO 17
<211> LENGTH: 9
<212> TYPE: PRT
<213> ORGANISM: Mycobacterium

<400> SEQUENCE: 17

```
Tyr Ile Leu Leu Val Ser Ser Lys Val
1               5
```

<210> SEQ ID NO 18
<211> LENGTH: 9
<212> TYPE: PRT
<213> ORGANISM: Homo sapiens

<400> SEQUENCE: 18

```
Leu Ser Glu Lys Lys Ile Ser Ser Ile
1               5
```

<210> SEQ ID NO 19
<211> LENGTH: 9
<212> TYPE: PRT
<213> ORGANISM: Mycobacterium

<400> SEQUENCE: 19

```
Leu Glu Asp Pro Tyr Ile Leu Leu Val
1               5
```

<210> SEQ ID NO 20

```
<211> LENGTH: 9
<212> TYPE: PRT
<213> ORGANISM: Homo sapiens

<400> SEQUENCE: 20

Phe Gln Asp Ala Tyr Val Leu Leu Ser
1               5

<210> SEQ ID NO 21
<211> LENGTH: 9
<212> TYPE: PRT
<213> ORGANISM: Mycobacterium

<400> SEQUENCE: 21

Leu Thr Thr Glu Ala Val Val Ala Asp
1               5

<210> SEQ ID NO 22
<211> LENGTH: 9
<212> TYPE: PRT
<213> ORGANISM: Mycobacterium

<400> SEQUENCE: 22

Phe Leu Thr Thr Glu Ala Val Val Ala
1               5

<210> SEQ ID NO 23
<211> LENGTH: 9
<212> TYPE: PRT
<213> ORGANISM: Homo sapiens

<400> SEQUENCE: 23

Leu Thr Thr Ala Glu Val Val Val Thr
1               5

<210> SEQ ID NO 24
<211> LENGTH: 15
<212> TYPE: PRT
<213> ORGANISM: Escherichia coli

<400> SEQUENCE: 24

Gly Glu Ala Leu Ala Thr Leu Val Val Asn Thr Met Arg Gly Ile
1               5                   10                  15

<210> SEQ ID NO 25
<211> LENGTH: 15
<212> TYPE: PRT
<213> ORGANISM: Escherichia coli

<400> SEQUENCE: 25

Pro Phe Ile Leu Leu Ala Asp Lys Lys Ile Ser Asn Ile Arg Glu
1               5                   10                  15

<210> SEQ ID NO 26
<211> LENGTH: 15
<212> TYPE: PRT
<213> ORGANISM: Escherichia coli

<400> SEQUENCE: 26

Ala Val Glu Leu Glu Ser Pro Phe Ile Leu Leu Ala Asp Lys Lys
1               5                   10                  15

<210> SEQ ID NO 27
<211> LENGTH: 15
<212> TYPE: PRT
```

-continued

<213> ORGANISM: Escherichia coli

<400> SEQUENCE: 27

Val Ala Gly Leu Met Ile Thr Thr Glu Cys Met Val Thr Asp Leu
1               5                   10                  15

<210> SEQ ID NO 28
<211> LENGTH: 9
<212> TYPE: PRT
<213> ORGANISM: Escherichia coli

<400> SEQUENCE: 28

Leu Ala Thr Leu Val Val Asn Thr Met
1               5

<210> SEQ ID NO 29
<211> LENGTH: 9
<212> TYPE: PRT
<213> ORGANISM: Escherichia coli

<400> SEQUENCE: 29

Leu Leu Ala Asp Lys Lys Ile Ser Asn
1               5

<210> SEQ ID NO 30
<211> LENGTH: 9
<212> TYPE: PRT
<213> ORGANISM: Escherichia coli

<400> SEQUENCE: 30

Leu Glu Ser Pro Phe Ile Leu Leu Ala
1               5

<210> SEQ ID NO 31
<211> LENGTH: 9
<212> TYPE: PRT
<213> ORGANISM: Escherichia coli

<400> SEQUENCE: 31

Leu Met Ile Thr Thr Glu Cys Met Val
1               5

<210> SEQ ID NO 32
<211> LENGTH: 376
<212> TYPE: PRT
<213> ORGANISM: Escherichia coli dnaJ

<400> SEQUENCE: 32

Met Ala Lys Gln Asp Tyr Tyr Glu Ile Leu Gly Val Ser Lys Thr Ala
1               5                   10                  15

Glu Glu Arg Glu Ile Arg Lys Ala Tyr Lys Arg Leu Ala Met Lys Tyr
                20                  25                  30

His Pro Asp Arg Asn Gln Gly Asp Lys Glu Ala Glu Ala Lys Phe Lys
            35                  40                  45

Glu Ile Lys Glu Ala Tyr Glu Val Leu Thr Asp Ser Gln Lys Arg Ala
        50                  55                  60

Ala Tyr Asp Gln Tyr Gly His Ala Ala Phe Glu Gln Gly Gly Met Gly
65                  70                  75                  80

Gly Gly Gly Phe Gly Gly Gly Ala Asp Phe Ser Asp Ile Phe Gly Asp
                85                  90                  95

Val Phe Gly Asp Ile Phe Gly Gly Gly Arg Gly Arg Gln Arg Ala Ala
                100                 105                 110

Arg Gly Ala Asp Leu Arg Tyr Asn Met Glu Leu Thr Leu Glu Glu Ala
         115                 120                 125

Val Arg Gly Val Thr Lys Glu Ile Arg Ile Pro Thr Leu Glu Glu Cys
    130                 135                 140

Asp Val Cys His Gly Ser Gly Ala Lys Pro Gly Thr Gln Pro Gln Thr
145                 150                 155                 160

Cys Pro Thr Cys His Gly Ser Gly Gln Val Gln Met Arg Gln Gly Phe
                165                 170                 175

Phe Ala Val Gln Gln Thr Cys Pro His Cys Gln Gly Arg Gly Thr Leu
            180                 185                 190

Ile Lys Asp Pro Cys Asn Lys Cys His Gly His Gly Arg Val Glu Arg
        195                 200                 205

Ser Lys Thr Leu Ser Val Lys Ile Pro Ala Gly Val Asp Thr Gly Asp
    210                 215                 220

Arg Ile Arg Leu Ala Gly Glu Gly Glu Ala Gly Glu His Gly Ala Pro
225                 230                 235                 240

Ala Gly Asp Leu Tyr Val Gln Val Gln Val Lys Gln His Pro Ile Phe
                245                 250                 255

Glu Arg Glu Gly Asn Asn Leu Tyr Cys Glu Val Pro Ile Asn Phe Ala
            260                 265                 270

Met Ala Ala Leu Gly Gly Glu Ile Glu Val Pro Thr Leu Asp Gly Arg
        275                 280                 285

Val Lys Leu Lys Val Pro Gly Glu Thr Gln Thr Gly Lys Leu Phe Arg
    290                 295                 300

Met Arg Gly Lys Gly Val Lys Ser Val Arg Gly Gly Ala Gln Gly Asp
305                 310                 315                 320

Leu Leu Cys Arg Val Val Glu Thr Pro Val Gly Leu Asn Glu Arg
                325                 330                 335

Gln Lys Gln Leu Leu Gln Glu Leu Gln Glu Ser Phe Gly Gly Pro Thr
            340                 345                 350

Gly Glu His Asn Ser Pro Arg Ser Lys Ser Phe Phe Asp Gly Val Lys
        355                 360                 365

Lys Phe Phe Asp Asp Leu Thr Arg
    370                 375

<210> SEQ ID NO 33
<211> LENGTH: 538
<212> TYPE: PRT
<213> ORGANISM: Mycobacterium tuberculosis hsp60

<400> SEQUENCE: 33

Met Ala Lys Thr Ile Ala Tyr Asp Glu Glu Ala Arg Arg Gly Leu Glu
1               5                   10                  15

Arg Gly Leu Asn Ala Leu Ala Asp Ala Val Lys Val Thr Leu Gly Pro
            20                  25                  30

Lys Gly Arg Asn Val Val Leu Glu Lys Lys Trp Gly Ala Pro Thr Ile
        35                  40                  45

Thr Asn Asp Gly Val Ser Ile Ala Lys Glu Ile Leu Glu Asp Pro
    50                  55                  60

Tyr Glu Lys Ile Gly Ala Glu Leu Val Lys Glu Val Ala Lys Lys Thr
65                  70                  75                  80

Asp Asp Val Ala Gly Asp Gly Thr Thr Thr Ala Thr Val Leu Ala Gln
                85                  90                  95

Ala Leu Val Arg Glu Gly Leu Arg Asn Val Ala Ala Gly Ala Asn Pro

-continued

```
                    100                 105                 110
Leu Gly Leu Lys Arg Gly Ile Glu Lys Ala Val Glu Lys Val Thr Glu
            115                 120                 125

Thr Leu Leu Lys Gly Ala Lys Glu Val Glu Thr Lys Glu Gln Ile Ala
130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                    165                 170                 175

Glu Ser Asn Thr Phe Gly Leu Gln Leu Glu Leu Thr Gly Met Arg
            180                 185                 190

Phe Asp Lys Gly Tyr Ile Ser Gly Tyr Phe Val Thr Asp Pro Glu Gln
            195                 200                 205

Glu Ala Val Leu Glu Asp Pro Tyr Ile Leu Leu Val Ser Ser Lys Val
            210                 215                 220

Ser Thr Val Lys Asp Leu Leu Pro Leu Leu Glu Lys Val Ile Gly Ala
225                 230                 235                 240

Gly Lys Pro Leu Leu Ile Ile Ala Glu Asp Val Glu Gly Glu Ala Leu
                    245                 250                 255

Ser Thr Leu Val Val Asn Lys Ile Arg Gly Thr Phe Lys Ser Val Ala
            260                 265                 270

Val Lys Ala Pro Gly Phe Gly Asp Arg Arg Lys Ala Met Leu Gln Asp
            275                 280                 285

Met Ala Ile Leu Thr Gly Gly Gln Val Ile Ser Glu Glu Val Gly Leu
290                 295                 300

Thr Leu Glu Asn Ala Asp Leu Ser Leu Leu Gly Lys Ala Arg Lys Val
305                 310                 315                 320

Val Val Thr Lys Asp Glu Thr Thr Ile Val Glu Gly Ala Gly Asp Thr
                    325                 330                 335

Asp Ala Ile Ala Gly Arg Val Ala Gln Ile Arg Gln Glu Ile Glu Asn
            340                 345                 350

Ser Asp Ser Asp Tyr Asp Arg Glu Lys Leu Gln Glu Arg Ala Lys Leu
            355                 360                 365

Ala Gly Gly Val Ala Val Ile Lys Ala Gly Ala Ala Thr Glu Val Glu
            370                 375                 380

Leu Lys Glu Arg Lys His Arg Ile Glu Asp Ala Val Arg Asn Ala Lys
385                 390                 395                 400

Ala Ala Val Glu Glu Gly Ile Val Ala Gly Gly Val Thr Leu Leu
                    405                 410                 415

Gln Ala Ala Pro Thr Leu Asp Glu Leu Lys Leu Glu Gly Asp Glu Ala
            420                 425                 430

Thr Gly Ala Asn Ile Val Lys Val Ala Leu Glu Ala Pro Leu Lys Gln
            435                 440                 445

Ile Ala Phe Asn Ser Gly Leu Glu Pro Gly Val Val Ala Glu Lys Val
            450                 455                 460

Arg Asn Leu Pro Ala Gly His Gly Leu Asn Ala Gln Thr Gly Val Tyr
465                 470                 475                 480

Glu Asp Leu Leu Ala Ala Gly Val Ala Asp Pro Val Lys Val Thr Arg
                    485                 490                 495

Ser Ala Leu Gln Asn Ala Ala Ser Ile Ala Gly Leu Phe Leu Thr Thr
            500                 505                 510

Glu Ala Val Val Ala Asp Lys Pro Glu Lys Glu Lys Ala Ser Val Pro
            515                 520                 525
```

```
Gly Gly Gly Asp Met Gly Gly Met Asp Phe
    530                 535

<210> SEQ ID NO 34
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa unknown amino acid

<400> SEQUENCE: 34

Lys Xaa Val Ala Ala Trp Thr Leu Lys Ala Ala Ala
1               5                   10

<210> SEQ ID NO 35
<211> LENGTH: 12
<212> TYPE: PRT
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa unknown amino acid
<220> FEATURE:
<221> NAME/KEY: misc_feature
<222> LOCATION: (3)..(3)
<223> OTHER INFORMATION: Xaa unknown amino acid

<400> SEQUENCE: 35

Xaa Ala Xaa Ala Ala Ala Ala Thr Leu Lys Ala Ala
1               5                   10

<210> SEQ ID NO 36
<211> LENGTH: 21
<212> TYPE: DNA
<213> ORGANISM: Artificial sequence
<220> FEATURE:
<223> OTHER INFORMATION: Primer

<400> SEQUENCE: 36
ccaacgcaaa gcaatacatg a                                              21

<210> SEQ ID NO 37
<211> LENGTH: 22
<212> TYPE: DNA
<213> ORGANISM: Artificial sequence
<220> FEATURE:
<223> OTHER INFORMATION: Primer

<400> SEQUENCE: 37
ttttcgcttc cctgttttag ct                                             22

<210> SEQ ID NO 38
<211> LENGTH: 25
<212> TYPE: DNA
<213> ORGANISM: Artificial sequence
<220> FEATURE:
<223> OTHER INFORMATION: Probe

<400> SEQUENCE: 38
tccaagtgat ggctgaactg tcgcc                                          25
```

```
<210> SEQ ID NO 39
<211> LENGTH: 21
<212> TYPE: DNA
<213> ORGANISM: Artificial sequence
<220> FEATURE:
<223> OTHER INFORMATION: Primer

<400> SEQUENCE: 39
tgagaacagc tgcacccact t                                              21

<210> SEQ ID NO 40
<211> LENGTH: 20
<212> TYPE: DNA
<213> ORGANISM: Artificial sequence
<220> FEATURE:
<223> OTHER INFORMATION: Primer

<400> SEQUENCE: 40
gctgaaggca tctcggagat                                                20

<210> SEQ ID NO 41
<211> LENGTH: 26
<212> TYPE: DNA
<213> ORGANISM: Artificial sequence
<220> FEATURE:
<223> OTHER INFORMATION: Probe

<400> SEQUENCE: 41
caggcaacct gcctaacatg cttcga                                         26

<210> SEQ ID NO 42
<211> LENGTH: 19
<212> TYPE: DNA
<213> ORGANISM: Artificial sequence
<220> FEATURE:
<223> OTHER INFORMATION: Primer

<400> SEQUENCE: 42
tcacctacgc cacgctcat                                                 19

<210> SEQ ID NO 43
<211> LENGTH: 20
<212> TYPE: DNA
<213> ORGANISM: Artificial sequence
<220> FEATURE:
<223> OTHER INFORMATION: Primer

<400> SEQUENCE: 43
tcattgagtg tccgctgctt                                                20

<210> SEQ ID NO 44
<211> LENGTH: 21
<212> TYPE: DNA
<213> ORGANISM: Artificial sequence
<220> FEATURE:
<223> OTHER INFORMATION: Probe

<400> SEQUENCE: 44
tgggccatcc tggaggctcc a                                              21

<210> SEQ ID NO 45
<211> LENGTH: 18
<212> TYPE: DNA
<213> ORGANISM: Artificial sequence
<220> FEATURE:
<223> OTHER INFORMATION: Primer
```

```
<400> SEQUENCE: 45
ccacccatgg caaattcc                                                      18

<210> SEQ ID NO 46
<211> LENGTH: 22
<212> TYPE: DNA
<213> ORGANISM: Artificial sequence
<220> FEATURE:
<223> OTHER INFORMATION: Primer

<400> SEQUENCE: 46
tgggatttcc attgatgaca ag                                                 22

<210> SEQ ID NO 47
<211> LENGTH: 23
<212> TYPE: DNA
<213> ORGANISM: Artificial sequence
<220> FEATURE:
<223> OTHER INFORMATION: Probe

<400> SEQUENCE: 47
tggcaccgtc aaggctgaga acg                                                23
```

STRESS PROTEINS AND PEPTIDES AND METHODS OF USE THEREOF

CROSS REFERENCE TO RELATED APPLICATION(S)

This invention is a continuation-in-part of and claims priority under 35 U.S.C. § 120 to U.S. Ser. No. 09/828,574, filed Apr. 6, 2001, issued as U.S. Pat. No. 6,989,146, which claims priority under 35 U.S.C. § 119(e) to provisional application Ser. No. 60/224,104, filed Aug. 9, 2000; and is a continuation-in-part of and claims priority under 35 U.S.C. § 120 to U.S. Ser. No. 10/490,949, filed Mar. 25, 2004, which is a 35 U.S.C. § 371 National Stage application of PCT application serial number PCT/US02/30578, filed Sep. 25, 2002, both of which claim priority under 35 U.S.C. § 119(e) to provisional application Ser. No. 60/339,284, filed Dec. 11, 2001, and to provisional application Ser. No. 60/325,499, Sep. 25, 2001, the contents of each of which are hereby incorporated by reference in their entirety.

FIELD OF THE INVENTION

This invention relates to novel stress-related peptides and methods of use thereof. In particular, there is provided novel heat shock protein (hsp) peptide sequences useful in modulating inflammatory responses in immune-mediated diseases, ranging from autoimmunity to cancer to infectious diseases. Even more particularly, this invention relates to the

BACKGROUND INFORMATION

Vertebrates possess the ability to mount an immune response as a defense against pathogens from the environment as well as against aberrant cells, such as tumor cells, which develop internally. This can take the form of innate immunity, which is mediated by NK cells, neutrophils, and cells of the monocyte/macrophage lineage, or the form of acquired or active immunity against specific antigens, which is mediated by lymphocytes. Active immune responses can be further subdivided into two arms, the humoral response, which entails the production of specific antibodies that serve to neutralize antigens exposed to the systemic circulation and aid in their uptake by professional phagocytic cells, and the cellular arm, which is responsible for the recognition of infected or aberrant cells within the body. Often these immunogenic responses result in diseases and disorders that cause harm to the organism itself. Such disorders are associated with the recognition of self proteins and cells as foreign, and thus trigger an attack upon such cells or self proteins. Common autoimmune disorders include, for example, psoriasis, arthritis, lupus, diabetes, and other medical conditions known in the art.

One of most likely scenarios regarding the pathogenesis of an autoimmune disease such as type I diabetes or multiple sclerosis (MS), for example, may begin with abnormal regulation of autoreactive T cells either due to bystander activation or due to molecular mimicry. For example, a viral infection or exposure to a superantigen may provide sufficient co-stimulation resulting in activation of a few low affinity autoreactive T cells that escape selection in the thymus. Abnormal down-regulation of such autoreactive responses may lead to expansion of pathogenic T cells that infiltrate the organ where the recognized antigen is present. A few host-related factors facilitate the transition between non-pathogenic autoreactivity and autoimmune disease: leaky central negative selection allowing the escape of higher numbers of autoreactive precursors; impaired peripheral tolerance due to abnormalities involving receptors or ligands that mediate down-regulation of lymphocyte activity; a bias to generate TH1 pro-inflammatory responses as opposed to more balanced TH1/TH2 responses; and high frequency and abnormal activity of professional antigen presenting cells (APCs).

Local inflammation and direct destruction of host cells trigger antigen release, uptake by professional APCs, and presentation to specific T cells, thereby perpetuating a positive feed-back that exacerbates the autoimmunity. Simultaneously, normally cryptic, organ-associated antigens may become exposed in the context of activation of professional antigen presenting cells and antigen release, resulting in activation of T cells specific for these other self antigens. Particularly in conditions favoring overall TH1/TH2 imbalance, the employment of additional specificities may accelerate the disease. It is widely believed that whereas TH1 cytokines contribute to the pathogenesis of autoimmunity, TH2 cytokines, on the other hand, may suppress the activity of pathogenic TH1 or Tc1 cells.

Heat shock proteins (hsps) are highly conserved proteins that play an important role in various cellular processes. Hsps are stress proteins that are typically upregulated during cellular stress. Apart from that, it has been shown that hsps are immunodominant. Unique qualities of hsps (e.g., evolutionary conservation, immunodominance, and upregulation during stress) have made hsps attractive candidates as targets for immunotherapy and vaccines. Indeed, at present, the role of immune reactivity to hsps has been proposed in different disease models, varying from cancer to infectious diseases and autoimmune diseases.

Most evidence for the role of hsps in the immune regulation of inflammatory diseases comes from models of chronic arthritis. This research has shown that immunization with hsp10, hsp60, and hsp70 can all confer protection in virtually all models of experimental arthritis. In the model of adjuvant arthritis, immune reactivity to hsps plays a role both in the induction of disease and in protection from disease. For example, on one hand, it was shown that adjuvant arthritis can be induced by means of a T cell clone, called A2b, that is specific for mycobacterial hsp60 180-188 peptide, while on the other hand, later studies showed that preimmunization with mycobacterial hsp60 can effectively protect against disease induction. However, after immunization with hsp60 several epitopes were found to be recognized by the immune system. Interestingly, only one epitope (i.e., a peptide made up of mycobacterial hsp60 residues 256-270) out of eight epitopes was found to be capable to induce protection. This protection was based on the induction of (self-hsp) cross-reactive T cells. Thus there arose a picture from the data of the animal model of adjuvant arthritis for an important role for immune reactivity against hsps in the regulation of arthritis, both in protection and in disease induction. The fact that different epitopes had completely opposite effects underlined the importance of also defining peptide T cell epitopes in the human system.

Over the last 10 years it has become clear that immune reactivity to hsps also plays a crucial role in human chronic arthritis, namely Juvenile Idiopathic Arthritis (JIA) and Rheumatoid Arthritis (RA). First, increased expression of hsp60 was detected in synovial lining cells of subjects with JIA and RA. Secondly, T cell reactivity to both self and non-self hsp60 was found in both diseases. Similarly, immune reactivity to other hsps such as hsp70 and DnaJ was detected in subjects with JIA and RA. In children with JIA, immune reactivity to self-hsp60 seemed predictive of a favorable prognosis.

SUMMARY OF THE INVENTION

The present invention advances the art of immune modulation by providing substantially pure HLA pan DR-binding peptides comprising a fragment of a heat shock protein (hsp) that is capable of binding to MHC class II molecules. Such peptides provide a way in which T cells can be up- or down-regulated with respect to certain T cell responses, particularly responses associated with a TH-1 to TH-2 or a TH2 to a TH-1 transition. Accordingly, one aspect of the invention concerns such compositions comprising such peptides in substantially pure form, including pharmaceutical compositions.

In another aspect, the peptides of the invention are used to modulate T cells in an antigen-specific manner so as to lead to control of autoimmune inflammation for specific antigens associated with induction of disease states. Such methods can be preventive or for treatment. Relatedly, control of autoimmune inflammation is carried out by modulation of the immune response wherein T cells are either activated to bring about a TH-1 response (i.e., a stimulating response wherein pro-inflammatory cytokines are induced, such as TNFα, INFγ, IL-1, IL-2, IL-6, IL-12, IL-16, and IL-17), or T cells that have a regulatory function are induced to bring about either a TH2 or TH3 response (i.e., a regulatory response wherein anti-inflammatory cytokines are induced, such as TGFβ, IL-4 and IL-10, and sometimes IFNγ). Bringing about a regulatory response can also be understood as inducing a reduction, or "dimming," of pro-inflammatory responses. In the context of this invention, this is accomplished by administration of peptides according to the invention whose amino acid sequences are (or are derived from) epitopes of heat-shock proteins associated with the pro-inflammatory response. Such dimming is the result of inducing tolerization to such epitopes. In some embodiments, the peptides of the present invention induce regulatory T cell modulation by acting as molecular dimmers for reducing or reversing pro-inflammatory responses by, for example, (1) direct induction of regulatory T cells by active immunity, which immunity can occur via, for example, subcutaneous injection, and (2) mucosal administration of the peptide which alters the quality of the T cell response from pro-inflammatory to a regulatory response due to altering T cell functional phenotype, and even more particularly by modulating the regulatory phenotype of regulatory T cells and/or inducing emergence of T cells with a different functional phenotype. In one embodiment of the invention, the methods of the invention are used for treating or preventing an immune-mediated disease in a subject having, or at risk of having, such a disease e.g., including, but not limited to, juvenile idiopathic arthritis (JIA), rheumatoid arthritis (RA), psoriatic arthritis (PA), osteoarthritis (OA), inflammatory bowel disease (IBD), multiple sclerosis (MS), psoriasis, allergy and atherosclerosis and dermato myositis (DM). In such methods, treatment involves administrating to the subject an effective amount of a substantially pure peptide comprising a fragment of a heatshock protein that binds to one or more MHC class II molecules in a pharmaceutically acceptable carrier, wherein the peptide modulates an immune response, thereby treating or preventing the disease.

In still a further embodiment, peptides are derived from heat shock proteins that are other than those which possess sequence identity, in whole or in part, with certain bacterial hsp60 peptide motifs recognized as being associated with an inflammatory response. Such other peptides, themselves not recognized as being capable of stimulating an inflammatory response, can be, used to induce regulatory cytokines for modulation of inflammatory responses. In the context of this disclosure, such peptides are termed "nonhomologous" peptides.

In yet another aspect, the present invention provides isolated nucleic acid sequences encoding the peptides of the invention. In one embodiment such nucleic acids are included in an expression vector capable of directing the expression of the peptide in the particular expression system employed, be it an in vitro expression system or an in vivo expression system. In one embodiment in vivo expression systems utilized are recombinant expression systems that employ suitable host cells into which an expression vector according to the invention has been inserted. As will be appreciated, any suitable expression system can be adapted to make the peptides of the invention. Alternatively, the peptides of the invention can be synthesized by any suitable chemistry, including solution chemistries.

BRIEF DESCRIPTION OF THE DRAWINGS

FIG. 1 depicts the amino acid sequence of *E. coli* K12 hsp60 protein (SEQ ID NO: 1).

FIG. 2 depicts the amino acid sequence of human hsp60 protein (SEQ ID NO: 13).

FIG. 3 depicts the amino acid sequence of *E. coli* (heat-shock protein) dnaJ (SEQ ID No: 32).

FIG. 4 depicts the amino acid sequence of *Mycobacterium tuberculosis* hsp60 (SEQ ID No: 33).

FIGS. 11A-E includes a series of graphs showing treatment-induced modulation of T cell responses to dnaJP1. FIG. 11A shows T cell proliferative responses: PBMC from patients (n=7) were stimulated for 5 days with 10 μg/ml of dnaJP1 peptide. Evaluation was performed at monthly intervals. Controls include PHA as a general mitogen and dnaJpV. FIGS. 11B-E show evaluation by FACS at monthly intervals of production of intracellular cytokine (pro inflammatory: FIGS. 11B-D; tolerogenic: FIG. 11E) by PBMC of the patients who were responsive at the screening to dnaJP1 peptide. FIG. 11B: IL-2, n=6; FIG. 11C: IFN-γ, n=8; FIG. 11D: TNF-α, n=6; FIG. 11E: Il-4 and IL-10, n=4. Results are expressed as % CD3+ cells in dnaJP1 stimulated-unstimulated cultures (*=p.<0.05).

FIGS. 12B-E comprise graphs showing tender and swollen joint data. FIGS. 12D and 12E show the number of tender joints and the number of swollen joints in said subjects, respectively. Measurements are taken at monthly intervals (*=p.<0.05).

In FIG. 13A, Stimulation Index (SI) (y-axis). X axis shows the hsp60 proteins and peptides thereof, mhsp60 is whole mycobacterial hsp60; hhsp60 is whole human hsp60. P1-8 are the peptides shown in FIG. 5. The dots represent individual patients. Lines indicate median values. FIG. 13B shows a disease specificity study in which T cell proliferation was stimulated by the peptides in a RA patient population and compared with samples from osteoarthritis (OA) patients and healthy controls.

In FIG. 18A, biopsies were taken from normal and affected tissue and scored using standard histology analysis protocols. FIGS. B-G show cytokine profiles of patients divided into three groups (i.e., controls and those with either Crohn's Disease or those with Ulcerative Colitis (UC)) and assessed by quantitative PCR (taqman) from biopsies taken from normal and abnormal areas as indicated in FIG. 18A, each stimulated with bacterial and human peptide pools. ("Bacterial N" indicates sample is from normal tissue and stimulated with bacterial peptides, "Bacterial A" is from abnormal tissue and stimulated with bacterial peptides, "Human N" indicates normal tissue stimulated with human peptides and "Human A" indicates abnormal tissue stimulated with human peptides), Sample split up between controls (n=4) and Crohn's Disease, Ulcerative Colitis (n=6) samples. Tbet is a transcription factor upstream of a pathway that controls TH1 responses. Gata-3 is a transcription factor that controls downstream events relating to TH2, TH3-type responses.

FIG. 19A-C shows a correlation between the response to the human and microbial epitopes. The proliferative response to mycobacterial peptide is correlated with respect to its human counterpart variant. FIG. 19A: Human hsp60 vs. Mycobacterial hsp60, FIG. 19B: Mycobacterial peptide p1 vs. human peptide p2, and FIG. 19C: Mycobacterial peptide (residues 256-270) vs. human peptide (residues 282-296). Each dot represents one patient. The graphs are expressed as stimulation indices FIG. 20A-L Treatment-induced modulation of T cell responses to dnaJP1. PBMC immune responses to dnaJP and controls from patients enrolled in the trial (n=15). T cell-proliferative response after in vitro culture with dnaJP1(a) or an irrelevant altered peptide ligand (b) in a standard proliferation assay. Phytohemagglutinin (a, ▲) was used as a positive control for T cell proliferation. They axis shows the stimulation index: the mean cpm in antigen-stimulated cultures divided by the mean cpm in nonstimulated cultures. *, P<0.001. Intracellular production of IL-2, IFN-γ, and TNF-α in response to dnaJP1 (c, e, and g) or PADRE peptide (d-f and h, respectively) at day 0 assessed at monthly intervals during treatment. Cytokine production is expressed as the percentage of CD3/cytokine double-positive cells measured by FACS in antigen-stimulated cultures, nonstimulated cultures (y axis). Error bars represent SD of the mean. Intracellular production of IL-4 (i) and IL-10 (k) after in vitro culture with dnaJP1 or with PADRE (j and l) at days 0, 56, and 168 of the treatment period.

DETAILED DESCRIPTION OF THE INVENTION

Figure 5:
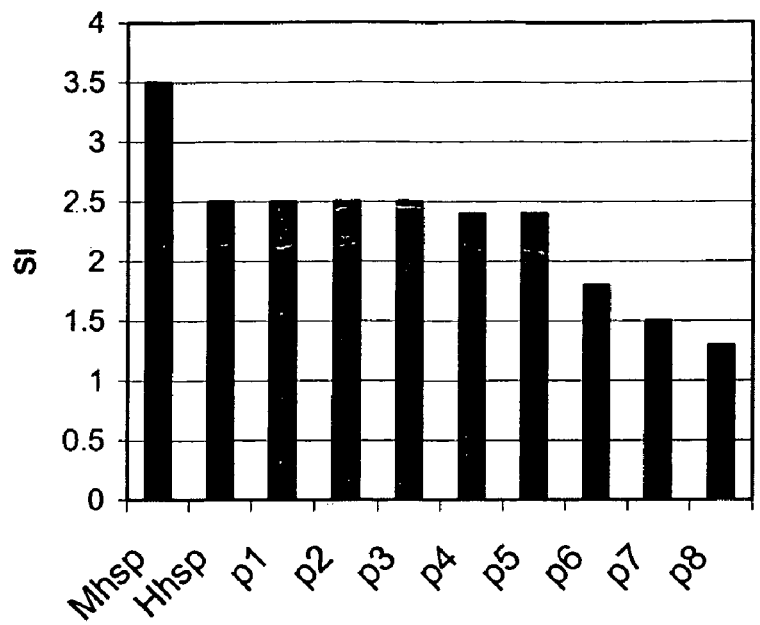
FIG. 5 shows the T cell proliferative response to pan DR binding hsp60 peptides in cells from 80 subjects with Juvenile Idiopathic Arthritis (JIA). On the Y-axis is shown the Stimulation Index (SI), which is defined as the mean counts per minute (CPM) in wells with cells cultured with antigens divided by the mean cpm in wells cultured with medium alone. The X-axis shows the different antigens tested in the assay: (from left to right) whole mycobacterial hsp60 (Mhsp, SEQ ID NO: 33), whole human hsp60 (Hhsp60, SEQ ID NO: 13), p1 (residues 254-268 of *M. tub.* hsp60, SEQ ID NO: 2), p2 (residues 280-294 of human hsp60, SEQ ID NO: 3), p3 (residues 216-230 of *M. tub.* hsp60, SEQ ID NO: 4), p4 (residues 242-256 of human hsp60, SEQ ID NO: 5), p5 (residues 210-224 of *M. tub.* hsp60, SEQ ID NO: 6), p6 (residues 236-250 of human hsp60, SEQ ID NO: 7), p7 (residues 507-521 of *M. tub.* hsp60, SEQ ID NO: 8), and p8 (residues 535-549 of human hsp60, SEQ ID NO: 9).

In a first embodiment, the current invention provides for methods by which immune responses in a mammal are modified by either increasing stimulation of T cells, or modulating T cell response by inducing a regulatory T cell response, also termed "dimming down" the proinflammatory T cell responses. In a related aspect, dimming down proinflammatory responses is carried out by mucosal administration of certain peptides derived from either bacterial or mammalian hsp60.

The present invention also provides novel peptide sequences that modulate T cell responsiveness due to the promiscuous binding and presentation of the peptides with a variety of MHC molecules. In one embodiment, increased presentation of the peptides of the present invention results in an increased likelihood of immunological recognition and thus such peptides are ideal candidates for molecules that modulate immune response, such as vaccines and modulators of inflammatory reactions in which the immune response is down-regulated or "dimmed", as well as cancer and infectious disease therapeutics in which the immune response is upregulated to augment the body's attack upon the aberrant cells.

The contradictory role of different epitopes of mycobacterial hsp60 in adjuvant arthritis made it imperative to discover peptide T-cell epitopes of hsp60 in subjects with JIA and RA. Based on the data gathered in the animal models, various attempts were made to identify T cell epitopes in subjects with JIA. However, predictions on potential epitopes, based on data from the model of adjuvant arthritis, proved ineffective for the identifications of T cell epitopes in the human system. Especially in the case of JIA, the heterogenic HLA background of subjects with JIA hampered the prediction of potential T cell epitopes of hsp60. This made prediction based on MHC binding assays impossible and prediction based on theoretical optimal binding to DR4 of little, if any, value. For example, mere frame shifts in peptide sequences of hsp60, or analogues thereof, have proven to exhibit dramatic differences in activity regarding stimulating or dimming T cell response.

The present invention identifies promiscuous pan-DR T cell epitopes. These peptides fit in various different MHC molecules, especially MHC class II molecules, and thus are recognized by T cells in the vast majority of subjects. To identify the promiscuous pan-DR peptides, a computer algorithm described in U.S. Pat. No. 6,037,135 (incorporated herein by reference in its entirety) that identifies motifs for binding of peptides to various MHC class II molecules, was used. Sequences of mycobacterial, *E. coli*, and human hsp60 were scanned and based on the predicted binding of peptide sequences to three subtypes of HLADR, namely DR1, DR4 and DR7, candidate peptides were designed (Table 1). The peptides were selected on the level of predicted binding to DR1, DR4 and DR7. The peptides of the present invention, including those listed in Table 1, have been identified in in vitro tests as having the ability to induce the proliferation of autoreactive T cells or to induce the secretion of cytokines (e.g., lymphokines) from these T cells or to induce other effector functions such as cytotoxicity. Certain of such peptides have also been identified as having the ability to induce a dimming down of a proliferative T cell response if properly administered to a patient's immune system.

As discussed above, hsps are targets for the immune system during immune-mediated chronic inflammation. More specifically, immune modulation using human, *E. coli*, and mycobacterial hsp peptide motifs based upon experimental models can provide novel therapeutics for diseases such as diabetes, IBD, RA, psoriatic arthritis, MS, dermato myositis, and transplantation related diseases such as graft versus host disease.

In the present invention, T cell-mediated events relevant to autoimmunity are driven by several different antigens, which have at least one, however in one embodiment have all, of the following characteristics in order to be candidates as immunomodulatory agents:

i) be part of proteins with documented strong antigenic potential;

ii) induce production of cytokines with either stimulating or regulatory function in inflammation;

iii) be part of proteins which occur at and are possibly overexpressed at the site of inflammation;

iv) be possibly part of proteins which contain domains conserved across species. This latter characteristic would be important in the context of abnormalities in immune regulation induced by cross reactive recognition (i.e., molecular mimicry).

Accordingly, the present invention provides novel peptides that can be used to modulate, block, or inhibit inflammatory responses by altering T cell functional phenotype, and even more particularly by modulating the regulatory phenotype of regulatory T cells and/or inducing emergence of T cells with a different functional phenotype. The peptides and methods are useful for (1) screening peptides or peptide analogs that modulate (i.e., either down-regulate, up-regulate, or shift the ratio of TH 1:TH2 molecules produced) a pathogenic immune response; (2) monitoring efficacy or therapeutic use of such peptides; and (3) to identify other agents that may be effective to down-regulate or inhibit an immune response in treatment of, for example, chronic inflammatory conditions. For example, in patients treated with dnaJP1, there is a reduced joint tenderness and swelling as shown in FIGS. 11A-D.

Hsps are also targets for the immune system during immune-mediated cancerous conditions and pathogenic infections. Using hsp-derived peptides can provide novel therapeutics for such cancerous conditions as melanoma, leukemia, lymphoma, solid tumors (lung, liver, kidney, brain, bladder), retinoblastoma, sarcomas and other connective tissue cancers, and the like. Immune-mediated pathogenic infections that can be treated using the HLA pan DR peptides include such immune-mediated microbial infections as tuberculosis, leprosis, bacterial infections of Gram positive and Gram negative microorganisms, HIV/AIDS, Epstein Barr Virus, and Cytomegalovirus infections, and protozoan infections, such as Leishmania, and the like.

In one embodiment, the invention relates to peptides and methods of using them to up-regulate the body's immune response so as to modulate, block, or inhibit precancerous or cancerous conditions and microbial infections. These and the other peptides and methods of the invention are useful for screening peptides or peptide analogs that up regulate the body's immune response so as to counteract the progression of a cancerous condition or microbial infection; to monitor efficacy or therapeutic use of such peptides; and to identify other agents that may be effective to up-regulate or modulate an immune response in treatment of such immune-mediated precancerous or cancerous conditions and microbial infections.

The substantially pure HLA pan DR-binding peptides of the invention comprise fragments of stress proteins that bind to an MHC class II molecule, for example, HLADR1, DR4 and DR7. These peptides can be derived, for example, from mycobacterial heat shock proteins (mhsp60), human heat shock proteins (hsp60), and E. coli heatshock proteins (ehsp60).

Vertebrates possess the ability to mount an immune response as a defense against pathogens from the environment as well as against aberrant cells, such as tumor cells, which develop internally. This can take the form of innate immunity, which is mediated by NK cells, neutrophils, and cells of the monocyte/macrophage lineage, or the form of acquired or active immunity against specific antigens mediated by lymphocytes. Active immune responses can be further subdivided into two arms, the humoral response which entails the production of specific antibodies that serve to neutralize antigens exposed to the systemic circulation and aid in their uptake by professional phagocytic cells, and the cellular arm which is required for recognition of infected or aberrant cells within the body.

In both cases, the specific response is regulated by the intracellular processing and recognition of the antigen by effector T-cells. Mature cytolytic T lymphocytes (CTLs) and T helper cells (Th) remain in a resting state unless they encounter antigens that their receptors can recognize in the context of MHC class I or II molecules. Upon encountering the specific antigens, the T cells proliferate and perform effector functions, the intended result of which is elimination of the reactive antigens. When the antigen is processed through the cytoplasmic route, the resultant peptides are bound to nascent MHC class I molecules that facilitate appropriate presentation to effector T cells. MHC class I presentation favors recognition by cytotoxic T lymphocytes (CTLs) that carry the CD8 ligand. In contrast, intracellular processing via the endocytic route results in presentation on MHC class II molecules, which mode of processing favors T helper responses involved in stimulation of the humoral arm. The goal of vaccination is to prime both responses and generate memory T cells, such that the immune system is primed to react to a recurrent pathogenic infection.

Activation of the T cells entails the generation of a series of chemical signals (primarily cytokines) that result in direct action or stimulating other cells of the immune system to act. In the case of activation by class I MHC-antigen, CTLs proliferate and act to destroy infected cells presenting that given antigen. Killing an infected cell prevents, for example, a virus from proliferating and makes it accessible to neutralizing antibodies, hence permitting elimination of the virus. In contrast, activation of Th cells by class II MHC-antigen complexes does not destroy the antigen presenting cell (which is part of the host's defense system) but rather stimulates the Th cell to proliferate and generate signals (again primarily cytokines) that affect various cells. Among other consequences, the signaling leads to B cell stimulation, macrophage activation, CTL differentiation, and promotion of inflammation. This concerted response is relatively specific and is usually directed to foreign elements bearing the peptide presented by the class II MHC system.

When operating properly the immune response is surprisingly effective at eliminating pathogenic microbes (e.g., pathogenic bacteria, fungi, and viruses) and, to a lesser extent, neoplastic cells. In general, the complicated mechanisms for self-recognition are efficient and allow a strong response to be directed exclusively at foreign antigens. The regulation of self/non-self discrimination, which is a critical function of the immune system, involves multiple mechanisms during the development and life-span of T and B lymphocytes. Whereas deletion of self-reactive T and B cell precursors in the central lymphoid organs eliminates most of autoreactive cells, the peripheral mechanisms that require Fas, IL-2R, and CTLA-4 mediated signaling are thought to be crucial for immune homeostasis. Unfortunately, the immune system occasionally malfunctions and turns against the cells of the host, thereby provoking an autoimmune response. Autoimmunity or autoreactivity typically occurs when antigen receptors on immune cells recognize specific self-antigens (e.g., self-epitopes) on host cells and initiate reactions that result in the destruction of the host cells. In many cases, autoimmune reactions are self-limited in that they disappear when the antigens that provoked them are cleared away. However, in some instances the autoreactive lymphocytes survive longer than they should and continue to induce apoptosis or otherwise eliminate host cells. Examples of autoimmune disorders or conditions include multiple sclerosis (MS), rheumatoid arthritis (possibly more than one mechanism), psoriatic arthritis, juvenile arthritis, lupus erythrematosis, inflammatory bowel disease, and type I diabetes.

Recent developments, in particular the identification of allele-specific peptide binding motifs, have transformed the field (Madden et al., 1991; Rotschke and Falk, 1991). Based on this knowledge, the structural basis for MHC linked susceptibility to autoimmune diseases can be reassessed at a level of detail sufficient for solving longstanding questions in the field. Motifs for peptide binding to several MHC class I and class II molecules have been defined by sequence analysis of naturally processed peptides and by mutational analysis of known epitopes. MHC class I bound peptides were found to be short (generally 8-10 amino acids long) and to possess two dominant MHC anchor residues; MHC class II bound peptides were found to be longer and more heterogeneous in size (Madden et al., 1991; Rotschke & Falk, 1991; Jardetzky et al. 1991; Chicz et al. 1993). More recently, a crystal structure for HLA-DR1 demonstrated that there is a dominant hydrophobic anchor residue close to the N-terminus of the peptide and that secondary anchor residues are found at several other peptide positions (Brown et al., 1993).

Heat shock proteins, which are included in the class known as stress proteins, useful in the practice of the instant invention can be selected from among any cellular protein that satisfies any one or more of the following criteria. A heat shock protein is characterized by having its intracellular concentration increase when a cell is exposed to a stressful stimuli (e.g., heat, cold, light, nutrient limitation, radiation, alteration of pH, etc.), by being capable of binding other proteins or peptides, by being capable of releasing the bound proteins or peptides in the presence of adenosine triphosphate (ATP) or low pH, or by having at least 35% homology with any cellular protein having any of the above properties.

To date, three major families of hsps have been identified based on molecular weight. The families have been called hsp60, hsp70, and hsp90, where the numbers reflect the approximate molecular weight of the stress proteins in kilodaltons. Mammalian hsp90 and gp96 each are members of the hsp90 family. Many members of these families were found subsequently to be induced in response to other stressful stimuli including, but not limited to, nutrient deprivation, metabolic disruption, oxygen radicals, and infection with intracellular pathogens. (See Welch, May 1993, *Scientific American* 56-64; Young, 1990, *Annu. Rev. Immunol.* 8:401-420; Craig, 1993, *Science* 260:19021903; Gething, et al., 1992, *Nature* 355:33-45; and Lindquist, et al., 1988, *Annu. Rev. Genetics* 22:631-677), the disclosures of which are incorporated herein by reference. It is contemplated that hsps/ stress proteins belonging to all of these three families can be used in the practice of the instant invention. In one embodiment, an hsp60 protein and protein sequence are used to derive the peptides of the invention. Hsp60 proteins are abundant at normal temperatures in most, but not all, mammalian cells and are further induced by heat (Lai, et al., 1984, *Mol. Cell. Biol.* 4:2802-10; van Bergen en Henegouwen, et al., 1987, *Genes Dev.* 1:525-31).

Heat shock proteins are highly conserved proteins. For example, the hsp60 and hsp90 families show high levels of intrafamily conservation. In addition, it has been discovered that the hsp60, hsp70, and hsp90 families are composed of proteins that are related to the stress proteins in sequence, for example, having greater than 35% amino acid identity, but whose expression levels are not altered by stress. Therefore, it is contemplated that the definition of stress protein, as used herein, embraces other proteins, muteins, analogs, and variants thereof having at least 35%, at least about 55%, or at least about 75% to 85% amino acid identity with members of the three families whose expression levels in a cell are enhanced in response to a stressful stimulus. (See U.S. Pat. No. 5,961,979, which is incorporated herein by reference in its entirety.) The purification of stress proteins belonging to these three families is described below.

In one embodiment, the hsp used in accordance with the invention is a mammalian hsp. In another embodiment, the hsp used in accordance with the invention for the treatment of autoimmune disease is a member of the hsp60 family.

The 60 kDa heat shock protein (hsp60) is a stress protein expressible in all of the cells of the body. Nevertheless, healthy individuals manifest a high frequency of autoimmune T cells specific for hsp60 self-epitopes. Normal healthy mice and humans have been shown to have T cells targeted at their self hsp60 antigen (Kaufmann, 1990; Kaufmann et al., 1994; Young, 1989; Cohen, 1992b). However, these autoimmune T cells are also involved in T cell mediated autoimmune diseases: a high concentration of T cells targeted at self hsp60 antigen have been found in the autoimmune lesions of human chronic arthritis (Cohen, 1991; Res et al., 1989; van Eden et al., 1989), multiple sclerosis (Selmaj et al., 1991), experimental autoimmune encephalomyelitis (Selmaj et al., 1991) and adjuvant arthritis (Hogervorst et al., 1992). Anti-hsp60 T-cells have also been shown to play a role in diabetes mellitus in the non-obese diabetic (NOD) mouse model (Elias et al., 1990; Elias et al., 1991; Elias et al., 1994; Elias et al., 1995; Birk et al., 1996a; Birk et al., 1993; Cohen, 1991).

HLA pan DR-binding peptides of the invention have an amino acid sequence that is conserved in the corresponding heat shock proteins between humans and other lower organisms, particularly between human and bacterial (*E. coli*) or human and mycobacterial heat shock proteins, such as hsp60 and dnaJ respectively.

The term "isolated" or "purified" means altered "by the hand of man" from its natural state; i.e., if it occurs in nature, it has been changed or removed from its original environment, or both. For example, a naturally occurring polynucleotide or a polypeptide naturally present in a living animal in its natural state is not "isolated" or "purified", but the same polynucleotide or polypeptide separated from the coexisting materials of its natural state is "isolated" or "purified", as the term is employed herein.

A "substantially pure peptide" is typically pure when it is at least 60%, by weight, free from the proteins and naturally-occurring organic molecules with which it is naturally associated. In one embodiment, the preparation is at least about 75%, in another embodiment, at least about 90%, and in still another embodiment, at least about 99% pure, by weight, and has a sequence which is a fragment of the sequence as set forth in SEQ ID NO: 1, SEQ ID NO: 13, or SEQ ID NO: 33 (e.g., SEQ ID NOS: 2, 3, 4, 5, 6, 7, 8, 9, 10, 24, 25, 26 or 27). A substantially pure hsp60 peptide of the invention may be obtained, for example, by extraction from a natural source, by expression of a recombinant nucleic acid encoding a full-length polypeptide (e.g, SEQ ID NO: 1, SEQ ID NO: 13, or SEQ ID NO: 33), followed by cleavage with a protease; by expression of a recombinant nucleic acid encoding a fragment of SEQ ID NO: 1, SEQ ID NO: 13, or SEQ ID NO: 33 (e.g., SEQ ID NOS: 2, 3, 4, 5, 6, 7, 8, 9, 10, 24, 25, 26 or 27); or by chemically synthesizing the peptides of the invention. Purity can be measured by any appropriate method, e.g., by column chromatography, polyacrylamide gel electrophoresis, or by HPLC analysis.

Heat shock protein-60 (hsp60) peptides of the invention include fragments of the sequences as set forth in SEQ ID NO: 1, SEQ ID NO: 13, or SEQ ID NO: 33. Examples of invention fragments (i.e., peptides) of such hsp60 heat shock proteins include the peptides having the sequences as set forth in Table 1 (P1, 2, 3, 4, 5, 6, 7, 8, 9, 10, 11, 12 (SEQ ID NOS: 2, 3, 4, 5, 6, 7, 8, 9, 24, 25, 26 and 27, respectively). Heat shock protein dnaJ peptides, or peptides of the invention from human and *E. coli*, having amino acid sequences identical or between 75% and 100% sequence identity, include fragments of the sequence as set forth in SEQ ID NO: 32, such as peptides having the sequences of SEQ ID No: 10. Such peptides or polypeptides of the invention can be substantially purified.

TABLE 1

| | Source Hsp60 | | Seq Id No | Sequence | Core epitope/ Seq Id Nos | DR1 score | DR4 score | DR7 score | Pan DR score |
|---|---|---|---|---|---|---|---|---|---|
| P1 | MYC | 254-268 | 2 | GEALSTLVVNKIRGT | LSTLVVNKI/ 14 | 42.37 | 17.03 | 276.91 | 3 |
| P2 | HUM | 280-294 | 3 | GEALSTLVLNRLKVG | LSTLVLNRL/ 15 | 12.46 | .94 | 8.74 | 1 |

TABLE 1-continued

| Source Hsp60 | | Seq Id No | Sequence | Core epitope/ Seq Id Nos | DR1 score | DR4 score | DR7 score | Pan DR score |
|---|---|---|---|---|---|---|---|---|
| P9 | E. COLI | 256-270 | 24 | GEALATLVVNTMRGI | LATLVVNTM/ 28 | | | | |
| P3 | MYC | 216-230 | 4 | PYILLVSSKVSTVKD | LVSSKVSTV/ 16 | 3.59 | 14.29 | 26.68 | 3 |
| | | | | | YILLVSSKV/ 17 | 131.96 | 4.19 | 29.83 | 3 |
| P10 | E. COLI | 218-232 | 25 | PFILLADKKISNIRE | LLADKKISN/ 29 | | | | |
| P4 | HUM | 242-256 | 5 | AYVLLSEKKISSIQS | LSEKKISSI/ 18 | .17 | 2.82 | 7.94 | 1 |
| P5 | MYC | 210-224 | 6 | EAVLEDPYILLVSSK | LEDPYILLV/ 19 | 28.51 | .37 | 15.45 | 2 |
| P11 | E. COLI | 212-226 | 26 | AVELESPFILLADKK | LESPFILLA/ 30 | | | | |
| P6 | HUM | 236-250 | 7 | KCEFQDAYVLLSEKK | FQDAYVLLS/ 20 | 40.82 | 3.63 | 96.80 | 3 |
| P7 | MYC | 507-521 | 8 | IAGLFLTTEAVVADK | LTTEAVVAD/ 21 | 1.76 | .28 | 3.66 | 1 |
| | | | | | FLTTEAVVA/ 22 | 10.51 | 1.28 | 18.65 | 2 |
| P8 | HUM | 535-549 | 9 | VASLLTTAEVVVTEI | LTTAEVVVT/ 23 | 12.03 | 3.34 | 68.00 | 3 |
| P12 | E. COLI | 510-524 | 27 | VAGLMITTECMVTDL | LMITTECMV/ 31 | | | | |

Table 1 shows a set of hsp60 peptides selected on DR binding. The table shows (from left to right) the identification number of the peptide for this disclosure; the origin (human, E. coli, or mycobacterial); the sequence identifier number; the peptide composition; the core epitope; and predicted binding to DR1, DR4, DR7; and the pan DR score. The cut off points for considering an epitope to be a good binder were as follows: DR1~1.570; DR4~2.617, DR7~9.106.

A polypeptide, peptide, or protein refers to a polymer in which the monomers are amino acid residues that are joined together through amide bonds. When the amino acids are alpha-amino acids, either the L-optical isomer or the D-optical isomer can be used, the L-isomers being typical. A peptide of the invention is intended to encompass a fragment of SEQ ID NO: 1, SEQ ID NO: 13, or SEQ ID NO: 33. Specific examples of fragments of SEQ ID NO: 1, SEQ ID NO: 13, or SEQ ID NO: 33 encompassed by the present invention include the sequence as set forth in SEQ ID NOS: 2, 3, 4, 5, 6, 7, 8, 9, 10, 24, 25, 26 and 27 comprised of L- or D-amino acids, and include modified peptides such as by glycosylation, pegylation, as well as dimers or greater multiples of one or more peptides, including peptides of different amino acid composition, wherein the peptide oligomers are covalently linked (for example, by an aliphatic linker attached to the C-terminus of one peptide and the N-terminus of another peptide; by a peptide linker, wherein the peptide linker is not a peptide according to the invention, etc.). Accordingly, the peptides of the invention are intended to cover naturally occurring peptides (but in purified or isolated form), as well as those which are recombinantly or synthetically synthesized. Also encompassed by the present invention are peptides having substantially the same sequence as SEQ ID NOS: 2, 3, 4, 5, 6, 7, 8, 9, 10, 24, 25, 26 and 27 and which peptides retain a functional activity of the sequence to which it is related. Peptides having substantially the same sequence can be designed based upon amino acid substitutions that would still have an approximately 70%-90% sequence identity to the original peptide over the corresponding portion. A yet greater degree of departure in terms of sequence identity is allowed if like-amino acids, i.e. conservative amino acid substitutions, do not count as a change in the sequence. The peptides of the invention are generally between about 8 to about 50 amino acids in length. In one embodiment the peptides of the invention are about 10-30 amino acids in length; in another embodiment they are about 15 amino acids in length; in another embodiment they are about 15-25 amino acids in length; and still another embodiment they are about 15-20 amino acids in length.

A conservative variation or "substitution" denotes the replacement of an amino acid residue by another, biologically similar residue. Examples of conservative variations include the substitution of one hydrophobic residue such as isoleucine, valine, leucine, or methionine for another, or the substitution of one polar residue for another, such as the substitution of arginine for lysine, glutamic for aspartic acid, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine to leucine. The term "conservative variation" also includes the use of a substituted amino acid in place of an unsubstituted parent amino acid provided that antibodies raised to the substituted polypeptide also immunoreact with the unsubstituted polypeptide. In one embodiment a substitution will replace one amino acid with another of at least one of the characteristics of size, charge and polarity.

Modifications and substitutions are not limited to replacement of amino acids. For a variety of purposes, such as increased stability, solubility, or configuration concerns, one skilled in the art will recognize the need to introduce (by deletion, replacement, or addition) other modifications. Examples of such other modifications include incorporation of rare amino acids, dextra-amino acids, glycosylation sites, and cysteine for specific disulfide bridge formation. The modified peptides can be chemically synthesized, or the isolated gene can be mutagenized in a site-specific manner, or a synthetic gene can be synthesized and expressed in bacteria, yeast, baculovirus, tissue culture, and so on.

"Salts" of the hsp60 peptides of the invention contemplated by the invention are physiologically acceptable organic and inorganic salts.

"Functional derivatives" of the hsp60 peptides as used herein covers derivatives which may be prepared from the functional groups which occur as side chains on the residues or the N- or C-terminal groups, by means known in the art, and are included in the invention as long as they remain pharmaceutically acceptable, i.e., they do not destroy the activity of the peptide, do not confer toxic properties on compositions containing it and do not adversely affect the antigenic properties thereof.

These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for examples that of seryl or threonyl residues) formed by reaction with acyl moieties.

Sequencing algorithms can be used to measure sequence identity between known and unknown sequences. Such methods and algorithms are useful in identifying corresponding sequences present in other organisms as well as in the design of peptides of the invention. Sequence identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of identity to various deletions, substitutions, and other modifications. The terms "homology" and "identity" in the context of two or more nucleic acids, polypeptides, or peptide sequences refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 8 to 10, 10 to 20, 20 to 600, usually about 50 to about 200, more usually about 100 to about 150 in which a sequence may be compared to a reference sequence of the same number of contiguous positions after the two sequences are optimally aligned. Methods of alignment of sequence for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol* 48:443 (1970), by the search for similarity method of person & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

One example of a useful algorithm is BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) or 11, an expectation (E) or 10, M=5, N=−4 and a comparison of both strands. For amino acid sequences, the BLASTP program uses as defaults a word length of 3, and expectations (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Natl. Acad. Sci. USA* 90:5873 (1993)). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is, in one embodiment, less than about 0.2, in another embodiment less than about 0.01, and in still another embodiment, less than about 0.001.

Other algorithms for determining homology or identity include, for example, in addition to a BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available online as part of the Human Genome Sequencing Project (J. Roach; Gibbs, 1995). At least twenty-one other genomes have already been sequenced, including, for example, *M. genitalium, M. jannaschii, H. influenzae, E. coli*, and yeast (*S. cerevisiae*), and *D. melanogaster*. The genomes of several model organisms, including mouse, *C. elegans, Arabadopsis thaliana*, and *D. melanogaster*. Several databases containing genomic information annotated with some functional information are maintained by different organization, and are accessible via the internet, for example, hyper text transfer protocol at world wide web address tigr.org/tdb; hyper text transfer protocol at world wide web address genetics.wisc.edu; hyper text transfer protocol genome-www.stanford.edu/~ball; hyper text transfer protocol hiv-web.lanl.gov; hyper text transfer protocol at world wide web address ncbi.nlm.nih.gov; hyper text transfer protocol at world wide web address ebi.ac.uk; and hyper text transfer protocol at world wide web address genome.wi.mit.edu.

In addition to peptides of the invention, nucleic acid sequences (e.g., oligonucleotide or polynucleotide sequences) encoding fragments of SEQ ID NO: 1, SEQ ID NO: 13, or SEQ ID NO: 33 (e.g., SEQ ID NOS: 2, 3, 4, 5, 6, 7, 8, 9, 10, 24, 25, 26 and 27) are encompassed by the present invention. For example, DNA sequences of the invention can be obtained by several methods. For example, the nucleic acid (e.g., DNA or RNA) sequence can be derived for SEQ ID NOS: 2, 3, 4, 5, 6, 7, 8, 9, 10, 12, 24, 25, 26 and 27 based upon the degeneracy of the genetic code and determined using computer based algorithms and sequence programs. There are 20 natural amino acids, most of which are specified by more than one codon. Therefore, all degenerate nucleotide sequences are included in the invention so long as the amino acid sequence of a peptide of the invention encoded by the nucleic acid sequence is functionally unchanged.

Polynucleotide, oligonucleotide, or nucleic acid sequence refers to a polymeric form of nucleotides and are used interchangeably herein. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. In addition, the polynucleotide sequence involved in producing a polypeptide chain can include regions preceding and following the coding region (leader and trailer) as well as intervening sequences (introns) between individual coding segments (exons) depending upon the source of the polynucleotide sequence.

The term polynucleotide(s) generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, the polynucleotides or nucleic acid sequences may contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

The nucleic acid sequence (e.g., an oligonucleotide or a polynucleotide) encoding a peptide of the invention, includes complementary polynucleotide sequences. When the sequence is RNA, the deoxyribonucleotides A, G, C, and T are replaced by ribonucleotides A, G, C, and U, respectively. Also included in the invention are fragments (portions) of the above-described nucleic acid sequences that are at least 15 bases in length, which is sufficient to permit the fragment to selectively hybridize to DNA that encodes a polypeptide or peptide sequence of the invention. "Selective hybridization" as used herein refers to hybridization under moderately stringent or highly stringent physiological conditions (See, for example, the techniques described in Maniatis et al., 1989 *Molecular Cloning A Laboratory Manual*, Cold Spring Harbor Laboratory, N.Y., incorporated herein by reference), which distinguishes related from unrelated nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Screening procedures which rely on nucleic acid hybridization make it possible to isolate any gene sequence from any organism, provided the appropriate probe is available. For example, it is envisioned that such probes can be used to identify other homologs in other organisms. In accomplishing this, alignment algorithms (as described above) can be used to screen genome databases. Alternatively, oligonucleotide probes, which correspond to a part of the sequence encoding the protein in question, can be synthesized chemically. This requires that short, oligopeptide stretches of amino acid sequence must be known (e.g., SEQ ID NOS: 2, 3, 4, 5, 6, 7, 8, 9, 10, 24, 25, 26 and 27). The DNA sequence encoding the protein can be deduced from the genetic code, however, the degeneracy of the code must be taken into account.

In the invention, a nucleic acid sequences encoding SEQ ID NOS: 2, 3, 4, 5, 6, 7, 8, 9, 10, 24, 25, 26 or 27 may be inserted into a recombinant expression vector. The term "recombinant expression vector" refers to a plasmid, virus or other vehicle known in the art that has been manipulated by insertion or incorporation of a nucleic acid sequence encoding SEQ ID NOS: 2, 3, 4, 5, 6, 7, 8, 9, 10, 24, 25, 26 or 27. Such expression vectors contain a promoter sequence which facilitates the efficient transcription of the inserted genetic sequence. The expression vector typically contains an origin of replication, a promoter, as well as specific genes which allow phenotypic selection of a transformed cell(s). Vectors suitable for use in the present invention include those described herein.

Methods, which are well known to those skilled in the art, can be used to construct expression vectors containing sequences encoding, for example, SEQ ID NOS: 2, 3, 4, 5, 6, 7, 8, 9, 10, 24, 25, 26 and 27 and appropriate transcriptional/translational control signals. These methods include in vitro recombinant DNA techniques, synthetic techniques, and in vivo recombination/genetic techniques. (See, for example, the techniques described in Maniatis et al., 1989, *Molecular Cloning A Laboratory Manual*, Cold Spring Harbor Laboratory, N.Y.).

The genetic construct can be designed to provide additional benefits, such as, for example addition of C-terminal or N-terminal amino acid residues that would facilitate purification by trapping on columns or by use of antibodies. All those methodologies are cumulative. The choice as to the method of producing a particular construct can easily be made by one skilled in the art based on practical considerations: size of the desired peptide, availability and cost of starting materials, and the like. All the technologies involved are well established and well known in the art. See, for example, Ausubel et al., *Current Protocols in Molecular Biology*, Volumes 1 and 2 (1987), with supplements, and Maniatis et al., *Molecular Cloning, a Laboratory Manual*, Cold Spring Harbor Laboratory (1989). Yet other technical references are known and easily accessible to one skilled in the art.

Nucleic acid sequences can be created which encode a fusion protein and can be operatively linked to expression control sequences. "Operatively linked" refers to a juxtaposition wherein the components so described are in a relationship permitting them to function in their intended manner. For example, a coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired product. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a peptide or protein-encoding nucleic acid sequence, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the nucleic acid sequence. Both constitutive and inducible promoters, are included in the invention (see e.g., Bitter et al., *Methods in Enzymology* 153:516-544, 1987). For example, when cloning in bacterial systems, inducible promoters such as pL of bacteriophage, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

A nucleic acid sequence of the invention including, for example, a nucleic acid sequence encoding a fusion protein, may be inserted into a recombinant expression vector. A recombinant expression vector generally refers to a plasmid, virus or other vehicle known in the art that has been manipulated by insertion or incorporation of a nucleic acid sequences. For example, a recombinant expression vector of the invention includes a nucleic acid sequence encoding a peptide having, for example, a sequence as set forth in SEQ ID NOS: 2, 3, 4, 5, 6, 7, 8, 9, 10, 24, 25, 26 or 27. The expression vector typically contains an origin of replication, a promoter, as well as specific genes which allow phenotypic selection of the transformed cells. Vectors suitable for use in the invention include, but are not limited to the T7-based expression vector for expression in bacteria (Rosenberg, et al., *Gene* 56:125, 1987), the pMSXND expression vector for expression in mammalian cells (Lee and Nathans, *J. Biol. Chem.* 263:3521, 1988), baculovirus-derived vectors for expression in insect cells, cauliflower mosaic virus, CaMV; tobacco mosaic virus, TMV. The nucleic acid sequences of the invention can also include a localization sequence to direct the indicator to particular cellular sites by fusion to appropriate organellar targeting signals or localized host proteins. For example, a polynucleotide encoding a localization sequence, or signal sequence, can be used as a repressor and thus can be ligated or fused at the 5' terminus of a nucleic acid sequence encoding a peptide of the invention such that the localization or signal peptide is located at the amino terminal end of a resulting encoded fusion polypeptide. The construction of expression vectors and the expression of genes in transfected cells involves the use of molecular cloning techniques also well known in the art. (See, for example, Sambrook et al., *Molecular Cloning—A Laboratory Manual*, Cold Spring Harbor Laboratory, Cold Spring Harbor, N.Y., 1989, and *Current Protocols in Molecular Biology*, M. Ausubel et al., eds., (Current Protocols, a joint venture between Greene Publishing Associates, Inc. and John Wiley & Sons, Inc., most recent Supplement)). These methods include in vitro recombinant DNA techniques, synthetic techniques and in vivo recombination/genetic recombination. (See also, Maniatis, et al., *Molecular Cloning A Laboratory Manual*, Cold Spring Harbor Laboratory, N.Y., 1989).

In yeast, a number of vectors containing constitutive or inducible promoters may be used. For a review see, *Current Protocols in Molecular Biology*, Vol. 2, Ed. Ausubel, et al., Greene Publish. Assoc. & Wiley Interscience, Ch. 13, 1988; Grant, et al., "Expression and Secretion Vectors for Yeast," in *Methods in Enzymology*, Eds. Wu & Grossman, 1987, Acad. Press, N.Y., Vol. 153, pp. 516-544, 1987; Glover, *DNA Cloning*, Vol. II, IRL Press, Wash., D.C., Ch. 3, 1986; and Bitter, "Heterologous Gene Expression in Yeast," *Methods in Enzymology*, Eds. Berger & Kimmel, Acad. Press, N.Y., Vol. 152, pp. 673-684, 1987; and *The Molecular Biology of the Yeast Saccharomyces*, Eds. Strathern et al., Cold Spring Harbor Press, Vols. I and II, 1982. A constitutive yeast promoter such as ADH or LEU2 or an inducible promoter such as GAL may be used ("Cloning in Yeast," Ch. 3, R. Rothstein In: *DNA Cloning* Vol. 11, *A Practical Approach*, Ed. DM Glover, IRL Press, Wash., D.C., 1986). Alternatively, vectors may be used which promote integration of foreign DNA sequences into the yeast chromosome.

An alternative expression system which could be used to express a peptide having, for example, a sequence as set forth in SEQ ID NOS: 2, 3, 4, 5, 6, 7, 8, 9, 10, 24, 25, 26 or 27 is an insect system. In one such system, *Autographa californica* nuclear polyhedrosis virus (AcNPV) is used as a vector to express foreign or mutated sequences. The virus grows in *Spodoptera frugiperda* cells. The sequence encoding a peptide of the invention may be cloned into non-essential regions (for example, the polyhedrin gene) of the virus and placed under control of an AcNPV promoter (for example the polyhedrin promoter). Successful insertion of the sequences coding for a peptide of the invention will result in inactivation of the polyhedrin gene and production of non-occluded recombinant virus (i.e., virus lacking the proteinaceous coat coded for by the polyhedrin gene). These recombinant viruses are then used to infect *S. frugiperda* cells in which the inserted gene is expressed, see Smith, et al., *J. Viol.* 46:584, 1983; Smith, U.S. Pat. No. 4,215,051.

The vectors of the invention can be used to transform a host cell. By transform or transformation is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell.

A transformed cell or host cell generally refers to a cell (e.g., prokaryotic or eukaryotic) into which (or into an ancestor of which) has been introduced, by means of recombinant DNA techniques, a DNA molecule encoding a peptide of the invention, or analog thereof.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, methods of transfection or transformation with DNA include calcium phosphate co-precipitates, conventional mechanical procedures such as microinjection, electroporation, insertion of a plasmid encased in virus vectors and the like, as well as others known in the art, may be used. Eukaryotic cells can be cotransfected with DNA sequences encoding a peptide of the invention and a second foreign DNA molecule encoding a selectable marker, such as the herpes simplex thymidine kinase gene. Another method is to use a eukaryotic viral vector, such as simian virus 40 (SV40) or bovine papilloma virus, to transiently infect or transform eukaryotic cells and express the protein. (*Eukaryotic Viral Vectors*, Cold Spring Harbor Laboratory, Gluzman ed., 1982). Typically, a eukaryotic host will be utilized as the host cell. The eukaryotic cell may be a yeast cell (e.g., *Saccharomyces cerevisiae*), an insect cell (e.g., *Drosophila* sp.) or may be a mammalian cell, including a human cell.

Eukaryotic systems, and mammalian expression systems, allow for post-translational modifications of expressed mammalian proteins to occur. Eukaryotic cells which possess the cellular machinery for processing of the primary transcript, glycosylation, phosphorylation, and, advantageously secretion of the gene product should be used. Such host cell lines may include, but are not limited to, CHO, VERO, BHK, HeLa, COS, MDCK, Jurkat, HEK-293, and WI38.

Mammalian cell systems which utilize recombinant viruses or viral elements to direct expression may be engineered. For example, when using adenovirus expression vectors, a nucleic acid sequence encoding a peptide of the invention may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing a peptide of the invention in infected hosts (e.g., see Logan & Shenk, *Proc. Natl. Acad. Sci. USA*, 81:3655-3659, 1984). Alternatively, the vaccinia virus 7.5K promoter may be used. (e.g., see, Mackett, et al., *Proc. Natl. Acad. Sci. USA*, 79:7415-7419, 1982; Mackett, et al., *J. Virol.* 49:857-864, 1984; Panicali, et al., *Proc. Natl. Acad. Sci. USA* 79:4927-4931, 1982). Of particular interest are vectors based on bovine papilloma virus which have the ability to replicate as extrachromosomal elements (Sarver, et al., *Mol. Cell. Biol.* 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of a gene in host cells (Cone & Mulligan, *Proc. Natl. Acad. Sci. USA,* 81:6349-6353, 1984). High level expression may also be achieved using inducible promoters, including, but not limited to, the metallothionine IIA promoter and heat shock promoters.

For long-term, high-yield production of recombinant proteins, stable expression is desirable. Rather than using expression vectors which contain viral origins of replication, host cells can be transformed with the DNA encoding a peptide of the invention (e.g., a peptide having a sequence as set forth in SEQ ID NOS: 2, 3, 4, 5, 6, 7, 8, 9, 10, 24, 25, 26 or 27) controlled by appropriate expression control elements (e.g., promoter, enhancer, sequences, transcription terminators, polyadenylation sites, and the like), and a selectable marker. The selectable marker in the recombinant vector confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in an enriched media, and then are switched to a selective media. A number of selection systems may be used, including, but not limited to, the herpes simplex virus thymidine kinase (Wigler, et al., *Cell,* 11:223, 1977), hypoxanthine-guanine phosphoribosyltransferase (Szybalska & Szybalski, *Proc. Natl. Acad. Sci. USA,* 48:2026, 1962), and adenine phosphoribosyltransferase (Lowy, et al., *Cell,* 22:817, 1980) genes can be employed in tk-, hgprt- or aprt-cells respectively. Also, antimetabolite resistance can be used as the basis of selection for dhfr, which confers resistance to methotrexate (Wigler, et al., *Proc. Natl. Acad. Sci. USA,* 77:3567, 1980; O'Hare, et al., *Proc. Natl. Acad. Sci. USA,* 8:1527, 1981); gpt, which confers resistance to mycophenolic acid (Mulligan & Berg, *Proc. Natl. Acad. Sci. USA,* 78:2072, 1981; neo, which confers resistance to the aminoglycoside G-418 (Colberre-Garapin, et al., *J. Mol. Biol.* 150:1, 1981); and hygro, which confers resistance to hygromycin (Santerre, et al., *Gene* 30:147, 1984) genes. Recently, additional selectable genes have been described, namely trpB, which allows cells to utilize indole in place of tryptophan; hisD, which allows cells to utilize histinol in place of histidine (Hartman & Mulligan, *Proc. Natl. Acad. Sci. USA* 85:8047, 1988); and ODC (ornithine decarboxylase) which confers resistance to the ornithine decarboxylase inhibitor, 2-(difluoromethyl)-DL-ornithine, DFMO (McConlogue L., In: *Current Communications in Molecular Biology,* Cold Spring Harbor Laboratory, ed., 1987).

In another embodiment, the invention provides antibodies that specifically bind to a peptide of the invention (e.g., SEQ ID NOS: 2, 3, 4, 5, 6, 7, 8, 9, 10, 24, 25, 26 or 27). For example, an antibody that specifically binds to a peptide having a sequence of SEQ ID NO: 2 does not bind to a peptide having a sequence of SEQ ID NO: 4. If the peptide is glycosylated, the glycosylation pattern can be utilized as part of a purification scheme via, for example, lectin chromatography. Such antibodies are useful for research and diagnostics in the study of inflammatory disorders and diseases (e.g., juvenile arthritis, rheumatoid arthritis, psoriatic arthritis, osteoarthritis (OA), inflammatory bowel disease, (IBD), multiple sclerosis (MS), dermato myositis, diabetes, and the like), and associated pathologies in general.

Such antibodies may be administered alone or contained in a pharmaceutical composition comprising antibodies that specifically bind to a sequence as set forth in SEQ ID NOS: 2, 3, 4, 5, 6, 7, 8, 9, 10, 24, 25, 26 or 27 and other reagents effective as modulators of inflammatory reactions in vitro and in vivo.

The term "epitope", as used herein, refers to an antigenic determinant on an antigen, such as a peptide having a sequence as set forth in SEQ ID NOS: 2, 3, 4, 5, 6, 7, 8, 9, 10, 24, 25, 26 or 27 to which the paratope of an antibody, such as an antibody that specifically binds to a sequence as set forth in SEQ ID NOS: 2, 3, 4, 5, 6, 7, 8, 9, 10, 24, 25, 26 or 27 of the invention. Antigenic determinants usually consist of chemically active surface groupings of molecules, such as amino acids or sugar side chains, and can have specific three-dimensional structural characteristics, as well as specific charge characteristics.

Antibodies which bind to a peptide of the invention can be prepared using intact peptides or fragments (e.g., fragments of SEQ ID NO: 1, SEQ ID NO: 13, SEQ ID NO: 33) corresponding to the sequences of the peptides of the invention) containing small peptides of interest as the immunizing antigen. The polypeptide or a peptide used to immunize an animal can be derived from translated cDNA or chemical synthesis which can be conjugated to a carrier protein, if desired. Such commonly used carriers, which are chemically coupled to the peptide, include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology,* Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Antibodies of the invention include polyclonal antibodies, monoclonal antibodies, and fragments of polyclonal and monoclonal antibodies.

The preparation of polyclonal antibodies is well-known to those skilled in the art. See, for example, Green et al., Production of Polyclonal Antisera, in *Immunochemical Protocols* (Manson, ed.), pages 1-5 (Humana Press 1992); Coligan et al., Production of Polyclonal Antisera in Rabbits, Rats, Mice and Hamsters, in *Current Protocols in Immunology,* section 2.4.1 (1992), which are hereby incorporated by reference.

The preparation of monoclonal antibodies likewise is conventional. See, for example, Kohler & Milstein, *Nature,* 256: 495 (1975); Coligan et al., sections 2.5.1-2.6.7; and Harlow et al., *Antibodies: A Laboratory Manual,* page 726 (Cold Spring Harbor Pub. 1988), which are hereby incorporated by reference. Alternatively, an antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the frame-work regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA,* 86:3833 (1989), which is hereby incorporated in its entirety by reference. Techniques for producing humanized monoclonal antibodies are described, for example, by Jones et al., *Nature,* 321:522 (1986); Riechmann et al., *Nature,* 332:323 (1988); Verhoeyen et al., *Science,* 239:1534 (1988); Carter et al., *Proc. Nat'l Acad. Sci. USA,* 89:4285 (1992); Sandhu, *Crit. Rev. Biotech.,* 12:437 (1992); and Singer et al., *J. Immunol.,* 150:2844 (1993), which are hereby incorporated by reference.

In another embodiment, the invention provides for the generation of autoreactive cells with the ability to recognize organ specific antigens and to produce mediators that suppress the activity of pathogenic cells instead of having the potential to promote disease. For example, it is desirable to selectively stimulate the production of immunomodulator compounds such as, for example, cytokines like IL-4, IL-10, IL-9, IL-13 and TGF-β, which are involved in either inflammatory or anti-inflammatory responses, as the case may be.

It will be appreciated that the induction of such immunomodulator compounds may be associated with the identity of the selected epitope in the context of the T cell repertoire and in the cytokine context during priming and the inoculation regimen. Significantly, it will be appreciated that such a strategy is not limited to antigens that are central to the pathogenesis of an autoimmune disease, but potentially can employ any organ-specific antigen, particularly antigens having similar characteristics that are recognized by the T cells. As such, selective induction of such immunomodulator compounds has several advantages in treatments designed for the amelioration of autoimmune disorders. For example, such a treatment does not require identification of those epitopes that are involved in the etiology of a given disease. Rather, the treatment is based on a family of peptides capable of modulating any immune mediated T cell response, e.g., for example, inflammation associated with for example, autoimmunity, infection, or cancer. This broad-based bystander suppression (modulation) of T cells reactive against various epitopes may be generated, for example, by using epitopes unrelated to the disease causing epitope but similar in recognizable functional features (i.e., modulation of immunity through the manipulation of T cells specific for the epitope). For example, as shown in FIG. 19, epitope specific sequence, whether from whole protein or short peptide sequence, correlates between species. This shows that if peptides are similar then there is a significant likelihood that similar peptides are recognized. Moreover, a strategy of using crossover antigen would limit the risk of exacerbating the disease due to transient activation phase of pathogenic T cells during antigen therapy and it may circumvent the refractoriness of pathogenic T cells to peripheral tolerance mechanisms mediating anergy and deletion.

In another embodiment, the peptides of the invention are used as immunological agents in a pharmaceutical composition administered to modulate (e.g., prevent or dim down) an immune-mediated disease. Accordingly, the peptides of the invention are intended to encompass salts and functional derivatives thereof, as well as hsp60 peptide analogs, so long as the biological activity of the protein or peptide with respect to modulating immune-mediated disease (i.e., a disease associated with an immune response)s is maintained.

Peptides of the invention (e.g., a peptide having a sequence as set forth in SEQ ID NOS: 2, 3, 4, 5, 6, 7, 8, 9, 10, 24, 25, 26 or 27) are, in one embodiment, administered prior to development of an immune-mediated disease in a subject at risk thereof. The term "prior to" is intended to mean a period of time during which a reaction based upon hsp60 autoimmunity is modulated by such treatment in the host, at a time such that the optimal modulation (e.g., down-regulation) coincides with the time of the inflammatory reaction. Alternatively, a peptide of the invention can be administered in conjunction with another anti-inflammatory agent, such as an anti-inflammatory cytokine or an anti-TNFα agent.

In the present invention, administration of the pharmaceutical composition containing hsp60 peptides, or analogs thereof, as immunologically active agents to modulate inflammation in a subject can be through various routes known in the art, such as topically, orally, intranasally, intravenously, intramuscularly, or subcutaneously. In one embodiment, the modes of administration are intravenously, which is known to induce tolerance, or orally or intranasally, which are known to induce a TH1→TH2 shift. The dosage of the peptides of the invention, or analogs thereof, will depend upon a number of factors including the type of disease, the age and weight of the subject, as well as the severity of the symptoms. One of skill in the art, can determine the proper dose empirically. For example, an optimum dosage and regimen can be determined by those of skill in the art by measuring for a shift from TH1 cytokine response to a TH2 cytokine response such as dosages in the range of 0.25 to 2.5 to 25 mg of peptide.

Peptides of the invention, or analogs thereof, may be given during or after an immunological or inflammatory reaction to further modulate (e.g., reduce or down-regulate) the inflammatory reaction. Inflammatory reactions applicable to the methods and compositions of the invention include, for example, autoimmune disease or disorders (e.g., juvenile arthritis, psoriatic arthritis, osteoarthritis (OA), dermato myositis, insulin dependent diabetes mellitus (IDDM), multiple sclerosis, systemic lupus erythematosus, Sjogren's syndrome, scleroderma, polymyositis, chronic active hepatitis, mixed connective tissue disease, primary biliary cirrhosis, pernicious anemia, autoimmune thyroiditis, idiopathic Addison's disease, vitiligo, gluten-sensitive enteropathy, Graves' disease, inflammatory bowel disease, myasthenia gravis, autoimmune neutropenia, idiopathic thrombocytopenia purpura, rheumatoid arthritis, cirrhosis, pemphigus vulgaris, autoimmune infertility, Goodpasture's disease, bullous pemphigoid, discoid lupus, ulcerative colitis, and dense deposit disease). The diseases set forth above, as referred to herein, include those exhibited by animal models for such diseases, such as, for example non-obese diabetic (NOD) mice for IDDM and experimental autoimmune encephalomyelitis (EAE) mice for multiple sclerosis.

The methods of the present invention can be used to treat such autoimmune-mediated diseases and inflammatory diseases or disorders by modulating (e.g., reducing or eliminating, dimming down) the immune response to the subject's own (self) tissue, or, alternatively, by reducing or eliminating a pre-existing autoimmune response directed at tissues or organs transplanted to replace self tissues or organs damaged by the autoimmune response.

The administration of one or more peptides of the invention (e.g., peptides having sequences as set forth in SEQ ID NOS: 2, 3, 4, 5, 6, 7, 8, 9, 10, 24, 25, 26 or 27) is, in one embodiment, concomitant with the administration of conventional anti-inflammatory or immunosuppressive therapy.

It is expected that different epitopes of the hsp60 protein, such as those presented in Table 1 (e.g., SEQ ID NOS: 2, 3, 4, 5, 6, 7, 8, 9, 10, 24, 25, 26 or 27), may be more effective in inflammatory responses in different individuals. Thus, the peptides of the invention can be screened against peripheral blood lymphocytes of the intended subject to see which peptide has the optimum effect on inflammation. For example, class II MHC molecules bind to peptides 12-15 amino acid residues in length (e.g., as short as 9 amino acid residues), and that class I MHC molecules bind peptides of 7-9 amino acid residues. Thus, peptide fragments of hsp60, such as those presented in Table 1, can be readily screened to determine one or more optimal peptides that can be administered to a particular individual subject, or to a subject of a given HLA-type, to modulate the individual's immune response, for example, to shift to a TH2 cytokine response and thereby down-regulate his/her inflammation.

Peripheral blood lymphocytes (PBL) of an individual human subject can be isolated from whole blood by Ficoll-Hypaque density gradient centrifugation as is well-known in the art. This sample of the subject's lymphocytes can be tested for binding to the peptides to be screened in accordance with the method disclosed in Mozes et al., U.S. Pat. No. 5,356,779, or can be tested for in vitro T-cell proliferation and subsequent T-cell cytokine response as assays to determine an optimal or near optimal peptide sequence for a specific individual subject.

Another way to screen a panel of peptides is to test the subject's lymphocytes for in vitro proliferation in the presence of each of the peptides of the panel or to test for TH1→TH2 shift caused by such peptides. Thus, supernatants of T-cells cultured with test peptides at concentrations of 5-50 ug/ml may be collected at different time points and tested for the activity of various cytokines, such as IFNγ and IL-4 secreted into the culture medium, which can be quantitated by ELISA using standard ELISA protocols, or for the presence of antibodies of particular classes. TH1 cells secrete cytokines which induce T cell proliferation, and cytokines such as IFNγ, which mediate tissue inflammation. On the other hand, TH2 cells secrete IL-4, which helps B-cells secrete antibodies of the IgG and IgE class and suppress the production of TH1 inflammatory cytokines, as well as IL-10, which indirectly inhibits TH1 activation by affecting antigen presentation and inflammatory cytokine production by macrophages. Accordingly, a measurement of the cytokine profile of the in vitro proliferated T cells will also be an indication of a shift from a TH1 T cell response to a TH2 T cell response. Thus, the TH1→TH2 shift can serve as a marker for monitoring the in vitro response of a subject's T lymphocytes to various test peptides in determining optimal or near optimal peptides.

The therapeutic regimens and pharmaceutical compositions of the invention can be used with additional immune response enhancers or biological response modifiers including, but not limited to, the cytokines IFN-γ, IFN-β, TNFα, IL-1, IL-2, IL-4, IL-6, IL-10, IL-12, IL-16, IL-17, or other cytokine affecting immune cells.

One or more peptides of the invention can be administered, for in vivo application, mucosally (e.g. by suppository, inhaler or orally), parenterally by injection, or by gradual perfusion over time. Administration may be orally, intravenously, intraperitoneally, intramuscularly, subcutaneously, intracavity, or transdermally. One or more peptides of the invention can also be co-administered with an adjuvant, hormone, cytokine, corticosteroid, or the like. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

It is envisioned that the invention can be used to treat pathologies associated with immune-mediated disorders, such as inflammation and autoimmune disorders, pathogenic infections and cancerous or precancerous conditions, by modulating an immune response in the treated subject. Therefore, the present invention encompasses methods for ameliorating a disorder associated with immune-mediated diseases, including those associated with an antigen-specific immune response to a self-antigen. The invention methods include treating a subject having the disorder or disease condition, at the site of the disorder or condition, with one or more peptides of the invention having, for example, a sequence as set forth in SEQ ID NOS: 2, 3, 4, 5, 6, 7, 8, 9, 10, 24, 25, 26, 27, or an analog thereof. Generally, the terms "treating", "treatment" and the like are used herein to mean affecting a subject, tissue or cell to obtain a desired pharmacologic and/or physiologic effect. The effect may be prophylactic in terms of completely or partially preventing a disease or sign or symptom thereof, and/or may be therapeutic in terms of a partial or complete cure for an infection or disease and/or adverse effect attributable to the infection or disease. "Treating" as used herein covers any treatment of, or prevention of a disease in a vertebrate, a mammal, particularly a human, and includes: (a) preventing the disorder from occurring in a subject that may be predisposed to the disorder, but has not yet been diagnosed as having it; (b) inhibiting the disorder, i.e., arresting its development; (c) relieving or ameliorating the disorder, i.e., causing regression of the disorder or, (d) modulating an ongoing immune response that mediates the disorder so as to counteract the progression of the condition or disorder. Generally, prevention or reduction of inflammatory response as contemplated by the present invention, is brought about by modulating the immune response by dimming the T cell reactivity in an antigen-specific manner by inducing stimulation of regulatory T cells. For example, in JIA patients having differential recognition of dnaJ peptide motifs, active disease is associated with recognition of bacterial peptide sequence while remission is associated with recognition of human epitopes of the dnaJ human homologue.

The invention includes various pharmaceutical compositions useful for ameliorating symptoms attributable to an immune-mediated disorder, as describe herein. The pharmaceutical compositions according to one embodiment of the invention are prepared by bringing an antibody against a peptide having a sequence selected from the group consisting of SEQ ID NOS: 2, 3, 4, 5, 6, 7, 8, 9, 10, 24, 25, 26 or 27, a peptide analog of the foregoing sequences, a peptide mimetic of the foregoing, a drug, chemical or combination of chemicals or an agent that modulates the biological activity of the peptides of invention, into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences*, 15th ed. Easton: Mack Publishing Co., 1405-1412, 1461-1487 (1975) and *The National Formulary XIV.*, 14th ed. Washington: American Pharmaceutical Association (1975), the contents of which are hereby incorporated by reference. The pH and exact concentration of the various components of the pharmaceutical composition are adjusted according to routine skills in the art. See *Goodman and Gilman's The Pharmacological Basis for Therapeutics* (7th ed.).

The pharmaceutical compositions may be prepared and administered in dose units. Solid dose units are tablets, capsules and suppositories. For treatment of a subject, depending on activity of the compound, manner of administration, nature and severity of the disorder, age and body weight of the subject, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g., in Langer, *Science*, 249:1527, (1990); Gilman et al. (eds.) (1990), each of which is herein incorporated by reference.

In one embodiment, the invention provides a pharmaceutical composition useful for administering a peptide of the invention, an analog thereof, or a nucleic acid encoding a peptide of the invention, to a subject in need of such treatment. "Administering" the pharmaceutical composition of the present invention may be accomplished by any means known to the skilled artisan. In one embodiment, a "subject" refers to a mammal, in another aspect the mammal is a human, but may be any organism.

A peptide or antibody of the invention can be administered orally, parenterally, enterically, by injection, rapid infusion, nasopharyngeal absorption, dermal absorption, rectally and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water.

Another delivery system for nucleic acid and peptide sequences of the invention is a colloidal dispersion system. Colloidal dispersion systems include macromolecule complexes, nanocapsules, microspheres, beads, and the like.

In another embodiment, the invention provides a method for identifying an agent which interacts with or modulates the activity of an hsp60 protein or peptide derived therefrom. In a related embodiment, such method can include incubating an agent and such protein or peptide, or can include expressing in a recombinant cell such a peptide under conditions sufficient to allow the agent to interact synergistically with the peptide in modulating the immune response. The methods also contemplate determining the affect of the agent on the activity of the peptide. The term "affect", as used herein, encompasses any means by which a peptide's activity can be modulated, and includes measuring the interaction of the agent with the peptide by physical means including, for example, fluorescence detection of the binding of the agent to the peptide. "Agents" can include, for example, polypeptides, peptidomimetics, chemical compounds, small molecules and biologic agents as described herein.

Incubating includes conditions which allow contact between the test agent and a peptide of the invention, or a cell expressing a peptide of the invention. Contacting includes in solution and in solid phase. The test agent may optionally be a combinatorial library for screening a plurality of agents. Agents identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008-1012, 1985), oligonucleotide ligation assays (OLAs) (Landegren, et al., *Science*, 241:1077, 1988), and the like. Molecular techniques for DNA analysis have been reviewed (Landegren, et al., *Science*, 242:229-237, 1988).

Areas of investigation are the development of therapeutic treatments. The screening identifies agents that modulate the biological activity of a peptide of the invention in targeted organisms. Of particular interest are screening assays for agents that have a low toxicity or a reduced number of side effects for humans.

The term "agent" as used herein describes any molecule, e.g. protein or pharmaceutical, with the capability of altering or mimicking the physiological function or expression of a peptide having a sequence as set forth in SEQ ID NOS: 2, 3, 4, 5, 6, 7, 8, 9, 10, 24, 25, 26 or 27). Generally, a plurality of assay mixtures are run in parallel with different agent concentrations to obtain a differential response to the various concentrations. Typically, one of these concentrations serves as a negative control, i.e. at zero concentration or below the level of detection.

In another embodiment, the invention provides a method for identifying an agent which modulates (e.g., inhibiting) an hsp60-associated disorder (e.g., an inflammatory disorder or disease) by administering to a cell or subject having the hsp60-associated disorder an effective amount of a composition which contains a peptide of the invention, or an analog thereof, or an agent (e.g, an antibody, ribozyme, antisense molecule, or double-stranded interfering RNA molecules) that interacts with or inhibits the symptoms of the hsp60 associated disorder. Symptom can include, for example, the production of cytokines as identified herein, TH1 and TH2 responses, as well as pathologies associated with inflammation (e.g., swelling, vasodilation and the like).

Detection of hsp60 or dnaJP1 Polypeptides In Vivo and In Vitro

In a further embodiment, the invention provides a method of detecting an hsp60 polypeptide in a subject including contacting a cell component containing or suspected of containing an hsp60 or dnaJP1 polypeptide with a reagent (e.g., an antibody that specifically binds to a peptide sequence as set forth in SEQ ID NOS: 2, 3, 4, 5, 6, 7, 8, 9, 10, 24, 25, 26 or 27) which binds to the cell polypeptide (herein after cell component). The cell component may contain in addition to hsp60 or dnaJP 1 polypeptide, a nucleic acid, such as DNA or RNA. When the cell component is protein, the reagent is typically an antibody probe. The probes are detectably labeled, for example, with a radioisotope, a fluorescent compound, a bioluminescent compound, a chemiluminescent compound, a metal chelator or an enzyme. Those of ordinary skill in the art will know of other labels suitable for binding to an antibody or nucleic acid probe, or will be able to ascertain such, using routine experimentation. There are many different labels and methods of labeling known to those of ordinary skill in the art. Examples of the types of labels which can be used in the present invention include enzymes, radioisotopes, colloidal metals, fluorescent compounds, chemiluminescent compounds, and bioluminescent compounds.

A monoclonal antibody of the invention, directed toward a peptide of the invention (e.g., a peptide having a sequence as set forth in SEQ ID NOS: 2, 3, 4, 5, 6, 7, 8, 9, 10, 24, 25, 26 or 27) is useful for the in vivo and in vitro detection of antigen. The detectably labeled monoclonal antibody is given in a dose which is diagnostically effective. The term "diagnostically effective" means that the amount of detectably labeled monoclonal antibody is administered in sufficient quantity to enable detection of a proteins or polypeptide antigen for which the monoclonal antibodies are specific.

The concentration of a detectably labeled monoclonal antibody administered to a subject should be sufficient such that the binding to those cells, body fluid, or tissue having an hsp60 polypeptide sequence is detectable when compared to the background. Further, it is desirable that the detectably labeled monoclonal antibody be rapidly cleared from the circulatory system in order to give the best target-to-background signal ratio.

For in vivo diagnosis, radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

In some instances it may be advantageous to deliver and express a peptide sequence of the invention locally (e.g., within a particular tissue or cell type). For example, local expression of a peptide of the invention (e.g., a peptide having a sequence as set forth in SEQ ID NOS: 2, 3, 4, 5, 6, 7, 8, 9, 10, 24, 25, 26 or 27) in cartilage tissues, pancreatic tissue, skin tissue, or gut tissue of an animal. The nucleic sequence may be directly delivered to the tissue and cells, for example. Such delivery methods are known in the art and include electroporation, viral vectors and direct DNA uptake.

For example, a nucleic acid constructs of the present invention will comprise nucleic acid molecules in a form suitable for uptake into target cells within a host tissue. The nucleic acids may be in the form of bare DNA or RNA molecules, where the molecules may comprise one or more structural genes, one or more regulatory genes, antisense strands, strands capable of triplex formation, or the like. Commonly, the nucleic acid construct will include at least one structural gene under the transcriptional and translational control of a suitable regulatory region. More usually, nucleic acid constructs of the present invention will comprise nucleic acids incorporated in a delivery vehicle to improve transfection efficiency, wherein the delivery vehicle will be dispersed within larger particles comprising a dried hydrophilic excipient material.

One such delivery vehicle comprises viral vectors, such as retroviruses, adenoviruses, and adeno-associated viruses, which have been inactivated to prevent self-replication but which maintain the native viral ability to bind a target host cell, deliver genetic material into the cytoplasm of the target host cell, and promote expression of structural or other genes which have been incorporated in the particle. Suitable retrovirus vectors for mediated gene transfer are described in Kahn et al. (1992) *CIRC. RES.* 71:1508-1517, the disclosure of which is incorporated herein by reference. A suitable adenovirus gene delivery is described in Rosenfeld et al. (1991) *Science* 252:431-434, the disclosure of which is incorporated herein by reference. Both retroviral and adenovirus delivery systems are described in Friedman (1989) *Science* 244:1275-1281, the disclosure of which is also incorporated herein by reference.

The following examples are intended to illustrate but not limit the invention.

EXAMPLE 1

Peptide Identification

To identify the promiscuous pan-DR peptides, a computer algorithm described in U.S. Pat. No. 6,037,135 (incorporated herein by reference in its entirety) that identifies motifs for binding of peptides to various MHC class II molecules, was used. Sequences of both mycobacterial, *E. coli*, and human hsp60 were scanned, and based on the predicted binding of peptide sequences to three subtypes of HLADR, namely DR1, DR4 and DR7, peptides were designed (Table 1). The peptides were selected on the level of predicted binding to DR1, 4, and 7. The peptides of the present invention including those listed in Table 1 have been identified by in vitro tests for the ability to induce the proliferation of autoreactive T cells or to induce the secretion of cytokines (e.g., lymphokines) from these T cells or to induce other effector functions such as cytotoxicity. Moreover, selection of peptides includes selection for peptide motifs that when appropriately administered dim, reduce, or otherwise eliminate inflammatory responses of T cells by modulating T cell response.

An epitope identified by the computer algorithm was considered eligible when it was predicted to have sufficient affinity to HLA DR1, DR4 and DR7 (Pan-DR score=3). A 15-mer peptide was subsequently designed in such a fashion that at least two, in another embodiment, three, flanking amino acid residues were present at both sides of the predicted core epitope. Every peptide, containing a Pan DR binding epitope, was subsequently matched with its homologous (human, *E. coli*, or mycobacterial) counterpart. In this way, a total of 12 peptides were designed, 4 mycobacterial peptides (p1, p3, p5, p7), 4 *E. coli* peptides (p9, p10, p11, p12) and 4 homologous human peptides (p2, p4, p6, p8). The peptides are shown in Table 1.

EXAMPLE 2

T-Cell Proliferation

To test T cell proliferation a direct culture of Peripheral Blood Mononuclear Cells (PBMC) were contacted with selected peptides of Table 1. Over 80 subjects with JIA were tested. The group consisted of a random selection of subjects with all subtypes of JIA, during different phases of disease activity and medical treatment. PBMC of subjects were tested in a standard proliferation assay. PBMC were isolated from heparinized blood using a Ficoll Isopaque density gradient. PBMC were cultured at a number of 200,000 cells per 200 microliter per well in 96 well round bottom plates in RPMI containing 15% AB serum. Cells were cultured for 6 days (120 hours) at 37° C. in 5% $CO_2$ with 100% relative humidity. During the last 16 hours of culture 1 TCi (=37 kBq) tritiated thymidine was added to each well. Incorporated radioactivity was measured by liquid scintillation counting and expressed as counts per minute (cpm). The magnitude of the proliferative response was expressed as cpm and as stimulation index (SI): the mean cpm of cells cultured with antigen divided by the mean cpm of cells cultured with medium alone. A SI of 2 or higher can be considered positive response to an antigen. The results are shown in FIG. 5. A majority of subjects showed a positive T cell proliferative response to both human and mycobacterial whole hsp60, as could be expected from previous data. All hsp60 peptides induced peptide specific proliferative T cell responses in 40 to 60% of subjects of JIA.

Figure 6:
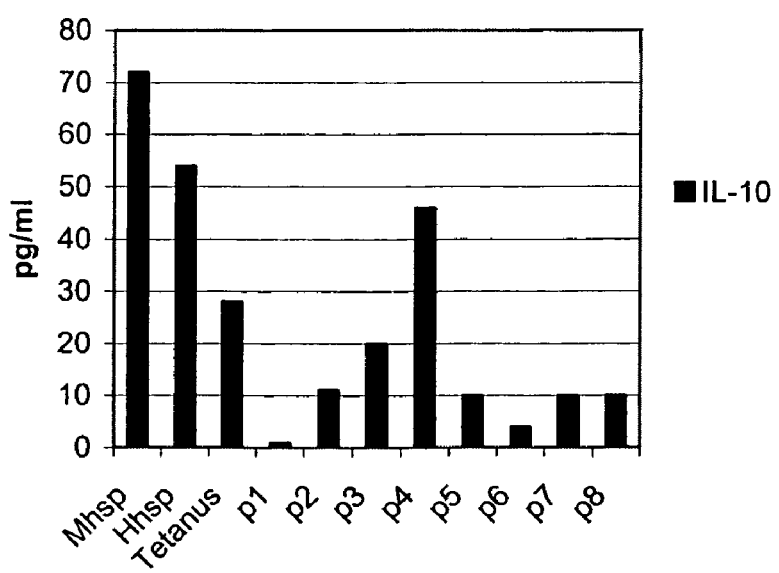
FIG. 6 shows antigen-specific production of IL-10 after in vitro culture with the pan DR-binding hsp60 peptides of FIG. 5 plus tetanus toxin (X axis). The Y axis indicates the production of IL-10 (in pg/ml) in response to the different peptides.
Figure 7:
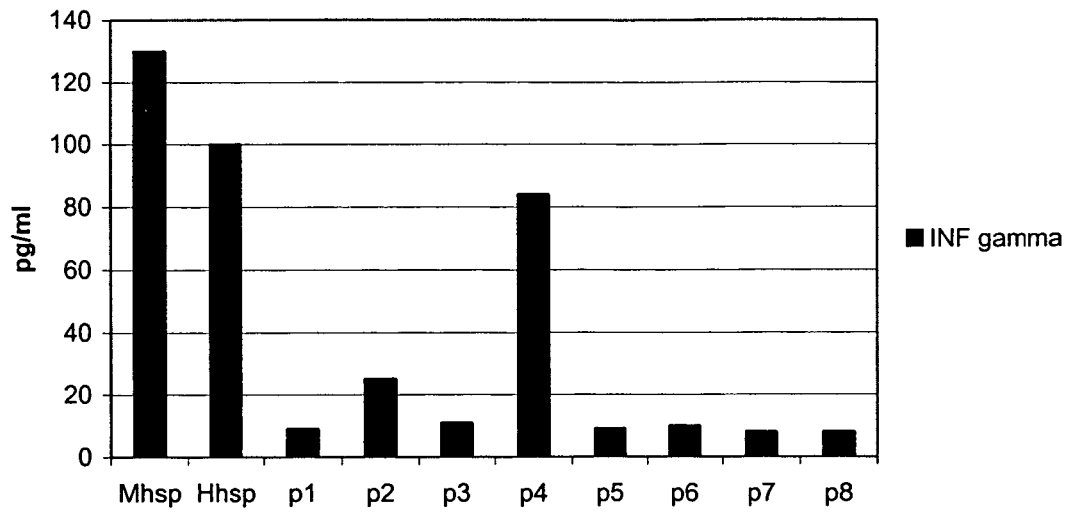
FIG. 7 shows the antigen-specific production of Interferon-γ (IFN-γ) after in vitro culture with the pan DR-binding hsp60 peptides of FIG. 5 (X axis). On the Y axis the production of IFN-γ (in pg/ml) is shown in response to the different peptides. Negative control peptide mycobacterial hsp60 256-270 did not induce any cytokine production and is not shown.
Figure 8:
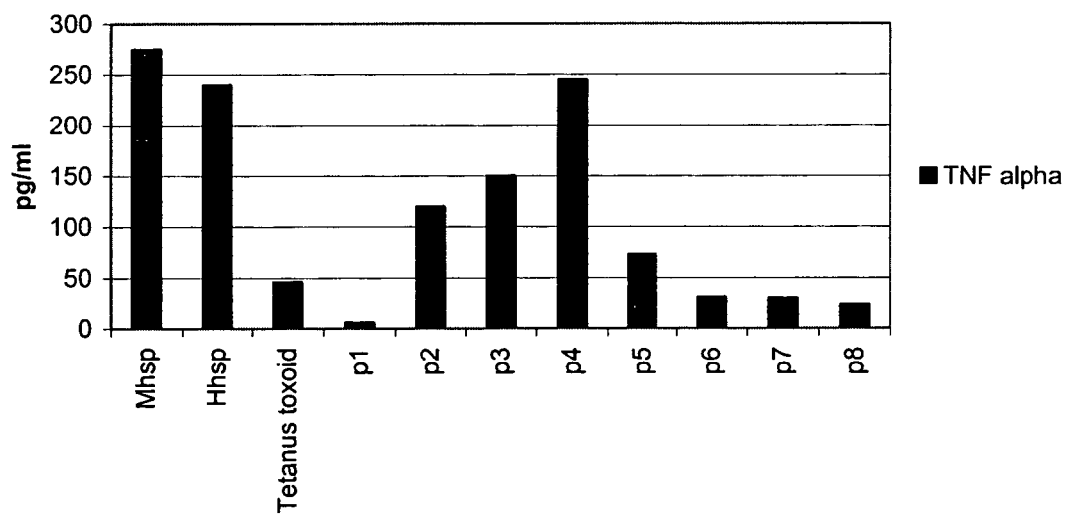
FIG. 8 shows the antigen-specific production of TNF-α after in vitro culture with the pan DR-binding hsp60 peptides of FIG. 5 plus tetanus toxin (X axis). On the Y-axis the production of TNF-α (in pg/ml) is shown in response to the different peptides. The negative control (not shown) peptide (residues 256-270 of *M. tub.* hsp60) did not induce any cytokine production.

In a smaller group of 18 subjects with JIA, T cell proliferation was combined with measurement of antigen specific cytokine production. PBMC were cultured at 200,000 cells in 200 microliter per well in a 96 well plate as described above. After 72 hours supernatants were removed and cytokine production was measured with a standard ELISA according to the manufacturer's protocol (B&D). The following cytokines were tested: IL-4, IL-10, IFN-γ, TGF-β, TNF-α and IL-1RA. FIGS. 6-8 show the antigen specific cytokine production of IL-10, IFN-γ, and TNF-α, respectively, after 72 hours of culture with the Pan DR binding peptides. Again, in a majority of subjects antigen-specific cytokine production could be detected in PBMC cultured in vitro with the peptides. No antigen-specific production of IL-4 could be detected, which is probably due to the sensitivity of the cytokine ELISA.

Figure 9:
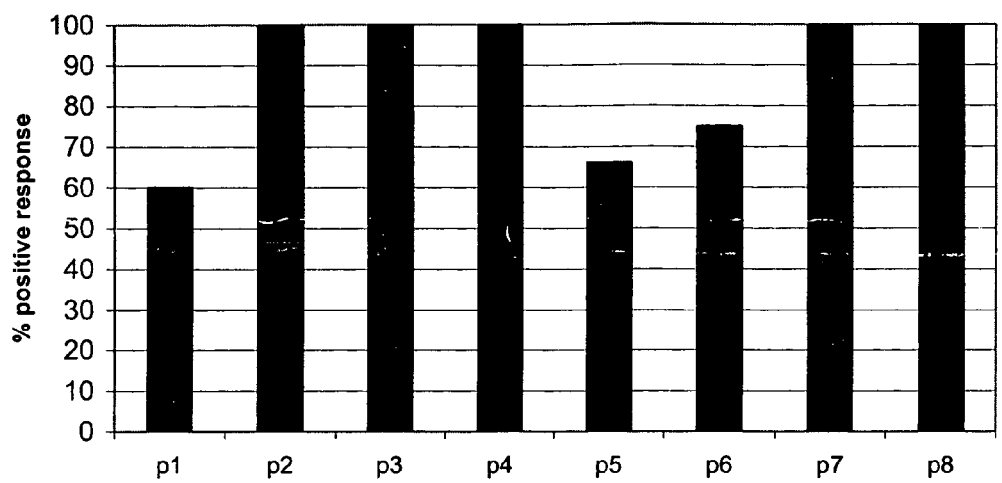
FIG. 9 shows the immunological recognition (defined as T-cell proliferation and/or production of cytokines) in response to hsp60 peptides p1 to 8 in cells from 18 subjects with JIA.

Immunological recognition of an antigen can be defined as antigen-specific T cell proliferation and/or antigen-specific cytokine production after culture with the specific antigens. In addition, in a very high percentage of subjects (ranging from 60 to 100%), T cell recognition of these pan DR binding hsp60 peptides could be detected (FIG. 9). This percentage can be considered extremely high if one considers both the failures of previous studies to determine T cell epitopes in JIA and the heterogenic HLA background in subjects with JIA.

Figure 10:
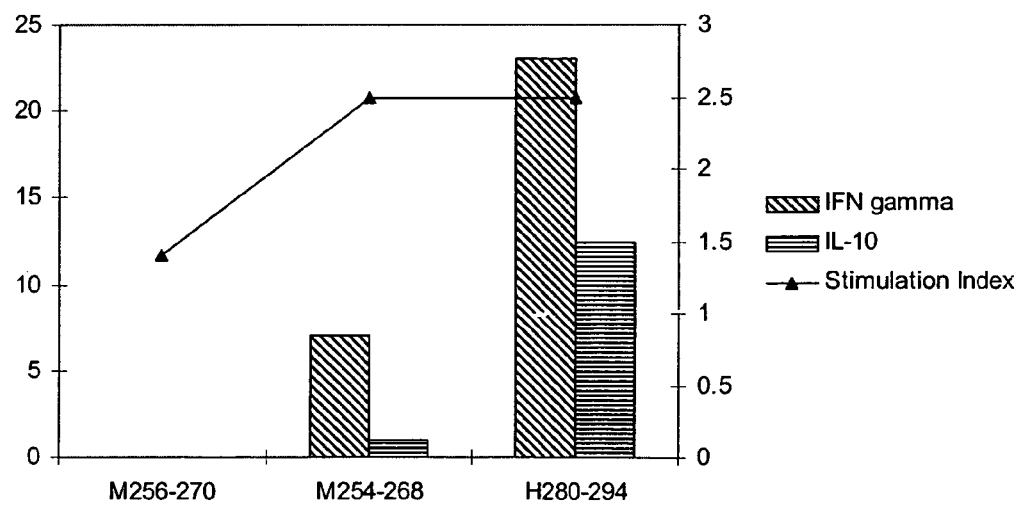
FIG. 10 shows a comparison of the immunological reactivity induced by negative control peptide (residues 256-270 of M. tub. hsp60) compared to two peptides of the invention based on pan DR-binding (p1, residues 254-268 of M. tub. hsp60, SEQ ID NO: 2; and p2, residues 280-294 of human hsp60, SEQ ID NO: 3). The right Y-axis depicts the stimulation index SI, and the left Y-axis depicts the production of cytokines INF-γ and IL-10 in pg/ml.
Figure 11B:
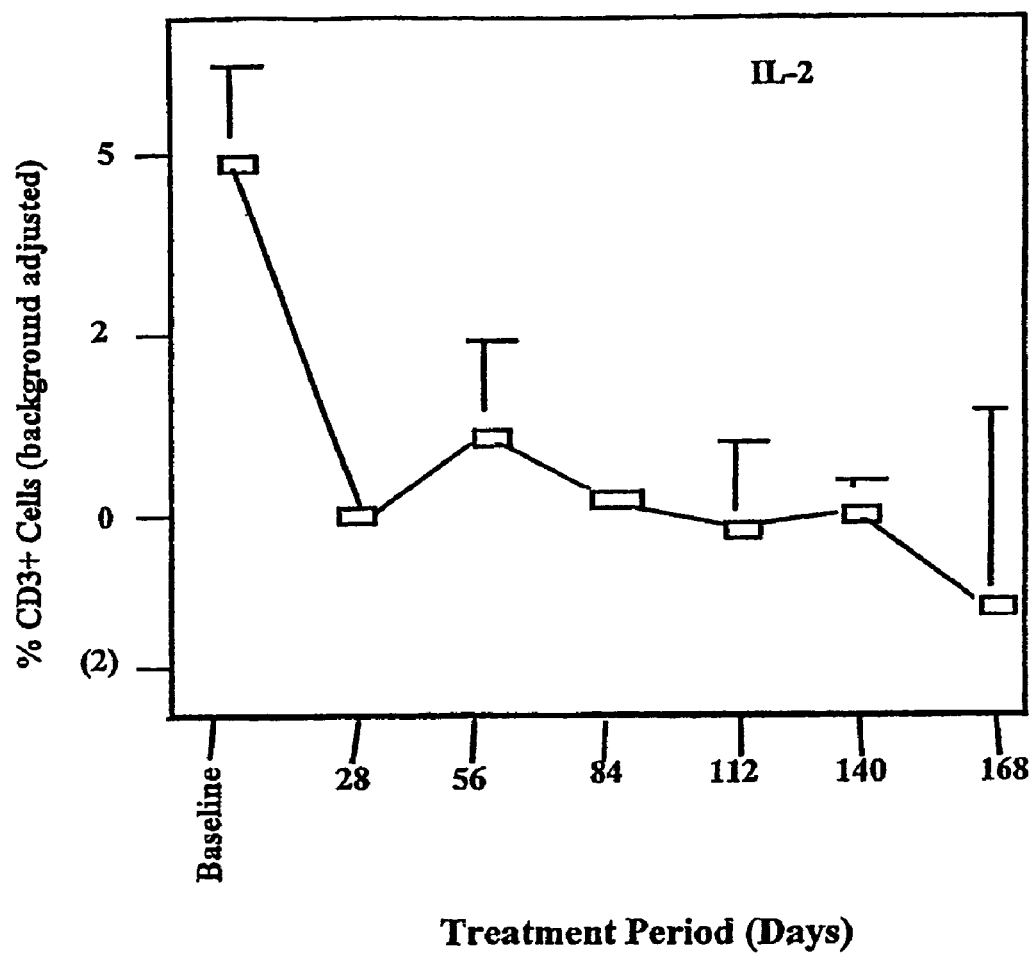
Figure 11C:
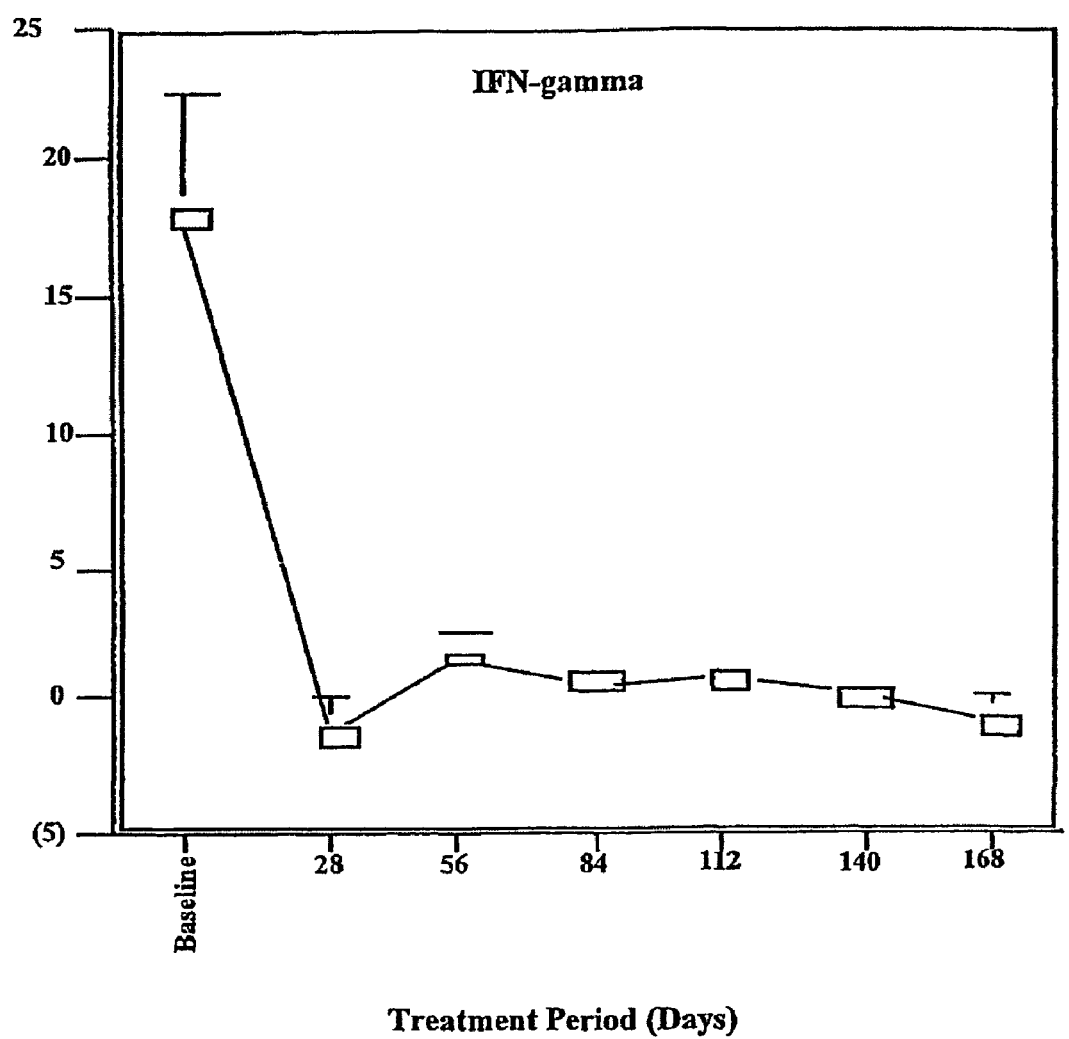
Figure 11D:
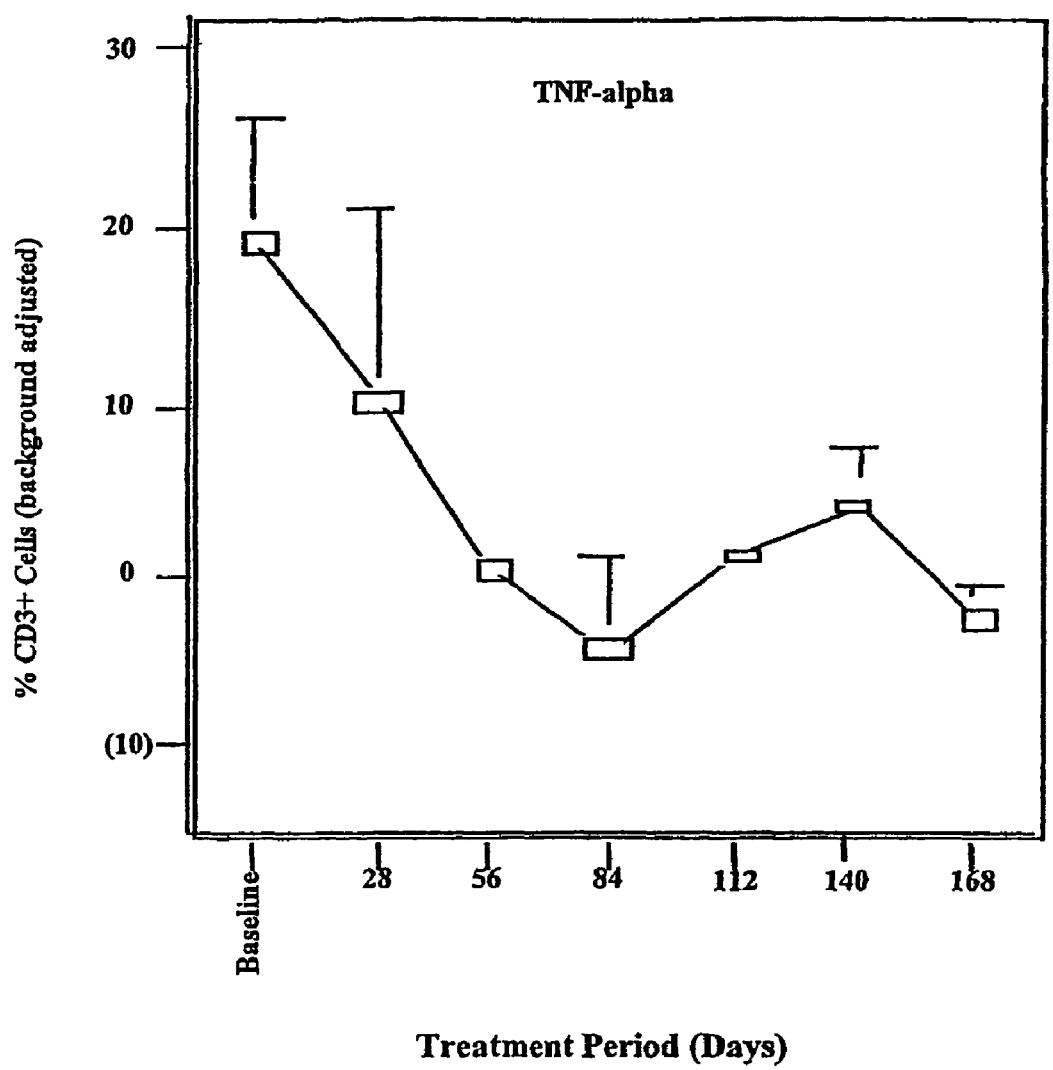
Figure 11E:
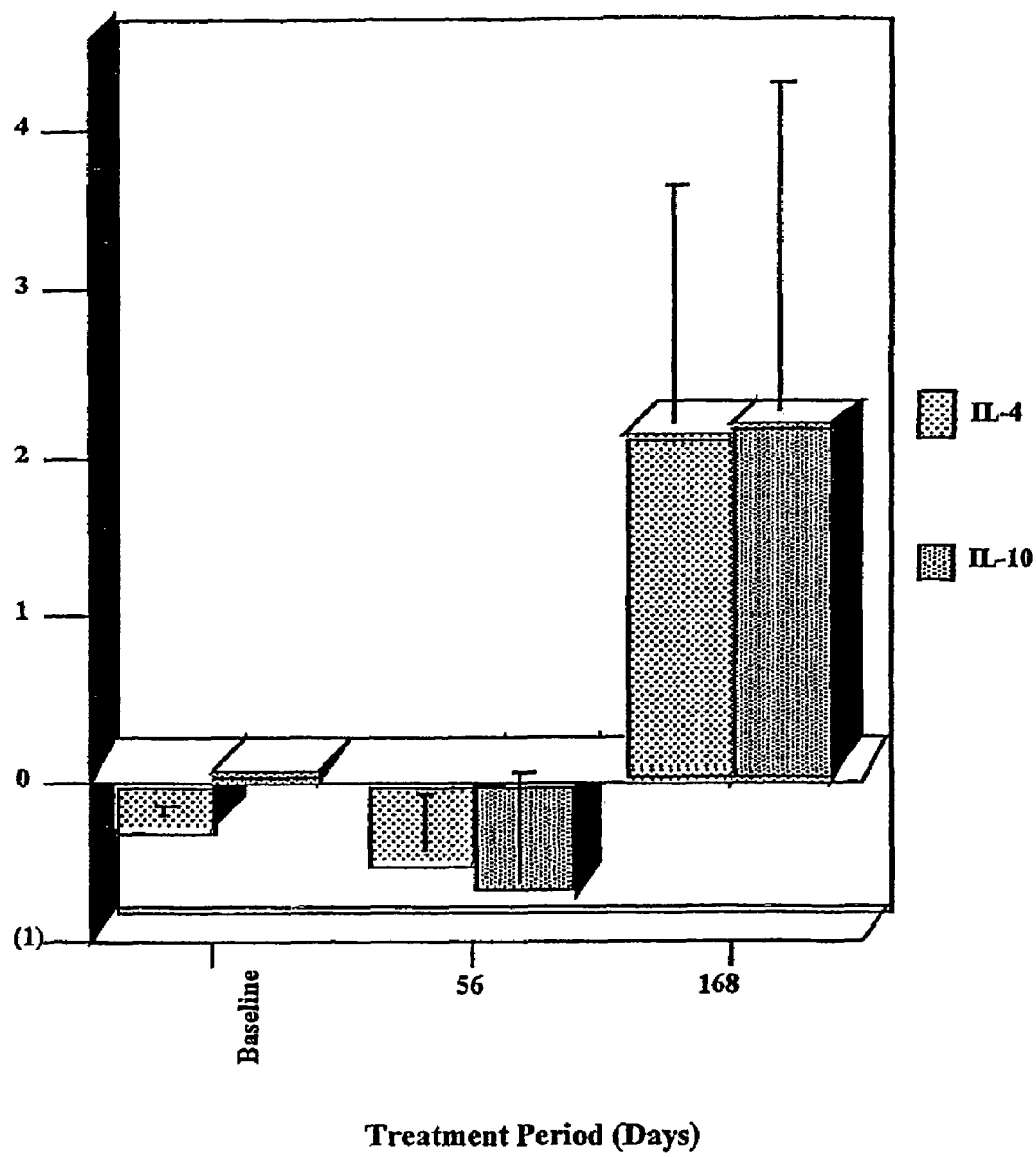
Figure 12A:
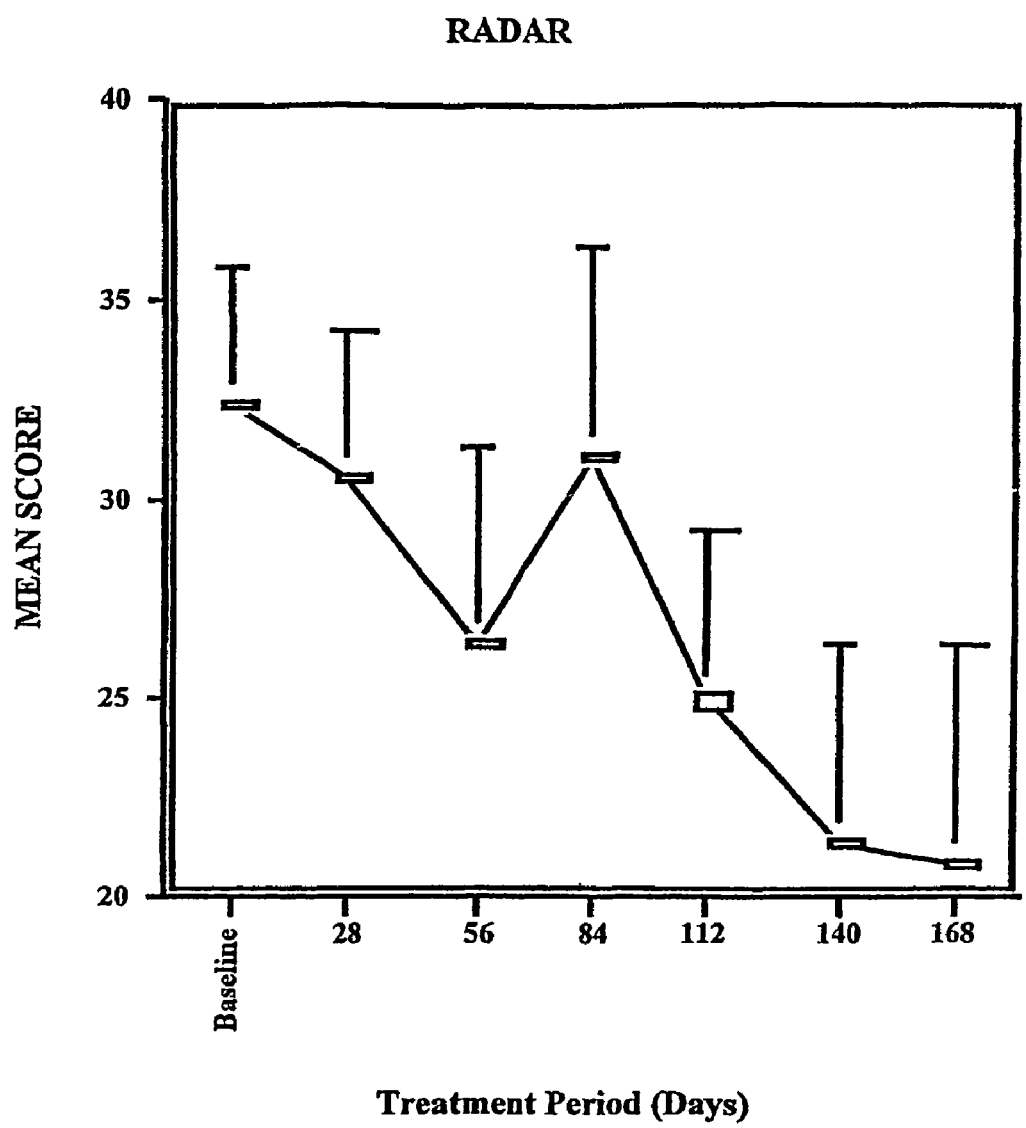
FIG. 12A is a graph showing the results of RADAR questionnaire for the subjects treated with dnaJ peptide. (*=p.<0.05)
Figure 12B:
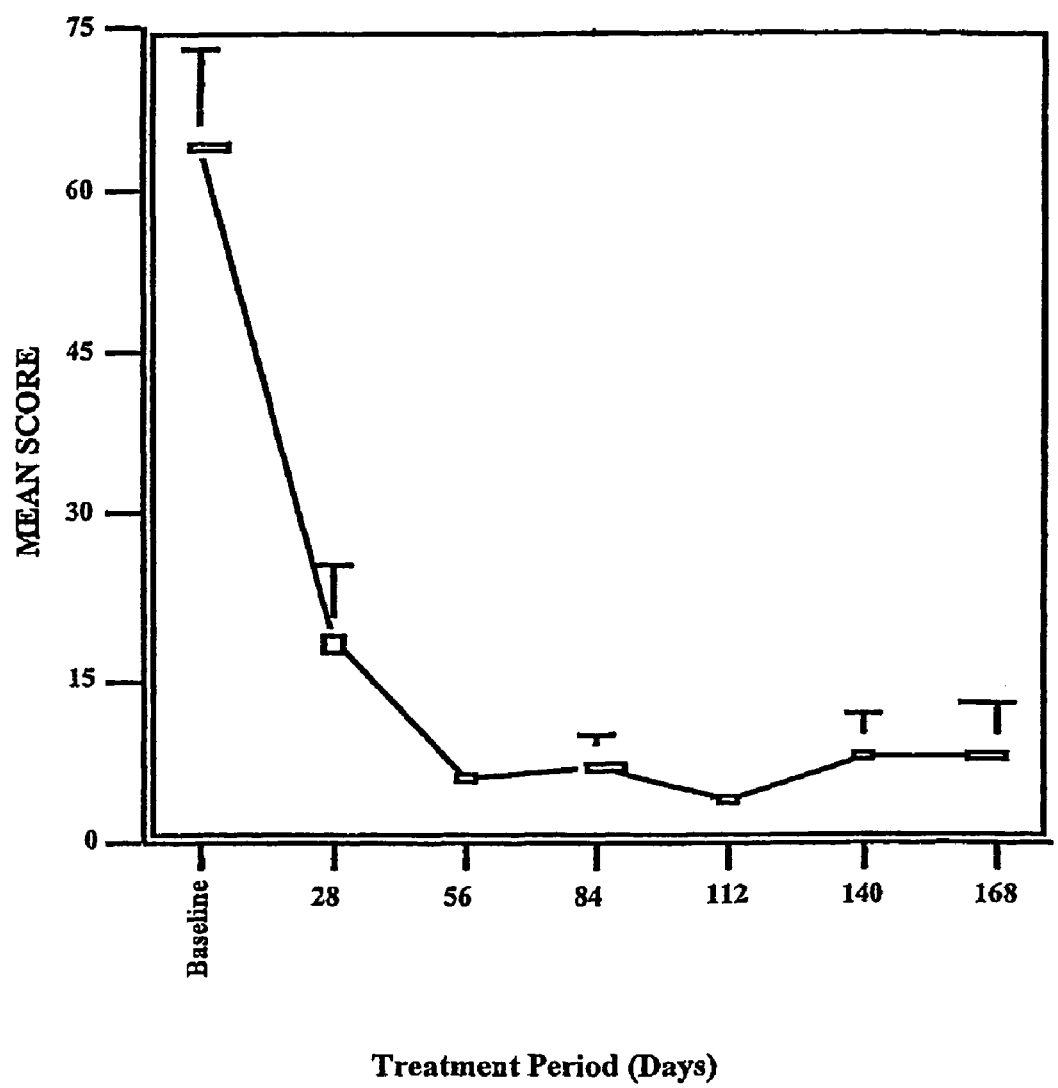
Figure 12:
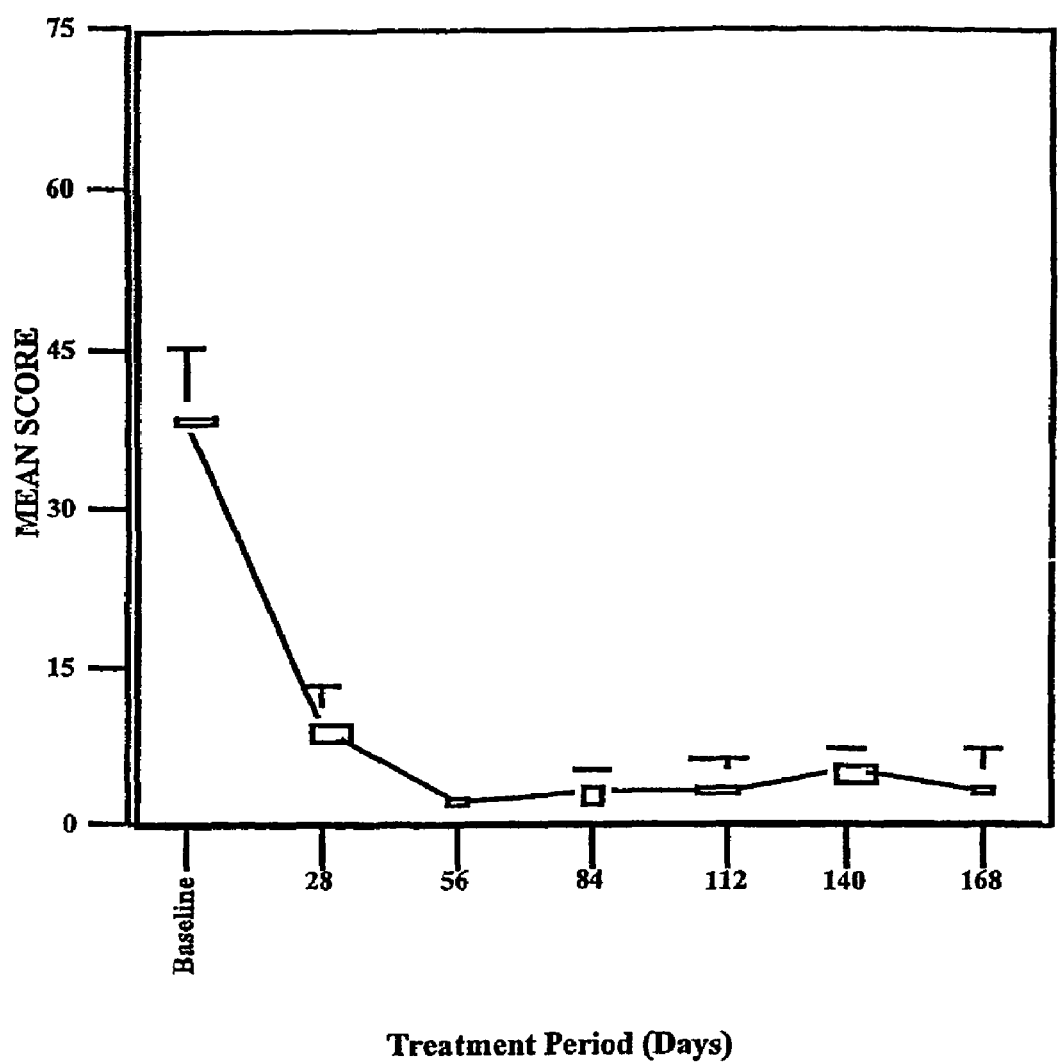
FIGS. 12-B and 12-C show tender joint score and swollen joint score, respectively, from subjects (n=13) treated with dnaJ peptide.
Figure 12D:
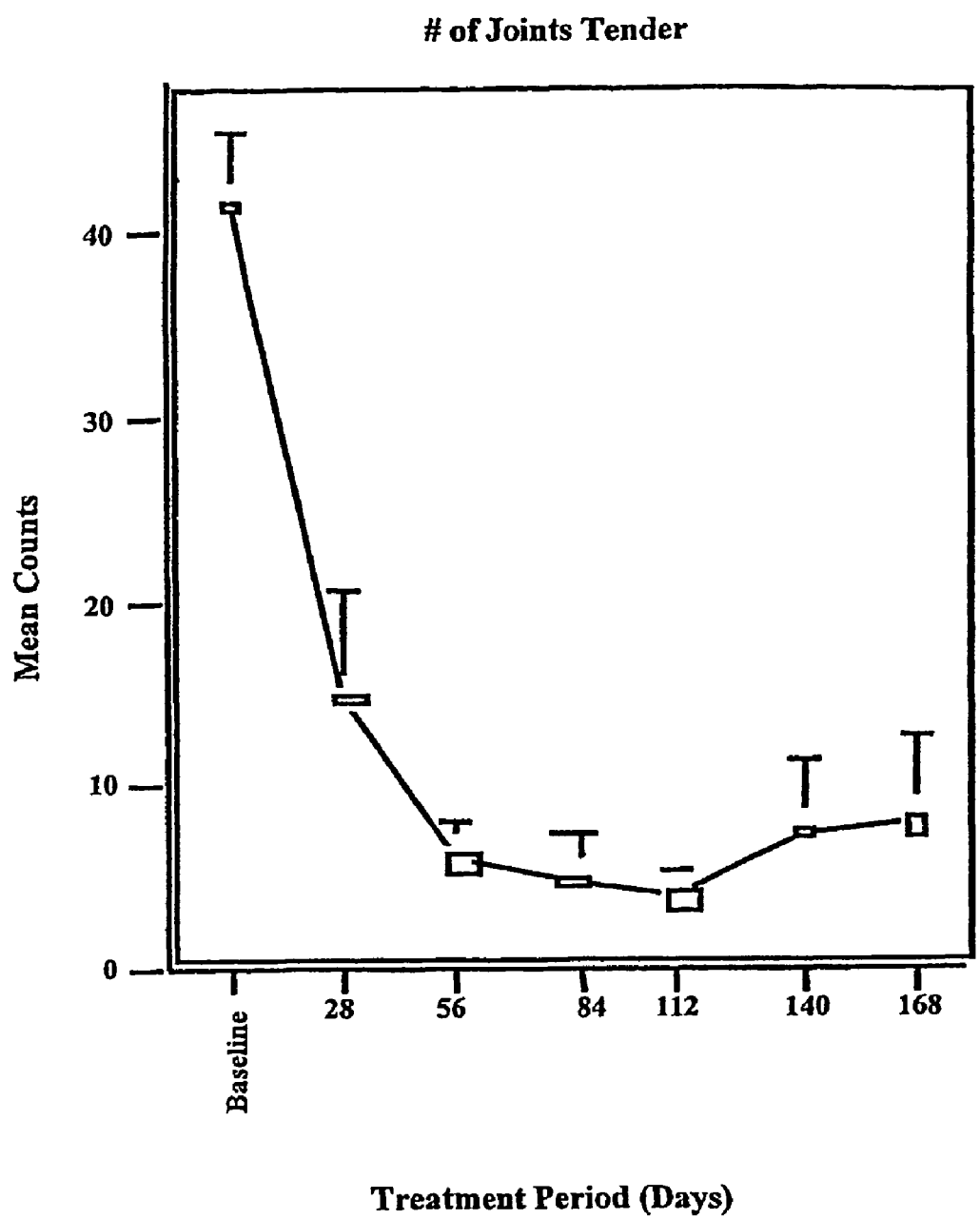
Figure 12E:
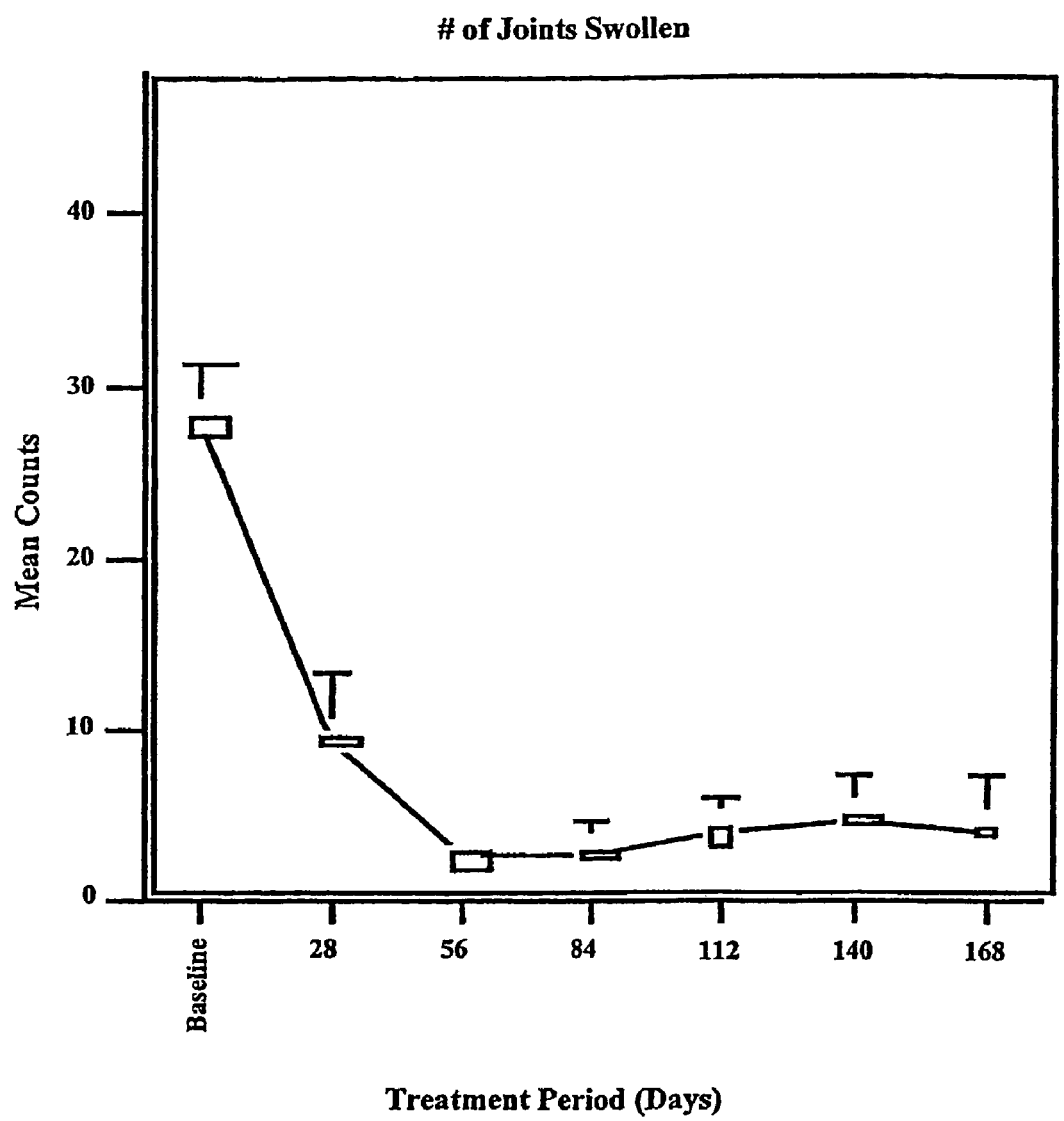

If one compares the identified peptides with peptides that previously have been identified through the rat model of arthritis, the superiority of the method used here becomes evident. In previous studies in the model of adjuvant arthritis, it has been shown that mycobacterial hsp60 peptide containing amino acids 256-270 could induce protection in Adjuvant Arthritis. Following this finding a lot of effort has been put in attempting to identify the presence of 256-270 specific T cells in subjects with JIA. Based on the data provided by the computer algorithm, a new peptide was designed that was compared to the 256-270 aa peptide. This new peptide, mycobacterial hsp60 254-268 (p1) did induce T cell responses as defined by T cell proliferation and cytokine production in a majority of JIA subjects; whereas the 256-270 peptide was not recognized in subjects with JIA. The data are shown in FIG. 10. Thus, using the predicted binding to DR1, DR4 and DR7 has provided a far more efficient way to identify T cell epitopes in subjects with JIA.

EXAMPLE 3

Identification of DNAJP1 as a Pro Inflammatory Epitope in Patients with RA

A peptide from the heat shock protein dnaJ was previously identified as a trigger of T cell proliferation and production of pro-inflammatory cytokines from peripheral blood and synovial fluid cells of RA patients. This peptide (dnaJp1: QKRAAYDQYGHAAFE) (SEQ ID NO: 10), shares sequence homology with the "shared epitope," a five amino acid stretch in common among RA-associated HLA alleles. This study was a Phase I Immune Tolerization study conducted to determine whether in RA interplay between HLA and dnaJ-derived peptides there is maintained and/or stimulation of T cells which participate in autoimmune inflammation. The trial (number "n" of patients who completed=13) was designed in order to adhere to the American College of Rheumatology (ACR) 20 criteria for evaluation of efficacy.

Data from Phase I: The data shown in FIGS. 11A-E and 12A-E stem from a Phase I trial in which a total of 13 human RA patients were treated with three different doses of dnaJP1 qd po for 6 months. In vitro T cell responses to dnaJP1 were monitored at monthly intervals by measuring T cell proliferation and cytokine production in patients treated with dnaJP1 or control molecules. Controls comprised mitogens (PHA) and irrelevant peptides dnaJpV (DERAAYDQYGHAAFE) (SEQ ID NO: 11), an altered ligand peptide that is not stimulatory in patients, and PADRE, a designer pan-DR binder peptide (KXVAAWTLKAA) SEQ ID NO: 12). The results of the T cell proliferative responses from PBMC of seven patients stimulated for 5 days with 10 μg/ml of dnaJP1 peptide are shown in FIGS. 11A-E (evaluations by FASC conducted at monthly intervals). Control experiments (not shown) for the FACS cytokine data analysis of FIGS. 11A-E included FACS measurement of the production of pro inflammatory intracellular cytokines IL-2, IFN-γ and TNF-α from PBMC of 4 patients from the clinical trial that were treated with PADRE. Controls also included FACS measurement of tolerogenic intracellular cytokines IL-4 and IL-10 produced by PBMC of 4 patients from the clinical trial treated with PADRE.

Given the cycling nature of RA, with remission and relapses, and the small number of patients studied, it was important to show that the immune changes found were treatment induced, and not dependent on a more general "state" of activation of a group of patients who, by chance, are cycling together.

FACS measurement was also obtained of tolerogenic intracellular cytokines IL-4 and IL-10 produced by PBMC from 4 untreated patients taken at three different time points and stimulated with dnaJP1. Results of the tolerogenic studies showed that the immune changes shown in FIGS. 11A-E are treatment-specific and treatment-induced.

FIGS. 12A-E show the results of (Rapid Assessment of Disease Activity in Rheumatology, RADAR) tests conducted by patient self-assessment in patients (n=13) stimulated with dnaJP1.

Even though every effort was made to preserve the integrity of the evaluation, it must be emphasized here that the nature of an open label trial like the Phase I herein described can provide only trends regarding treatment efficacy. 84.6% of the patients could be classified as responders according to ACR 20 criteria wherein modulation of the immune response was dimmed down resulting in reduced joint tenderness and swelling.

EXAMPLE 4

Pan DR Binder Peptides Derived from Human and Bacterial HSP60 Proteins are Antigenic in Patients With Rheumatoid Arthritis A computerized algorithm has been applied as discussed above to select potential antigenic peptides from bacterial and human hsp60 sequences (i.e., SEQ ID NOS: 2, 3, 4, 5, 6, 7, 8, 9, 10, 24, 25, 26 or 27). These peptides were designed in order to be Pan HLA DR binders. Certain of these peptides have been tested in different settings and also their effective binding capacity has been tested with excellent correlation between predicted and effective binding ability. These peptides were designed to be true antigens, not merely HLA blocking reagents.

Figure 13A:
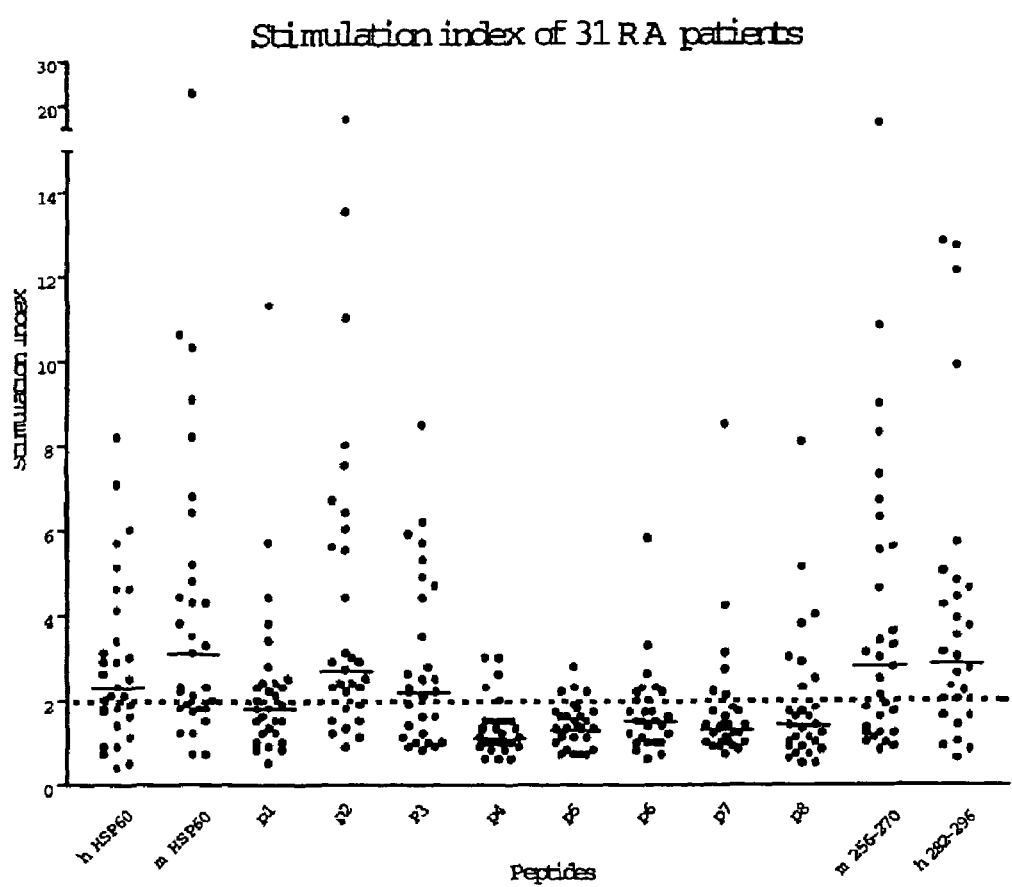
FIGS. 13A and 13B show T cell proliferative responses in patients with RA to human and bacterial hsp60 peptides.
Figure 13B:
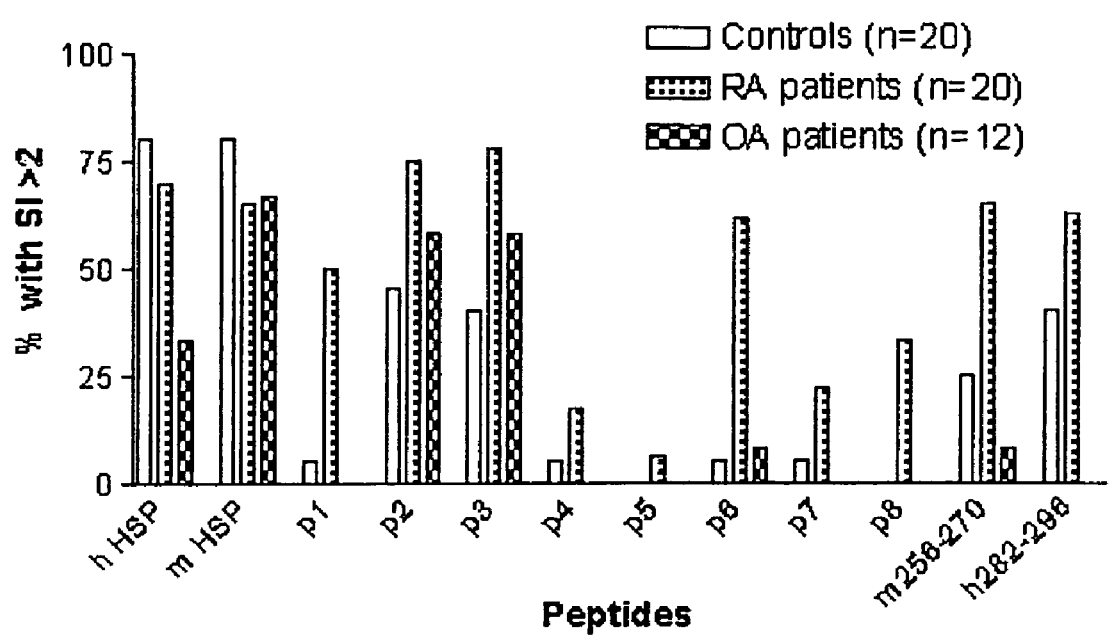

In FIG. 13A, 31 RA patient samples were tested against various of the invention peptides and reactivity was demonstrated with most of the peptide motifs. In FIG. 13B samples of 20 patients with recent onset RA and samples of 12 patients with OA were tested for T cell proliferation to the proteins and to the individual peptides. Results demonstrate the efficiency of the approach in identifying epitopes relevant immunologically to a majority of patients. As shown in FIG. 13A, numerous patients recognized not only human HSP60 (P2, P4, P6, and P8) but also mycobacterial HSP 60 (P1, P3, P5, and P7). This reactivity is also disease specific as indicated in FIG. 13B wherein reactivity between RA, OA and controls is distinct.

EXAMPLE 5

HSP60-Derived Peptides are Triggers of Inflammatory Responses in RA Patients

Figure 14:
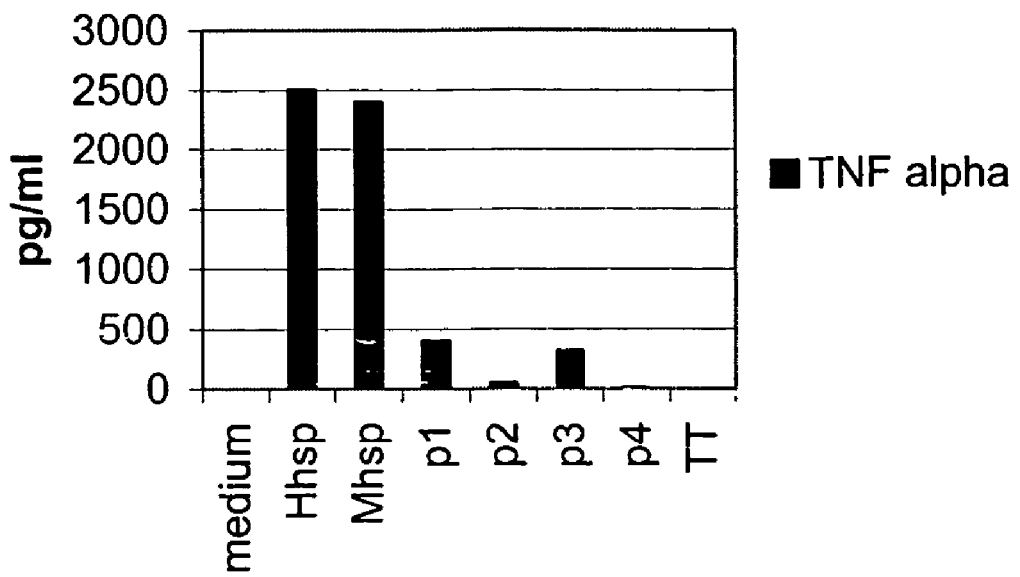
FIG. 14 shows production of TNF-α by PBMC from 6 patients with RA. PBMC were incubated for 72 hours with 10 mg/ml of the antigens. TT is tetanus toxoid. TNF-α was measured in supernatants by ELISA.

Immune recognition of hsp60-derived peptides also leads to production of proinflammatory cytokines, such as TNFα. Conversely, IL-10 production appears to be close to background levels in the same samples. As shown in FIG. 14, TNFα is stimulated. Contrarily, IL-10 is not stimulated (data not shown). This finding is of particular interest considering the already documented role which hsp60 has in induction of TNFα production by non-T cells, upon engagement of TLR receptors. This Example discloses the role played by hsp60 in regulation of innate and adaptive immunity. The data suggests an IL-10 dependent mechanism of modulation of human autoimmunity based on recognition by regulatory type cells of human derived heat shock protein peptides. Further, these findings are in accordance with the proposed concept of the modulatory role played in autoimmune inflammation by responses to heat shock proteins. A sequential chain of events could be generated by initial recognition of bacterial derived peptides and production of pro-inflammatory cytokines. Remission from inflammation may be associated with prevalent recognition of human derived peptides. These results show that it is possible to exploit this natural "dimmer" of inflammation for therapeutic purposes, by identifying peptides suitable to regulate inflammation.

Figure 18A:
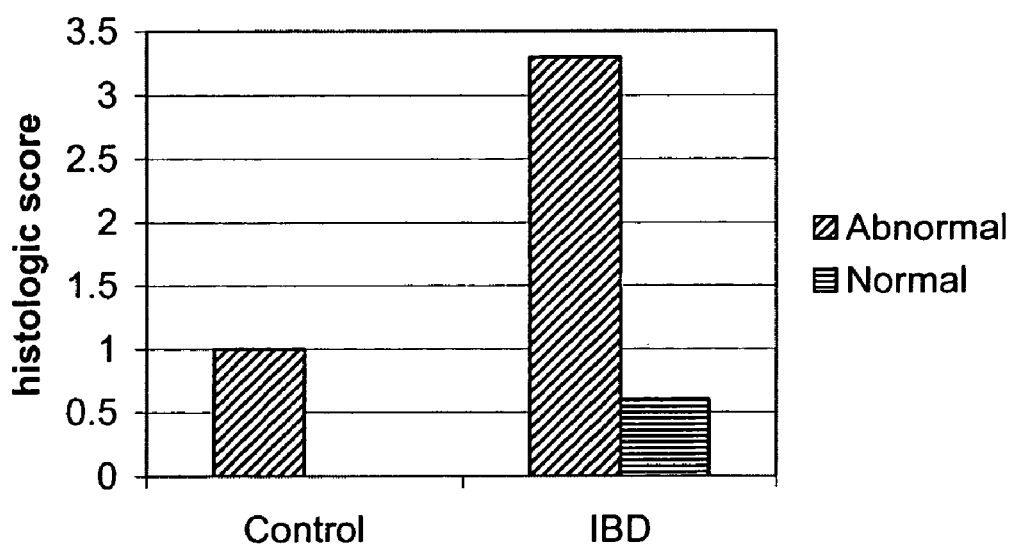
FIGS. 18A-G show average histologic score (by intensity of the response as indicated by the graph bars) between control patients and those diagnosed with IBD.
Figure 18B:
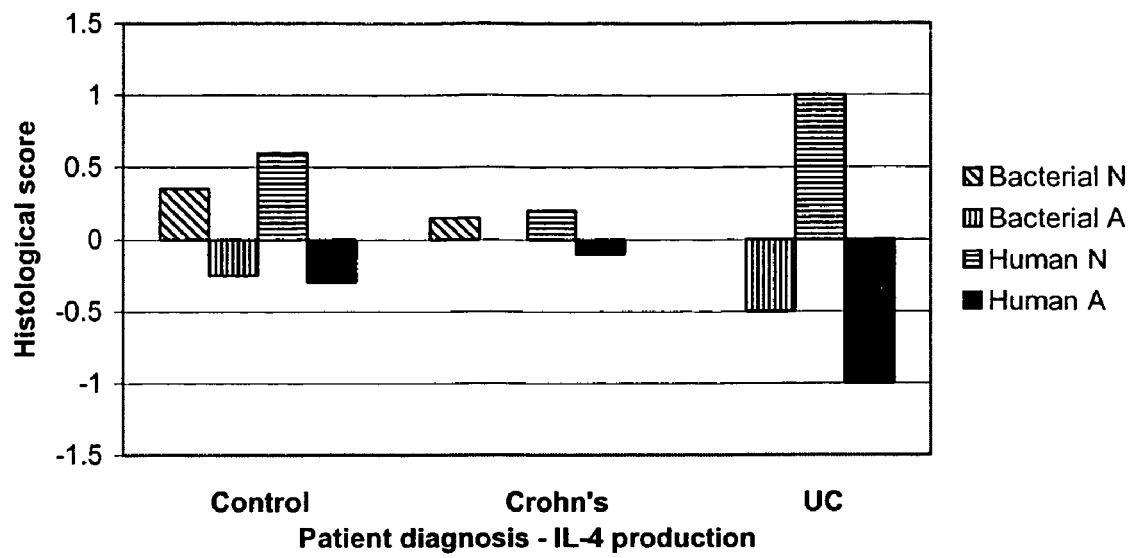
Figure 18C:
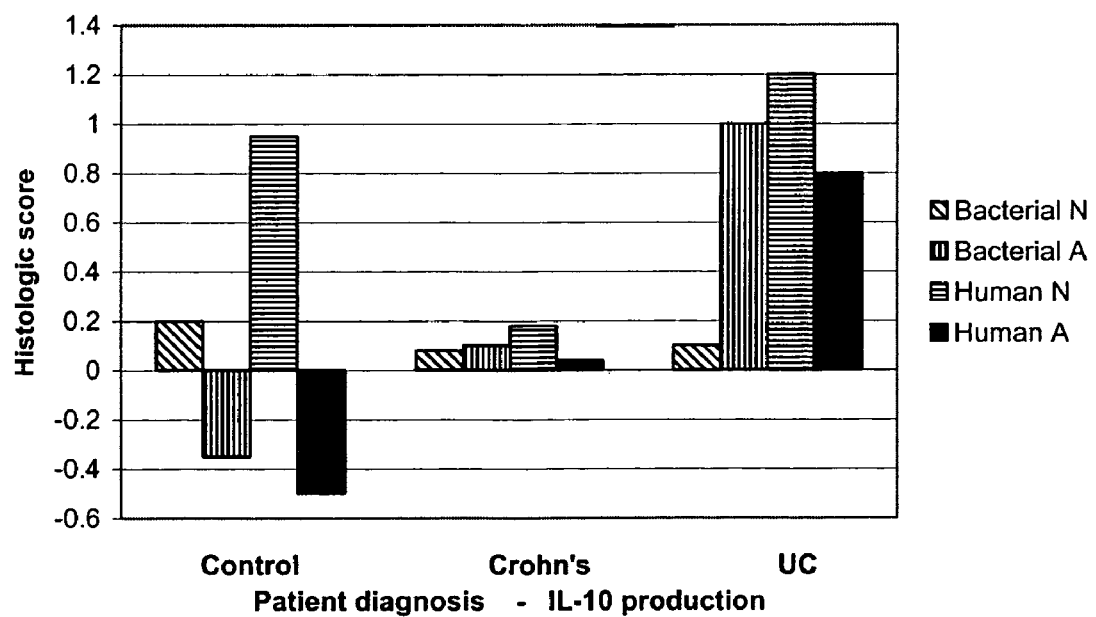
Figure 18D:
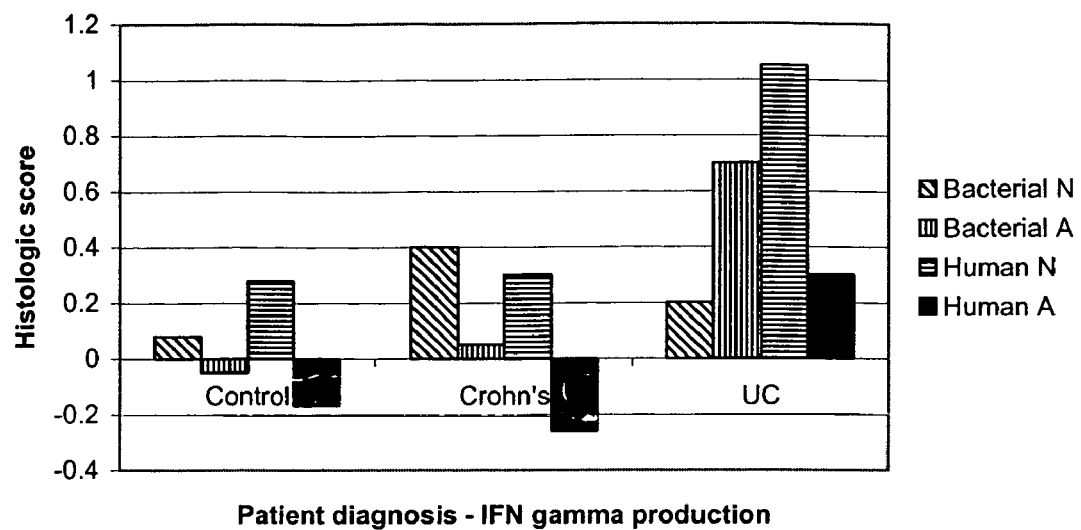
Figure 18E:
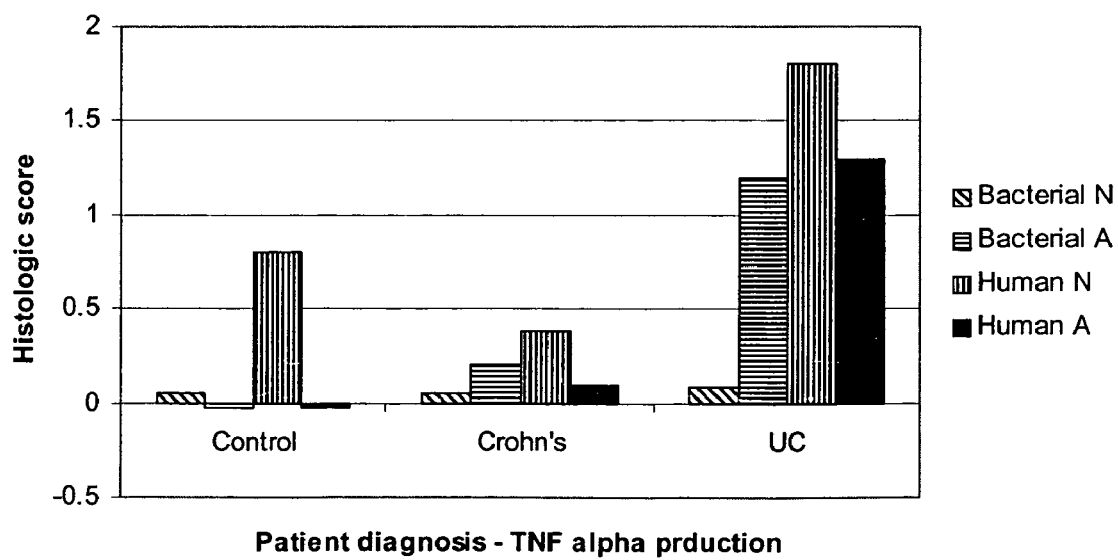
Figure 18F:
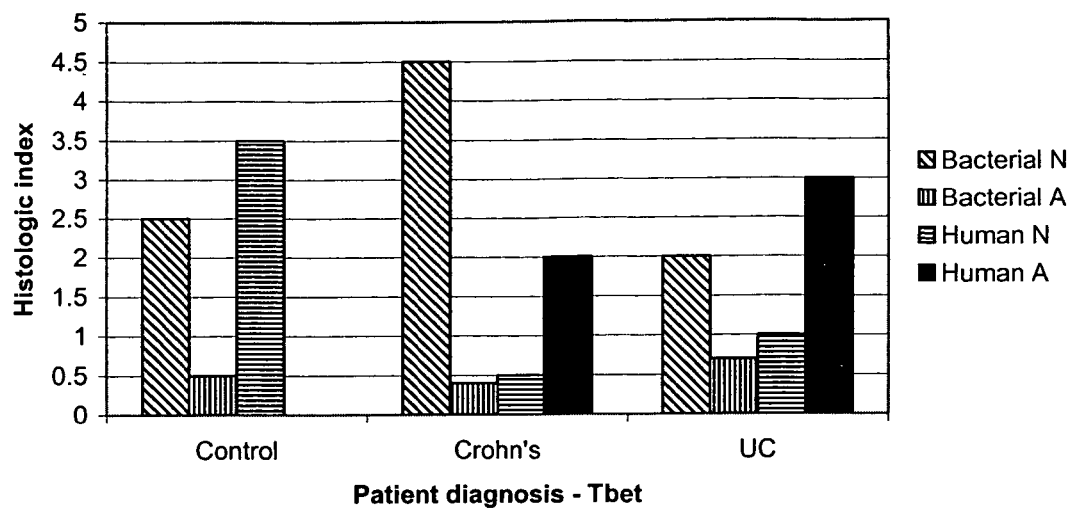
Figure 18G:
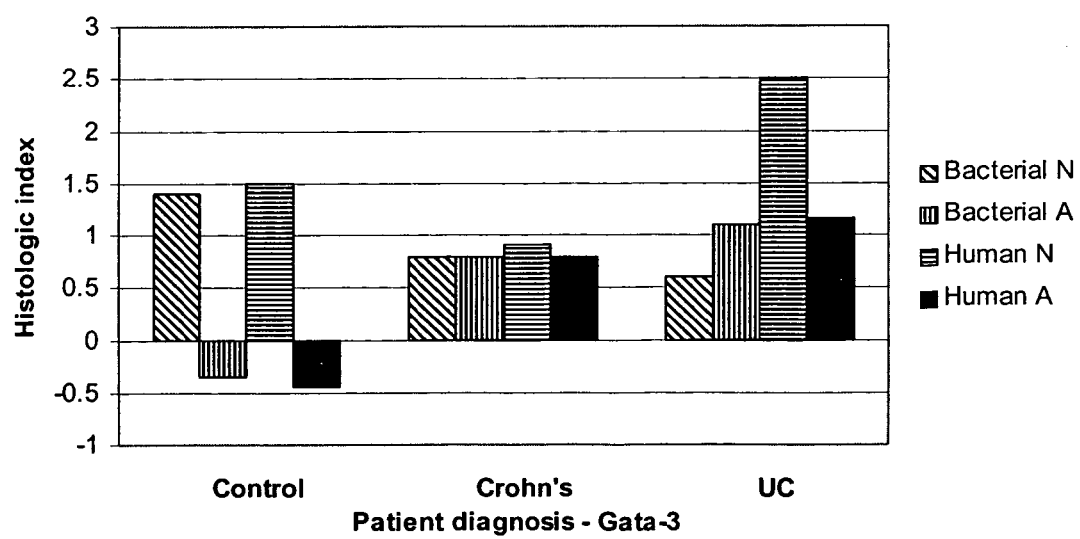

In summary, the analysis of T cell responses showed:

i) That this approach is extremely effective at identifying from hundreds of potential candidates those peptides, which are relevant to a given immunological process;

ii) That T cell recognition of bacterial/human homologous sequences may be associated with generation of pro-inflammatory responses;

iii) That regulatory mechanisms, based on production of IL-10 by Tr-1 type cells, are present in recognition of human sequences (FIG. 18B, C, G). Altogether, these results provide strong support to the concept that responses to hsp play a modulating role in autoimmune inflammation.

EXAMPLE 6

Figure 15:
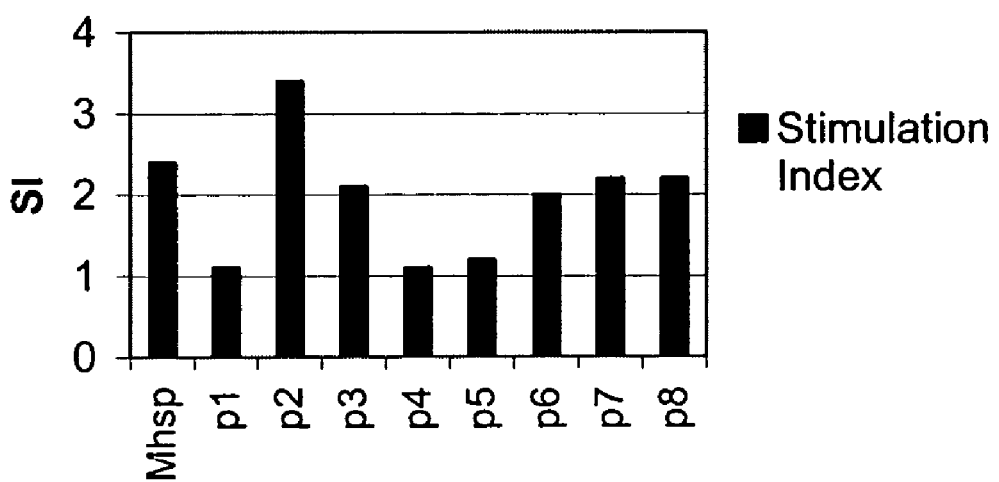
FIG. 15 is a graph showing T cell proliferative responses in patients with pediatric SLE to human and bacterial hsp60 peptides of FIG. 5. SI: Stimulation Index. (y-axis).

Identification of Pan DR Binder Peptides Derived from Human and Bacterial HSP60 Proteins are Antigenic in Pediatric SLE Patients In this Example, 11 children with Systemic Lupus Erythematosus (SLE) were studied wherein a sample of 5 children with recent onset SLE were tested for T cell proliferation to the various peptides of the invention as disclosed above in Table I. FIG. 15 demonstrates the efficiency of the approach in identifying relevant epitopes.

Figure 16A:
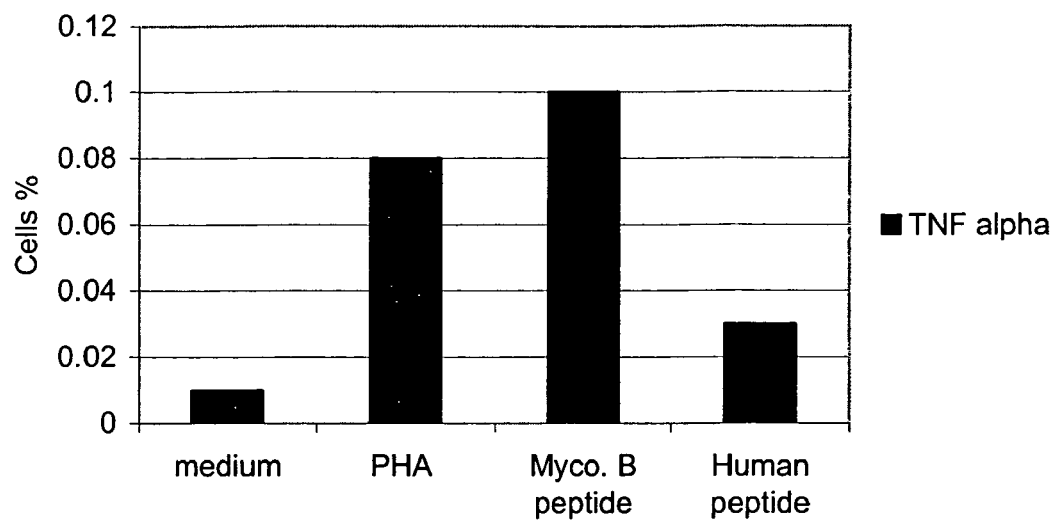
FIGS. 16A and B show T cell responses to bacterial and human hsp60 derived peptides. PBMC from 6 patients with pediatric SLE were stimulated for 72 hours with human or bacterial peptides, which were pooled in two peptide pools (human: p2, p4, p6, p8; and bacterial: p1, p3, p5, p7) at a final concentration of 10 mg/ml. TNF-α (FIG. 16A) or IFN-γ (FIG. 16B) production was measured by intracellular cytokine staining and FACS analysis on CD3+ gated cells. Y axes represent percent of CD3+/cytokine positive T cells.
Figure 16B:
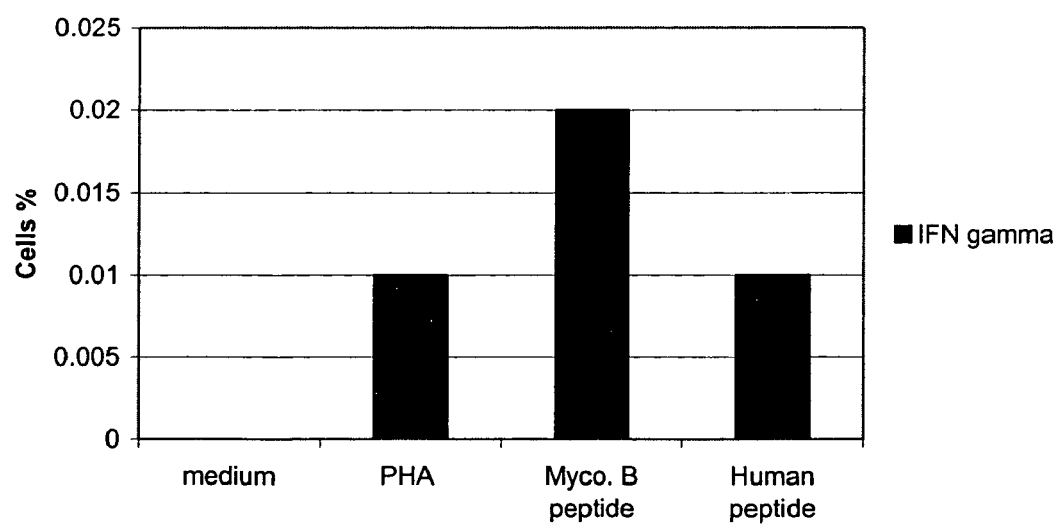

As shown in FIGS. 16A and B, T cells of 6 patients with pediatric SLE recognized mycobacterial hsp60 derived peptides leading to production of pro-inflammatory cytokines TNFα and IFNγ. Response to human homologues was only marginal. This finding is in accordance with the proposed concept of the modulatory role played in autoimmune inflammation by responses to heat shock proteins in inflammation. A sequential chain of events could be generated by initial recognition of bacterial derived peptides and production of pro-inflammatory cytokines. Remission from inflammation may be associated with prevalent recognition of human derived peptides through the "dimming down" of the pro-inflammatory response by activation of regulatory T cells. This is a further indication that the present invention is capable of exploiting this natural "dimmer" of inflammation for therapeutic purposes, by identifying peptides suitable to regulate inflammation.

EXAMPLE 7

Responses to Pan DR Binder Peptides in Juvenile Dermatomyositis

Figure 17:
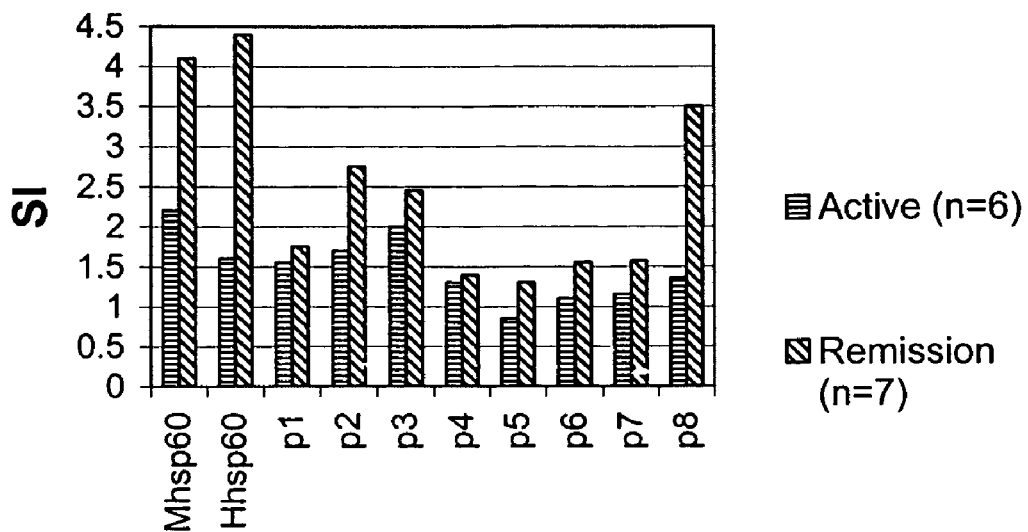
FIG. 17 is a graph showing T cell proliferative responses of PBMC from patients with Juvenile Dermatomyositis (JDM) towards the hsp60 bacterial and human peptides of FIG. 5. Patients in remission (n=7); patients with active JDM (n=6).

This example identifies in another pediatric disease a peptide from the pool whose recognition triggers regulatory type T cells. Thirteen patients with a definite diagnosis of JDM according to standard disease criteria, were included in this study. Peripheral Mononuclear Cells (PBMC) were cultured for 96 hours with the following antigens: Mycobacterial hsp60 (myc hsp60), Human hsp60 (Hum hsp60), and Pan DR binding peptides p1-p8. All antigens were cultured at 10 micrograms/ml. After 96 hours thymidine incorporation was measured. The results are expressed in FIG. 17 as stimulation index (SI). SI is defined as counts per minute (cpm) thymidine incorporation in cells cultured with an antigen divided by cpm of cells cultured in culture medium without antigen. As shown in FIG. 17, X axis represents the different antigens; the Y axis represents the SI. Bars represents the mean SI for PBMC from JDM patients with either active disease or incomplete clinical remission. For example, P8, a human peptide, is recognized by the patients during disease remission which recognition is associated with immune modulation and control of the disease mechanism.

EXAMPLE 8

Responses to Pan DR Binders in Inflammatory Bowel Disease

Inflammatory bowel disease (IBD), which includes Crohn's disease (CD) and ulcerative colitis (UC), is a is a lifelong condition that may affect up to 50 per million children in the population. It is generally accepted that the origin of the damage in IBD is mediated by a disregulation of the immune system. Despite rigorous investigation, the processes responsible for causing and maintaining the chronic inflammation remains unknown. Although IBD aetiopathogenesis has been studied extensively, it remains difficult to find a curative treatment. Currently recommended therapy is non-specifically immunosuppressive. As indicated by this Example, a better understanding of T cell mediated events controlling immunity could provide targets for specific immunotherapy. These studies show that immunological responses to bacterial HSPs are implicated in the pathogenesis of autoimmunity in animals and humans for this disease. HSPs are present at the site of inflammation. Hence the findings suggest that potentially pathogenic responses are initially triggered by the encounter of the immune system of the host with proteins of bacterial origin, and subsequently perpetuated by recognition of self homologues. This cross reactivity may be part of the chronic inflammation process. Sets of peptides from two bacterial/human pairs of HSP: hsp65/60 and *E. coli* dnaJ/hdnaJ have recently been identified by the present inventors. Recognition of the uniquely human peptides by patients with autoimmune diseases has been found to be is associated with a down regulation of the inflammatory process and better prognosis. Uniquely bacterial peptides, on the contrary, are triggers of pro-inflammatory responses. Hence, a "molecular dimmer," i.e., a mechanism which may naturally regulate the level of immune inflammation may have been identified. It is proposed that this same mechanisms may work for IBD.

This data shows that there are indeed abnormal responses to HSPs in patients with IBD. Such responses seem to be involved in aetiopathogenesis and may represent likely targets of immune therapy. 4 normal patients and 6 patients diagnosed with IBD were tested. Patients were split between Crohn's Disease and Ulcerative Colitis. Cytokine profile data show pro-inflammatory responses (i.e. production of pro-inflammatory cytokines IFN-γ and TNF-α and reduced production of anti-inflammatory cytokine IL-4 to the bacterial peptides from patients with IBD. (See FIGS. 18A-G). The immune response in UC and CD showed a different recognition pattern of candidate peptides and generated a network of pro-inflammatory and tolerogenic responses. A negative correlation between a broad spectrum of peptides and clinical activity was identified in UC patients. Significantly, in CD patients a clear correlation between response to specific peptides and both disease activity and histologic inflammation was demonstrated. These data suggest a pathogenic role played by epitopes of bacterial and human hsp at the site of inflammation. (see Tables 2-5 below)

TABLE 2

Clinical characteristics of patients and controls.

|  | UC | CD | UC + CD | controls |
|---|---|---|---|---|
| number | 7 | 9 | 16 | 10 |
| age (yrs) | 11.5 | 12.2 | 11.6 | 9.4 |
| gender (M/F) | 3/4 | 5/4 | 8/8 | 6/4 |
| ethnicity: |  |  |  |  |
| white | 3 | 8 | 11 | 7 |
| hispanic | 3 | 1 | 4 | 2 |
| african-american | 1 | 0 | 1 | 0 |
| asian | 0 | 0 | 0 | 1 |

TABLE 3

Mean Pediatric Crohn's Disease Activity Index (PCDAI) and Histologic Score (HS) in UC and CD patients.

|  | UC | CD | UC + CD |
|---|---|---|---|
| PCDAI (0-110) | 23.9 (range 5-37.5) | 25.8 (range 5-47.5) | 24.9 (range 5-47.5) |
| HS (0-12) | 7.1 (range 3.5-11) | 5.6 (range 0-9) | 6.2 (range 0-11) |

TABLE 4

Correlation between PCDAI and peptide induction (r).

|  |  | peptide1 | peptide3 | peptide5 | peptide7 | peptide2 | peptide8 |
|---|---|---|---|---|---|---|---|
| CD | IFNg | 0.0706 | −0.1154 | −0.0382 | 0.795 | 0.7600 | 0.7952 |
|  | TNFa | 0.1107 | −0.1188 | 0.1611 | 0.8268 | 0.6756 | 0.8268 |
|  | IL4 | 0.4048 | −0.083 | 0.322 | 0.5944 | 0.4957 | 0.8019 |
|  | IL10 | 0.1331 | −0.2146 | 0.2597 | 0.8302 | 0.5209 | 0.8571 |
| UC | IFNg | −0.4539 | −0.6917 | −0.7928 | −0.8521 | −0.7421 | −0.7812 |
|  | TNFa | −0.5138 | −0.6548 | −0.6891 | −0.6948 | −0.6915 | −0.6995 |
|  | IL4 | −0.5181 | −0.9281 | −0.8013 | −0.479 | −0.7664 | −0.8784 |
|  | IL10 | −0.5385 | −0.5805 | −0.6849 | −0.7033 | −0.6792 | −0.8196 |

TABLE 5

Correlation between HS and peptide induction (r).

|    |      | peptide1 | peptide3 | peptide5 | peptide7 | peptide2 | peptide8 |
|----|------|----------|----------|----------|----------|----------|----------|
| CD | IFNg | −0.5081  | 0.3617   | 0.4708   | 0.5837   | 0.7822   | 0.3746   |
|    | TNFa | −0.3906  | 0.3455   | 0.6377   | 0.4876   | 0.6088   | 0.3723   |
|    | IL4  | −0.063   | 0.4296   | 0.8705   | 0.7156   | 0.7143   | 0.3984   |
|    | IL10 | −0.288   | 0.3423   | 0.7577   | 0.5349   | 0.6665   | 0.5045   |
| UC | IFNg | 0.2563   | 0.2551   | 0.0362   | 0.0007   | −0.1787  | −0.0997  |
|    | TNFa | 0.6323   | 0.1145   | −0.1039  | 0.6243   | −0.1769  | −0.036   |
|    | IL4  | −0.4052  | −0.2158  | −0.2582  | 0.189    | −0.3078  | −0.2496  |
|    | IL10 | 0.2243   | 0.3088   | 0.0068   | −0.0032  | −0.0906  | −0.0736  |

EXAMPLE 9

Epitope-Specific Immunotherapy Induces Immune Deviation of Proinflammatory T Cells in Rheumatoid Arthritis Abbreviations: RA, rheumatoid arthritis; PBMC, peripheral blood mononuclear cell; TNF, tumor necrosis factor; FACS, fluorescence-activated cell sorter; aAPC, artificial antigen presenting cell; CTB, Cholera toxin subunit B; NA, neutravidin; TCC, T cell capture; Ct, threshold cycle; Treg, cells with a regulatory function.

In one embodiment of the invention, the ability to modulate, on demand, epitope-specific immune responses represents a major addition to available therapeutic options for many autoimmune diseases. For example, in one embodiment of the current invention, immune deviation is induced by mucosal peptide-specific immunotherapy. As shown in this Example 9, this method of immunotherapy is applicable to such disease targets as rheumatoid arthritis (RA). Specifically, with respect to treatment of RA, methods of the invention provide an ability to detect low-affinity class II-restricted peptide-specific T cells and ultimately provide a change from, for example, proinflammatory to regulatory T cell function, including significant induced production of IL-4 and IL-10, and a concomitant significant decrease in dnaJP1 induced T cell proliferation and production of IL-2, IFN-β, and TNF-α.

In an experiment further disclosed below, the total number of dnaJP1-specific cells did not change over time, whereas expression of foxP3 by CD4+CD25 bright cells increased, suggesting that the treatment affected regulatory T cell function. Thus, rather than clonal deletion, the observed change in immune reactivity to dnaJP1 was the outcome of treatment-induced emergence of T cells with a different functional phenotype. In other words, the invention methods provided for a shift from a Th-1 response to a Th-2 response in the same cell population.

The clinical model, Rheumatoid Arthritis, used in this immune intervention Example is representative of autoimmune disorders as set forth elsewhere in this disclosure. The peptide used, (dnaJP1), is derived from the bacterial heat shock protein dnaJ and shares sequence homology with the shared epitope, a 5-aa stretch in common among RA-associated HLA alleles. We proposed that in RA an interplay between HLA and dnaJ-derived peptides maintains and stimulates T cells, which participate in autoimmune inflammation. Modulation of this pathway may affect the autoimmune process and thus, be biologically as well as clinically relevant. We designed a pilot clinical trial to obtain information regarding both safety and immunological efficacy of the treatment. Enrollment criteria for this study included active RA as defined by the American College of Rheumatology, a disease duration <5 years and in vitro responsiveness to dnaJP1, defined as T cell proliferation and/or production of proinflammatory cytokines. DnaJP1 was given orally for 6 months. A total of 66.7% of the patients screened met both clinical and immunological entry criteria; 15 patients divided in three different dose groups (0.25, 2.5, and 25 mg daily) were included in the trial (Tables 6 and 7 below). Medical evaluation, including routine laboratory tests and immunological analyses, took place monthly. The objectives of the study were to evaluate tolerability and biological efficacy of the treatment on the immune system of the patients, with particular attention to dnaJP1-specific T cells.

TABLE 6

General characteristics of patients enrolled and inclusion criteria for the study

|                                          | Value        |
|------------------------------------------|--------------|
| General characteristics                  |              |
| Age, years                               | 48.8 ± 3.4   |
| Sex, M/F                                 | 3/12         |
| Disease duration, years                  | 2.8 ± 0.5    |
| HLA DRB1*0401                            | 6/15         |
| Inclusion criteria                       |              |
| Clinical                                 |              |
| American College of Rheumatology criteria | 15/15       |
| Immunological (dnaJP1-induced)           |              |
| T cell proliferation                     | 7/12         |
| IL-2 production                          | 6/15         |
| IFN-γ production                         | 8/15         |
| TNF-α production                         | 6/15         |

Reason for withdrawal study initiation second-line drugs, development Reiter-like syndrome.

TABLE 7

DnaJP1-specific T cell reactivity

| Proliferation (stimulation index) (Percent CD3+/cytokine+) | Day 0 | Day 56 | Day 168 |
|---|---|---|---|
|  | 2.6 ± 0.5 | 1.0 ± 0.1* | 0.8 ± 0.1* |
| IL-2 | 2.1 ± 1.5 | 1.4 ± 1.1 | −1.5 ± 2.1 |
| IFN-γ | 11.0 ± 3.7 | 2.5 ± 1.3* | −1.9 ± 1.3* |
| TNF-α | 9.7 ± 3.9 | 0.3 ± 0.5* | −1.7 ± 1.0* |
| IL-4 | −0.3 ± 0.4 | 0.9 ± 1.0 | 3.3 ± 1.2* |
| IL-10 | −1.1 ± 1.2 | 0.2 ± 0.1 | 2.0 ± 1.1* |

*P_0.001 vs. baseline.

Methods

Patients. Eligible patients fulfilled the 1987 revised American College of Rheumatology criteria for RA, had a disease duration of <5 years, had active disease as manifested by at least six joints that were swollen and tender, and had in vitro responsiveness to dnaJP1, defined as any of the following criteria: T cell proliferation expressed as stimulation index >2 and/or production of proinflammatory cytokines expressed as >2% above background of CD3+ T cells producing IFNγ, tumor necrosis factor (TNF)-α, or IL-2 measured by intracellular fluorescence-activated cell sorter (FACS) analysis. Institutional Review Board approval and informed consent was obtained in accordance with regulations. Fifteen patients were included in the study (Tables 6 and 7) and were treated for 6 months with dnaJP1 at three different dosages: 0.25, 2.5, and 25 mg. Patients were evaluated every month for a standardized clinical examination (joint scores for swelling and tenderness, Rapid Assessment of Disease Activity in Rheumatology scores), standardized laboratory tests (erythrocyte sedimentation rate, rheumatoid factor, C-reactive protein, and serum chemical values), and an immunological checkup.

T Cell Proliferation Assays. Peripheral blood mononuclear cells (PBMCs) were cultured in triplicate in 200 ml u-shaped bottom wells (Costar, Cambridge, Mass.) at 5×10$^5$ cells per well for 120 h with or without antigen. Phytohaemagglutinin (2 mg/ml) was used as a positive control. For the final 16 h, cells were pulsed with [3H]thymidine (Amersham Pharmacia International, Bucks, United Kingdom). Thymidine uptake was measured by using a liquid scintillation counter. Results are expressed as a mean cpm of triplicate cultures. The magnitude of the response is expressed as stimulation index: the mean cpm of stimulated/nonstimulated cultures.

Antigens. Peptides were synthesized as C-terminal amides and were purified by reversed-phase HPLC. Peptides were N-biotinylated during synthesis (only one biotin molecule per peptide, 100% biotinylation; Synthetic Biomolecules, San Diego). The following peptides were used: dnaJP1 (QKRAAYDQYGHAAFE) (SEQ ID NO. 10), dnaJPv (DERAAYDQYGHAAFE) (SEQ ID NO. 11), PADRE (+) (KJVAAWTLKAA-a) (SEQ ID NO. 34), and PADRE (−) peptide (UAJAAAATLKAA) (SEQ ID NO. 35) (10 mg/ml). dnaJPv is identical to dnaJP1 except for the two N-terminal amino acids. In contrast to dnaJP1, dnaJPv does not induce a proliferative T cell response in patients with RA. It was therefore used as negative control in the proliferation assays. PADRE (+) has good pan-DR binding and antigenic properties, and it has therefore been used as positive control in measuring cytokine production by intracellular FACS analysis. PADRE (−) has a comparable pan-Dr binding capacity but is a poor antigen. It has been therefore used as negative control to identify background in the T cell capture (TCC) assay.

Preparation of Artificial Antigen-Presenting Cells (aAPCs). This preparation is a modification from our published method. Briefly, phosphatidylcholine and cholesterol (Sigma) are combined in a glass tube at a molar ratio of 7:2. The solvent is evaporated under an Argon stream for 30 min and is dispersed at a final concentration of 10 mg/ml in 140 mMNaCl and 10 mM Tris-HCl, pH 8 (buffer A) containing 0.5% sodium deoxycholate. Monosialoganglioside-GM1 (Sigma G-7641) is added at a final concentration of 0.28 or 0.55 mM. The solution is sonicated until clear and is stored at minus 20° C. Liposomes are formed through dialysis at 4° C. against PBS in a 10-kDa Slide-A-Lyzer (Pierce) for 48 h. Biotinylated recombinant MHC is incorporated in rafts, engineered on the aAPC surface. The rafts are constructed by mixing biotinylated HLA-DR4 molecules, biotinylated antibodies to CD28 and anti-LFA-1, and biotinylated Cholera toxin subunit B-FITC conjugated (CTB-FITC; Sigma) in the appropriate (equal) molar ratio. Next, neutravidin (NA; Pierce) is added in a molar ratio of four biotinylated moieties per molecule of NA. CTB-FITC is used to visualize T cells bound by the aAPCs. After incubation (1 h at room temperature), the Raft-NA mixture is added to the liposomes for 2 h, again at room temperature washed twice in PBS. Finally, once the aAPCs are generated, they are incubated with the stained cells as described for the tetramers.

Staining of Cells for FACS Analysis. Cells are washed twice, stained with phycoerythrin, FITC, or cychrome-labeled monoclonal antibodies for human CD3, CD4, and CD25 (PharMingen) and isotype controls for 20 min at 4° C., are again washed twice and are resuspended in staining buffer.

T Cell Capture and Tetramers. For preparation of tetramers, 25 pmol HLA DR4/peptide complex is mixed with 16.7 pmol of NA-FITC (Pierce) for 1 h at room temperature. Next, tetramers are incubated for 2 h at 37° C. with prestained cells. After two washes, specific T cells are analyzed by FACS. T cell capture: stained cells are incubated with aAPCs for 30 min at room temperature. Before acquisition on the FACScalibur or, when cells are sorted, on the FACSvantage (Becton Dickinson), cells and aAPCs are washed twice and are resuspended in staining buffer.

Intracellular Cytokine Staining. PBMCs are cultured for 96 h with medium or antigen. During the last 4 h of culture, monensin (PharMingen) is added. Cells are stained with monoclonal antibodies for human CD3, are washed and incubated in 100 ml of fixation buffer (PharMingen) for 20 min at 40° C. Fixed cells are washed twice, resuspended in 100 ml of permeabilization buffer; and stained with the following monoclonal antibodies: phycoerythrin or FITC-conjugated anti-human IL-4, antihuman IL-10, anti-human IL-2, anti-human TNF-α, anti-human IFN-γ, and the appropriate isotype controls (PharMingen). Finally, cells are washed twice, resuspended in staining buffer, and are analyzed on a FACScalibur.

mRNA Level Quantification. Cytokine (IFN-γ and IL-10) and transcription factor (foxp3) gene expression levels of TCC-sorted dnaJP1-specific T cells are analyzed by multiplex real-time quantitative PCR (TaqMan). The PCR system we used is an ABI PRISM 7700 thermal cycler (Perkin-Elmer) that is capable of distinguishing and quantitating multiple fluorophores in a single tube so that more than one PCR target can be detected for each cDNA sample. TaqMan probes and primers were designed by using the computer software PRIMER EXPRESS (PE Biosystems, Foster City, Calif.). A combination of primers and probes labeled with different dyes have been used such as, for example, (1) IFN-γ (5'-CCAACGCAAAGCAATACATGA-3' forward (SEQ ID NO. 36), 5'-TTTTCGCTTCCCTGTTTTAGCT-3' reverse (SEQ ID NO. 37), 5'-TCCAAGTG ATGGCTGAACTGTCG CC-3' JOE-probe (SEQ ID NO. 38); (2) IL-10 (5'-TGAGAAC AGCTGCACCCACTT-3' forward (SEQ ID NO. 39), 5'-GCTGAAGGCATCTCGGAG AT-3' reverse (SEQ ID NO. 40), 5'-CAGGCAACCTGCCTAACATGCTTCGA-3' FAM-probe (SEQ ID NO. 41); (3) foxp3 (5'-TCACCTACGC-CACGCTCAT-3' forward (SEQ ID NO. 42), 5'-TCATTGAG TGTCCGCTGCTT-3' reverse (SEQ ID NO. 43), 5'-TGGGC-CATCCTGGAGGCTCCA/3BHQ1-3' JOE probe (SEQ ID NO. 44); and (4) GAPDH (5'CCACCCATGGCAAATTCC-3' forward (SEQ ID NO. 45), 5'-TGGGATT TCCATTGAT-GACAAG-3' reverse (SEQ ID NO. 46), 5'-TGGCACCGT-CAAGGCTG AGAACG-3' Tet-Probe (SEQ ID NO. 47). The parameter provided by the 7700 system software is the threshold cycle (Ct) defined as fractional cycle number at which the fluorescence passes a fixed threshold; the higher the initial amount of mRNA, the sooner accumulated product is detected in the PCR process, and the lower the Ct value. The relative mRNA amount for each target gene has been expressed as 1/Ct proband-100/Ct GAPDH. Calculations were performed by the relative standard curve method and results were expressed as induction index (arbitrary units), using as a reference the no-stimulated condition at each time point.

Statistical Analysis. A Mann-Whitney U test was used to compare the different data. Kolmogorov-Smirnov statistics were used to analyze FACS cytokine staining. Foxp3 data were evaluated by ANOVA after removing the interaction term and running a main-effects-only model.

Results and Discussion

Mucosal Immune Therapy with dnaJP1 Is Safe. Treatment with dnaJP1 was well tolerated because no significant side effects were reported. The clinical characteristics of the patients were monitored closely to identify any treatment-related clinical deterioration. Physicians recorded affected joint scores and numbers and overall disease activity. Self-assessment by patients was performed by using the Rapid Assessment of Disease Activity in Rheumatology. Both physician- and patient-generated data showed a marked improvement from baseline. Because this study was not aimed at evaluating clinical efficacy, and no placebo treated control was included in this pilot trial, we refrain from showing the clinical data, which we interpret only as indicating that the treatment was safe and that certainly did not worsen the disease. Based on the encouraging preliminary data from this phase I trial, future research is warranted to evaluate the clinical efficacy of the treatment.

Mucosal Tolerization to dnaJP1 Leads to a Peptide-Specific Immune Deviation in PBMCs from Patients with RA. Immunological evaluation showed remarkable treatment-specific changes in responsiveness to dnaJP1. dnaJP1-induced T cell production of IL-10 and IL-4 increased significantly from baseline at the second month and continued throughout the treatment period ($P<0.001$ at day 168 compared with day 0, FIG. 20). Conversely, we observed a strong decline in both T cell proliferation and production of proinflammatory cytokines IFN-$\gamma$ and TNF-$\alpha$ in response to dnaJP1 stimulation in vitro (FIG. 20). These changes were already statistically significant for all parameters considered at the second month and persisted throughout the length of the study. All treatment groups showed similar trends in treatment-induced immune deviation, suggesting that the dosages tested were within the biological range necessary to induce immune deviation. Controls comprised mitogens (phytohaemagglutinin) and irrelevant peptides, including dnaJPv, an altered peptide ligand not stimulatory in patients, and PADRE, a designer pan-DR-binding peptide immunogenic in humans irrespective of DR restriction (FIG. 20). The control experiments showed that the immune modulation obtained was antigen-specific, and that the patients' physiologic immune responses remained intact.

The fact that the responses to unrelated antigens did not change over time ruled out the possibility of a treatment independent, random change in the quality of immune responsiveness (i.e., Th1 vs. Th2/3) in all patients treated. Thus, the changes were the outcome of a true immune deviation from a proinflammatory (IFN-$\gamma$, TNF-$\alpha$, and T cell proliferation) to a more regulatory (IL-4 and IL-10) functional phenotype of the dnaJP1-specific T cell repertoire.

Mucosal Therapy with dnaJP1 Does Not Lead to Clonal Deletion of dnaJP1-Specific Cells. The persistence of T cell recognition of dnaJP1 in treated patients, as shown by production of regulatory cytokines after initiation of treatment, suggests that immune deviation, rather than clonal deletion of peptide-specific T cells took place. To address this question directly, we enumerated dnaJP1-specific T cells by TCC, a recently described method, based on aAPCs. We showed that these aAPCs can effectively bind low-affinity polyclonal MHC class II-restricted CD3+ T cells, thus providing an excellent tool to characterize antigen-specific CD4+ T cells. This task is very difficult to achieve by using state-of-the-art MHC tetramer technology.

Figure 21:
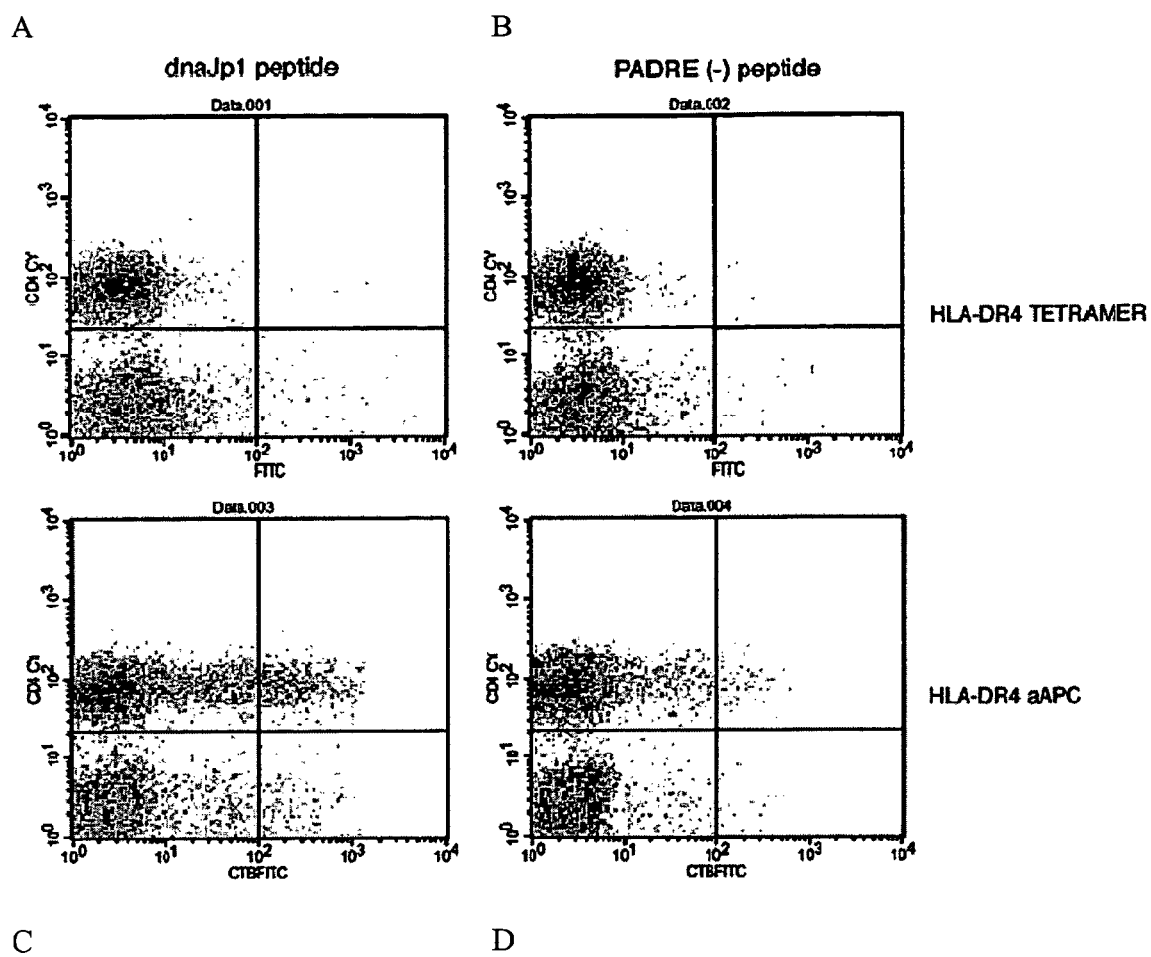
FIG. 21. Comparison between tetramer and T cell capture technology for the detection of dnaJP1-specific T cells in PBMCs from patients with RA. PBMCs from a representative HLA-DRB1*0401-positive RA patient under treatment with dnaJP1 peptide were put in culture during 48 h with 10 μg/ml dnaJP1 peptide. After in vitro stimulation, PBMCs stained with anti CD4 (phycoerythrin) antibody were incubated with tetramers (FITC) or aAPCs (FITC) loaded with a dnaJP1 or negative control PADRE (−).

First, we compared the efficiency of TCC and tetramer technology in measuring dnaJP1-specific T cells in PBMCs from patients with RA. For this purpose, we engineered aAPCs with GM-1 ganglioside as part of the lipid bilayer. GM-1 binds one molecule of biotinylated CTB. In each raft, one molecule of NA anchors the biotinylated molecules to the aAPC surface through one biotinylated CTB, whereas the remaining three free valences of NA are saturated with MHC/peptide complex consisting of HLA DRB1*0401 molecules loaded with dnaJP1 or the appropriate control peptide [PADRE (-)], anti-CD28 antibody, and anti-LFA-1 antibody. Detection of dnaJP1-specific T cells from dnaJP1-stimulated PBMC cultures was possible by using aAPCs, and was more effective then tetramer staining of the same samples (FIG. 21). Thus, as in the other models tested before, TCC provided a very effective tool to enumerate and characterize dnaJP-specific T cells in PBMCs from patients with RA as will be well understood by one of ordinary skill in the art.

We then applied TCC to identify dnaJP1-specific T cells in PBMCs from patients included in this study. By using this approach, we compared the number of dnaJP1-specific T cells as the percentage of total T cells before and after mucosal tolerization with dnaJP1. This number did not change significantly after treatment (before treatment: 6.5±2.5% vs. after treatment: 8.0±2.5%, P=0.3, n=6).

These experiments demonstrated that although treatment with dnaJP1 led to a significant decrease in antigen-induced proinflammatory cytokine production and T cell-proliferative capacities, this result was not due to a loss in total number of antigen-specific T cells.

Figure 22:
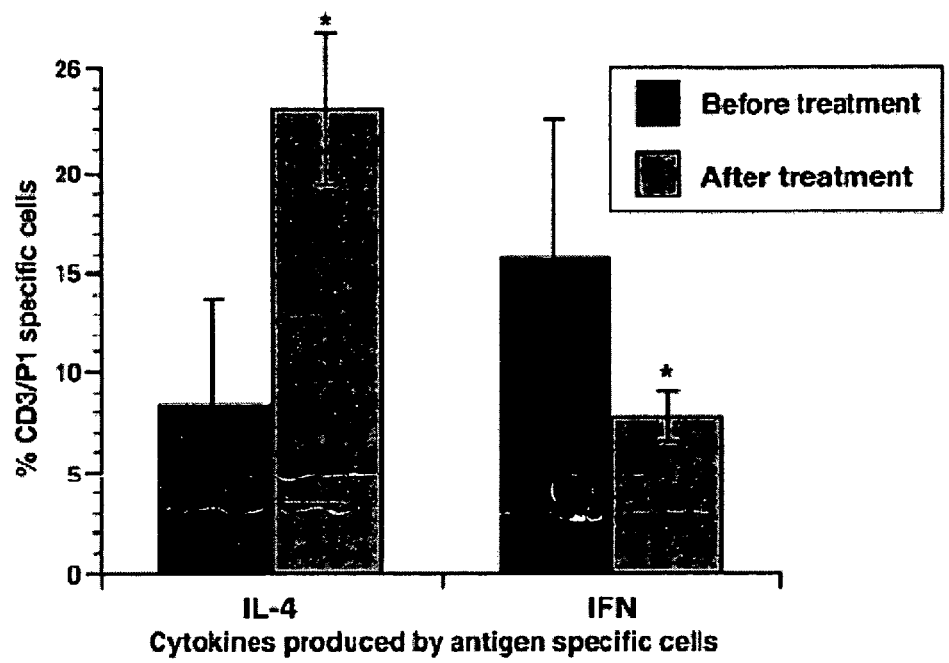
FIG. 22. Characterization of peptide-specific dnaJP1 human MHC class II-restricted T cells with TCC. Cytokine production by dnaJP1-specific MHC class II-restricted cells after in vitro activation with dnaJP1 before and after treatment with dnaJP1. PBMCs from six patients included in this study were expanded in vitro with dnaJP1. Viable cells were harvested, permeabilized, stained for surface markers and intracellular cytokines (IL-4 and IFN-γ), incubated with aAPCs loaded with MHC class II and dnaJP1, and analyzed by FACS. The number of T cells producing either IFN-γ or IL-4 within the dnaJP1-specific population was calculated as percentage of the total number of dnaJP1-specific CD3-positive cells (y axis). Columns represent means (black bars, before treatment; gray bars, after treatment), and error bars represent SD. *, statistical significance.

Mucosal Therapy with dnaJP1 Leads to a Functional Shift of dnaJP1-Specific Cells. It remained, however, still to be addressed whether dnaJP1-specific T cells may have been rendered functionally incompetent by the treatment. We combined TCC with intracellular cytokine staining to monitor the changes in cytokine production within the population of antigen-specific T cells. After immunotherapy with dnaJP1, we observed a significant increase in the percentage of cells producing IL-4 within the total dnaJP1-specific CD3+ population (before treatment: 8.4±5.4%, after treatment: 23.1±3.8%, P<0.05, n=6). A corresponding significant reduction in percentage of CD3+/dnaJP1-specific cells producing IFN-$\gamma$ was found (before treatment: 15.8±6.7%, after treatment: 7.9±1.4%, P=0.05, n=6; FIG. 22).

Several mechanisms could explain the discrepancy between the significant decline in the number of polyclonal T cells producing IFN-$\gamma$ after treatment and the persistence of IFN-$\gamma$-producing, dnaJP1-specific T cells (FIGS. 20 Left and 22). One possibility, for example, is that different populations of dnaJP1-specific T cells are affected by the treatment. Among these cells, T regulatory-1-like T cells that produce IFN-$\gamma$ and IL-10 may be of importance.

To explore this hypothesis, dnaJP1-specific T cells were sorted from selected samples (n=4) at baseline and at the end of treatment. mRNA was extracted and analyzed by real-time-PCR (TaqMan), for simultaneous expression of IFN-$\gamma$ and IL-10. We found dnaJP1-specific T cells, which produce IFN-$\gamma$ and IL-10 at the same time, at the end of the treatment period (IFN-γ: 0.081±0.0054, IL-10: 0.075±0.013, 1/Ct proband-100/Ct GAPDH, n=4), supporting the hypothesis that the immune deviation observed may, at least in part, be depending on regulatory cells.

After Mucosal Tolerance Induction, in Vitro Activation with dnaJP1 Leads to Increased Expression of foxP3 by $CD4_{13}$ CD25 bright Cells. To corroborate the concept that tolerization to dnaJP1 did not alter total numbers but rather the function of T cells, we focused on cells with a regulatory function (Treg), which are being increasingly proposed as central in immune regulation. A combination of functional and phenotypical markers, centered on CD4/CD25-double positive T cells was used to identify these cells. Recent work did not find differences in number of $CD25^{bright}$ T cells between synovial fluids from human rheumatoid arthritis patients and normals. Because it is well known that Treg are difficult to expand in response to antigens, we focused on function rather than absolute numbers. The hypothesis, consistent with the our data, was that restoration of Treg function could be one of the consequences of our immunotherapy. For this purpose, we studied expression of the forkhead transcription factor foxP3. FoxP3 expression affects positively development and function of Treg. It is therefore been proposed as a functional marker of these cells.

Figure 23:
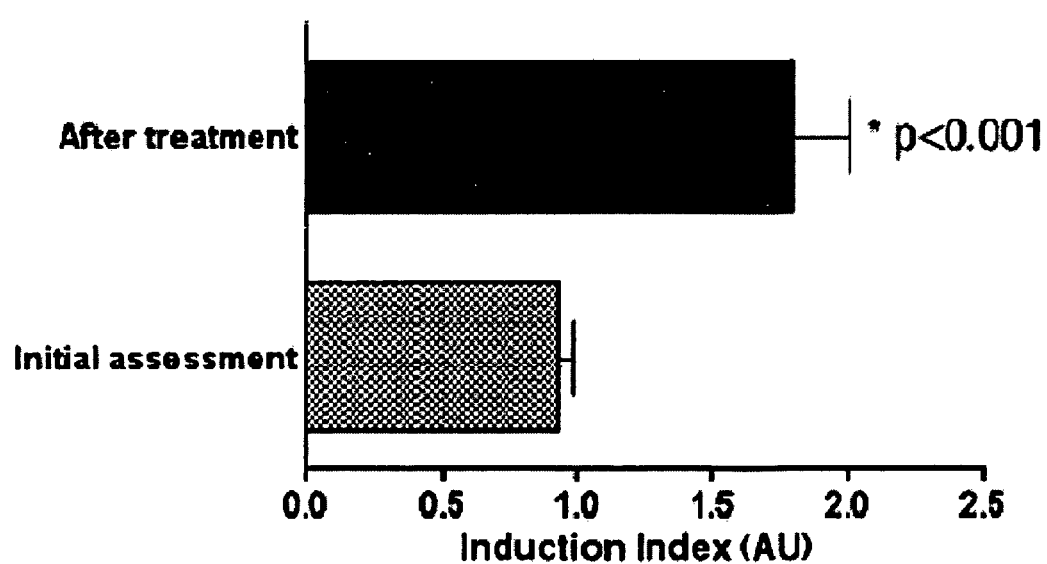
FIG. 23. Increased expression of foxP3 by CD4+/CD25+ T cells of patients after treatment with dnaJP1. Two representative patients were analyzed for foxP3 transcription factor expression. PBMCs obtained at initial evaluation and at the end of the treatment were sorted for CD4+/CD25+ cells before and after 48 h in vitro stimulation with dnaJP1. Total RNA was extracted, and the gene expression profile was analyzed by TaqMan. Results are expressed as Ct values, which were normalized according the expression of GAPDH. Induction index is the result of normalization process (arbitrary units) and refers to how many times the gene expression changed compared with not stimulated. Data were evaluated by ANOVA after removing the interaction term and running a main-effects-only model. Columns represent means, and bars represent SD.

In the experiments shown here, we tested whether tolerization to dnaJP1 would induce foxP3 expression as an indication of restored Treg function. Samples before and after tolerization from two patients were cultured in vitro with dnaJP1. $CD4+CD25^{bright}$ cells were sorted and assessed for foxP3 expression by TaqMan. Significantly increased ($P<0.001$) Foxp3 expression by $CD4+CD25^{bright}$ cells after tolerization was achieved (FIG. 23).

Altogether, these data demonstrate that the functional switch from proinflammatory to tolerogenic responses to dnaJP1 was an active phenomenon of immune deviation mediated by functionally competent antigen-specific T cells, probably consisting of various populations with diverse and integrated regulatory functions.

CONCLUSION

We have characterized a T cell-dependent, proinflammatory pathway that can be specifically and safely modulated in patients with RA. Our findings show that epitope-specific mucosal therapy does not lead to a change in the number of epitope-specific T cells, but rather to a functional readjustment of the responding antigen-specific T cells, based on a functional change from a proinflammatory to a regulatory phenotype. This finding shows that committed Th1 cells can still undergo a phenotypic change, which previously was considered by those of ordinary skill in the art to be impossible.

In keeping with the contemplated method of the invention set forth throughout this disclosure, the peptide studied in this Example is part of a pool of antigens that share characteristics such as their availability at the site of inflammation, strong proinflammatory effect on T cell responses in RA and, in certain instances, interspecies homologies. Peptides derived from heat shock protein fulfill this profile. dnaJP1, hence, is particularly attractive in this context, not only for its homology with the shared epitope but also for its potential role in autoimmune inflammation as a heat shock protein-derived peptide. This finding may explain the fact that the small proportion of shared epitope-negative patients in our study had detectable responses to the peptide and was tolerized by the treatment.

Further, this Example shows all aspects of the methodology of treatment comprising design of hsp-derived peptides for MHC class II binding. Such peptides can also be created from in-silico design concepts and computer models. The study utilized ex vivo assessment of proinflammatory responses (IFN-g, TNF-a) to peptides in patients peripheral blood or biopsies, and correlation of immunological and clinical data and stratification of patient populations, all of which provides clinical leads to new treatment possibilities based generally on epitope-specific immune modulation, more specifically by altering T cell functional phenotype, and even more particularly by modulating the regulatory phenotype of regulatory T cells and/or inducing emergence of T cells with a different functional phenotype, such as, for example, from a proinflammatory response to a regulator or even a tolerogenic response. Likewise, the invention methods contemplate altering T cell functional phenotype from a regulatory or tolerogenic to a proinflammatory response. In a paper recently accepted for publication in the journal Lancet (Tolerogenic immune responses to novel T cell epitopes from heat shock protein 60 in juvenile idiopathic arthritis. Sylvia Kamphuis, Wietse Kuis, Wilco de Jager, Gijs Teklenburg, Margherita Massa, Grace Gordon, Marjolein Boerhof, Ger T Rijkers, Cuno S Uiterwaal, Henny G Otten, Alessandro Sette, Salvatore Albani, Berent J Prakken.) It has been shown that in Juvenile Idiopathic Arthritis (JIA), patients T cell reactivity to self-heat shock protein 60 (HSP60) correlates with a favourable prognosis and confirms the presence of natural immunoreactivity towards these peptides in patients with JIA.

Although the invention has been described with reference to the above examples, it will be understood that modification and variations are encompassed within the spirit and scope of the invention. Accordingly, the invention is limited only by the following claims.

What is claimed is:

1. An isolated peptide consisting of the amino acid sequence as set forth in SEQ ID NO: 24.

2. The isolated peptide of claim 1, wherein the peptide is at least about 90% pure by weight.

3. The isolated peptide of claim 1 wherein the peptide contains one or more D-amino acids.

4. The isolated peptide of claim 1 wherein the peptide is covalently linked to an adjuvant.

5. The isolated peptide of claim 4 wherein the adjuvant is selected from the group consisting of keyhole limpet hemocyanin, bovine serum albumin, human serum albumin, and isologous IgG.

6. A pharmaceutical composition comprising the peptide of claim 1 in a pharmaceutically acceptable carrier.

7. A composition comprising a pharmaceutically acceptable carrier and the isolated peptide of claim 4.

8. The composition of claim 7 wherein the peptide binds to a molecule selected from the group consisting of HLADR1, DR4, and DR7.

9. The isolated peptide of claim 1, wherein the peptide is chemically synthesized.

10. The isolated peptide of claim 1, wherein the peptide is glycosylated.

* * * * *

UNITED STATES PATENT AND TRADEMARK OFFICE
CERTIFICATE OF CORRECTION

PATENT NO. : 7,608,683 B2
APPLICATION NO. : 11/080458
DATED : October 27, 2009
INVENTOR(S) : Albani et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 285 days.

Signed and Sealed this

Twelfth Day of October, 2010

David J. Kappos
*Director of the United States Patent and Trademark Office*